US012743772B2

(12) United States Patent
Dhatt et al.

(10) Patent No.: US 12,743,772 B2
(45) **Date of Patent: *Sep. 22, 2026**

(54) IDENTIFYING BLOOD VESSELS IN ULTRASOUND IMAGES

(71) Applicant: FUJIFILM SONOSITE, INC., Bothell, WA (US)

(72) Inventors: Davinder S. Dhatt, Bothell, WA (US); Christopher Aleksandr White, Bothell, WA (US); Adam Benjamin Pely, Bothell, WA (US); Thomas Michael Duffy, Bothell, WA (US); Paul Tomotaro Danset, Bothell, WA (US); Diku Pranav Mandavia, Bothell, WA (US)

(73) Assignee: FUJIFILM SONOSITE, INC., Bothell, WA (US)

(*) Notice: Subject to any disclaimer, the term of this patent is extended or adjusted under 35 U.S.C. 154(b) by 201 days.

This patent is subject to a terminal disclaimer.

(21) Appl. No.: 18/413,624

(22) Filed: Jan. 16, 2024

(65) Prior Publication Data

US 2024/0153080 A1 May 9, 2024

Related U.S. Application Data

(63) Continuation of application No. 17/239,314, filed on Apr. 23, 2021, now Pat. No. 11,900,593.

(51) Int. Cl.
*G06T 7/00* (2017.01)
*A61B 8/08* (2006.01)

(52) U.S. Cl.
CPC ............ *G06T 7/0012* (2013.01); *A61B 8/085* (2013.01); *G06T 2207/10016* (2013.01);
(Continued)

(58) Field of Classification Search
CPC ......... A61B 8/085; A61B 8/5223; A61B 8/06; A61B 8/5207; A61B 8/463; A61B 8/4263;
(Continued)

(56) References Cited

U.S. PATENT DOCUMENTS 6,048,317 A 4/2000 Langguth
6,245,018 B1 6/2001 Lee
(Continued)

FOREIGN PATENT DOCUMENTS

CN 101500490 A 8/2009
CN 102805651 A 12/2012
(Continued)

OTHER PUBLICATIONS

Ruben Hemelings, Bart Elen, Ingeborg Stalmans, Karel Van Keer, Patrick De Boever, Matthew B. Blaschko, Artery-vein segmentation in fundus images using a fully convolutional network, Computerized Medical Imaging and Graphics, vol. 76, 2019, 101636 (Year: 2019).*

(Continued)

*Primary Examiner* — Alex Kok S Liew

(74) *Attorney, Agent, or Firm* — Womble Bond Dickinson (US) LLP

(57) ABSTRACT

A method and apparatus for identifying blood vessels in ultrasound images and displaying blood vessels in ultrasound images are described. In some embodiments, the method is implemented by a computing device and includes assigning, with a neural network implemented at least partially in hardware of the computing device, one of a vein classification and an artery classification to one or more blood vessels in ultrasound images. The method also includes determining a misclassification for one blood vessel that denotes the neural network assigning the one of the vein
(Continued)

classification and the artery classification to the one blood vessel in one ultrasound image and the other of the vein classification and the artery classification to the one blood vessel in additional ultrasound images. The method includes displaying, in the one ultrasound image, an indication of the other of the vein classification and the artery classification for the one blood vessel.

20 Claims, 26 Drawing Sheets

(52) U.S. Cl.
CPC ............... *G06T 2207/10024* (2013.01); *G06T 2207/10132* (2013.01); *G06T 2207/20081* (2013.01); *G06T 2207/20084* (2013.01); *G06T 2207/30101* (2013.01)

(58) Field of Classification Search
CPC ............ A61B 2090/378; A61B 8/0883; A61B 2090/365; A61B 8/4427; A61B 8/52; A61B 8/467; A61B 8/469; A61B 8/4245; A61B 8/466; A61B 8/4254; A61B 8/585; A61B 34/20; A61B 8/483; A61B 2034/2048; A61B 2034/2055; A61B 8/5215; A61B 2090/3945; A61B 8/065; A61B 8/0833; A61B 8/46; A61B 90/361; A61B 2034/2065; G06T 2207/10132; G06T 2207/20081; G06T 2207/20084; G06T 2207/30048; G06T 7/0012; G06T 7/0014; G06T 19/006; G06T 2207/20221; G06T 7/70; G06T 11/60; G06T 2207/30061; G06T 2210/41; G06T 2207/10016; G06T 7/11; G06T 2207/10116; G06T 2207/30104
See application file for complete search history.

(56) References Cited

U.S. PATENT DOCUMENTS

| | | | |
|---|---|---|---|
| 9,731,066 | B2 | 8/2017 | Liu et al. |
| 10,902,585 | B2 | 1/2021 | Nett |
| 2008/0226017 | A1 | 9/2008 | Altman et al. |
| 2008/0269605 | A1 | 10/2008 | Nakaya |
| 2009/0103794 | A1 | 4/2009 | Sathyanarayana |
| 2010/0161023 | A1 | 6/2010 | Cohen et al. |
| 2011/0033098 | A1 | 2/2011 | Richter et al. |
| 2012/0310089 | A1 | 12/2012 | Miyachi et al. |
| 2013/0016092 | A1 | 1/2013 | Collins et al. |
| 2013/0102889 | A1 | 4/2013 | Southard et al. |
| 2013/0150710 | A1 | 6/2013 | Zentgraf et al. |
| 2013/0165789 | A1 | 6/2013 | Yao et al. |
| 2013/0197367 | A1 | 8/2013 | Smok et al. |
| 2014/0031690 | A1 | 1/2014 | Toji et al. |
| 2014/0188133 | A1 | 7/2014 | Misener |
| 2014/0249404 | A1 | 9/2014 | Lee et al. |
| 2014/0343431 | A1 | 11/2014 | Vajinepalli et al. |
| 2015/0005630 | A1 | 1/2015 | Jung et al. |
| 2015/0126865 | A1 | 5/2015 | Murai et al. |
| 2015/0209113 | A1 | 7/2015 | Burkholz et al. |
| 2015/0238165 | A1 | 8/2015 | Hyuga |
| 2015/0283319 | A1 | 10/2015 | Tolkowsky et al. |
| 2016/0117814 | A1 | 4/2016 | Kim et al. |
| 2016/0150980 | A1 | 6/2016 | Lee et al. |
| 2018/0014810 | A1 | 1/2018 | Chen et al. |
| 2018/0015256 | A1 | 1/2018 | Southard et al. |
| 2018/0137244 | A1 | 5/2018 | Sorenson et al. |
| 2018/0243033 | A1 | 8/2018 | Tran et al. |
| 2018/0247154 | A1 | 8/2018 | Kitamura |
| 2018/0374233 | A1 | 12/2018 | Zhou et al. |
| 2019/0008412 | A1 | 1/2019 | Davies |
| 2019/0282199 | A1 | 9/2019 | Merritt |
| 2019/0365350 | A1 | 12/2019 | Chiang |
| 2020/0129159 | A1 | 4/2020 | Rajguru et al. |
| 2020/0394789 | A1 | 12/2020 | Freund et al. |
| 2021/0045710 | A1 | 2/2021 | Bedi et al. |
| 2021/0045711 | A1* | 2/2021 | Brattain ............... A61B 8/4209 |
| 2021/0045716 | A1 | 2/2021 | Shiran et al. |
| 2021/0113194 | A1 | 4/2021 | Padwal et al. |
| 2021/0128099 | A1 | 5/2021 | Al-Noor et al. |
| 2021/0128101 | A1* | 5/2021 | Matsumoto ............ A61B 8/403 |
| 2021/0209757 | A1 | 7/2021 | Min et al. |
| 2022/0104789 | A1 | 4/2022 | Matsumoto et al. |
| 2022/0142608 | A1 | 5/2022 | Matsumoto |
| 2022/0230363 | A1 | 7/2022 | Sasaki et al. |

FOREIGN PATENT DOCUMENTS

| | | | |
|---|---|---|---|
| CN | 103169500 | A | 6/2013 |
| CN | 111134727 | A | 5/2020 |
| EP | 4014890 | A1 | 6/2022 |
| JP | H0499566 | A | 3/1992 |
| JP | 11-235342 | A | 8/1999 |
| JP | 2007-222291 | A | 9/2007 |
| JP | 2008-272025 | A | 11/2008 |
| JP | 2010-521198 | A | 6/2010 |
| JP | 2010-269018 | A | 12/2010 |
| JP | 2015-089383 | A | 5/2015 |
| JP | 2015-154883 | A | 8/2015 |
| JP | 2017-509372 | A | 4/2017 |
| JP | 2018-015356 | A | 2/2018 |
| JP | 2018-139693 | A | 9/2018 |
| JP | 2018-171177 | A | 11/2018 |
| JP | 2019-150345 | A | 9/2019 |
| JP | 2019-534110 | A | 11/2019 |
| JP | 2020-512069 | A | 4/2020 |
| JP | 2021-037239 | A | 3/2021 |
| WO | 2019/171986 | A1 | 9/2019 |
| WO | 2020/002810 | A1 | 1/2020 |
| WO | 2020/044769 | A1 | 3/2020 |
| WO | 2021/014767 | A1 | 1/2021 |
| WO | 2021/033446 | A1 | 2/2021 |
| WO | 2021/033491 | A1 | 2/2021 |
| WO | 2022/212414 | A1 | 10/2022 |

OTHER PUBLICATIONS

Extended European Search Report and Search Opinion received for European Application No. 22792637.5, mailed on Apr. 23, 2025, 10 pages.

Final Office Action received for U.S. Appl. No. 18/397,826, mailed on May 2, 2025, 49 pages.

Notice of Allowance received for U.S. Appl. No. 17/239,335, mailed on Apr. 2, 2025, 8 pages.

International Preliminary Report on Patentability received for PCT Patent Application No. PCT/US2022/026087, mailed on Nov. 2, 2023, 9 pages.

International Preliminary Report on Patentability received for PCT Patent Application No. PCT/US2022/026089, mailed on Nov. 2, 2023, 7 pages.

International Preliminary Report on Patentability received for PCT Patent Application No. PCT/US2022/026122, mailed on Nov. 2, 2023, 8 pages.

International Search Report and Written Opinion received for PCT Patent Application No. PCT/US22/26087, mailed on Aug. 11, 2022, 11 pages.

International Search Report and Written Opinion received for PCT Patent Application No. PCT/US22/26089, mailed on Aug. 11, 2022, 9 pages.

International Search Report and Written Opinion received for PCT Patent Application No. PCT/US22/26122, mailed on Aug. 9, 2022, 10 pages.

Mishra et al., "Ultrasound Image Segmentation: A Deeply Supervised Network With Attention to Boundaries", IEEE Transactions on Biomedical Engineering, vol. 66, No. 6, Jun. 2019, pp. 1637-1648.

(56) References Cited

OTHER PUBLICATIONS

Advisory Action received for U.S. Appl. No. 17/239,335, mailed on Nov. 29, 2024, 4 pages.
Decision to Grant a patent received for Japanese Patent Application No. 2023-565331, mailed on Dec. 17, 2024, 6 pages (2 pages of English Translation and 4 pages of Original Document).
Extended European Search Report and Search Opinion received for European Application No. 22792635.9, mailed on Jan. 31, 2025, 9 pages.
Extended European Search Report and Search Opinion received for European Application No. 22792636.7, mailed on Jan. 22, 2025, 8 pages.
Final Office Action received for U.S. Appl. No. 17/239,335, mailed on Sep. 6, 2024, 26 pages.
Non-Final Office Action received for U.S. Appl. No. 17/239,335, mailed on Mar. 13, 2024, 25 pages.
Non-Final Office Action received for U.S. Appl. No. 18/397,826, mailed on Nov. 7, 2024, 27 pages.
Notice of Reasons for Refusal received for Japanese Patent Application No. 2023-565331, mailed on Aug. 27, 2024, 13 pages (6 pages of English Translation and 7 pages of Original Document).
Partial Supplementary European Search Report and Search Opinion received for European Application No. 22792637.5, mailed on Jan. 30, 2025, 10 pages.
Requirement for Restriction/Election received for U.S. Appl. No. 18/397,826, mailed on Sep. 23, 2024, 12 pages.
Wang, D. C., et al., "Fully Automated Common Carotid Artery and Internal Jugular Vein Identification and Tracking Using B-Mode Ultrasound", IEEE Transactions On Biomedical Engineering, vol. 56, No. 6, Jun. 1, 2009, pp. 1691-1699.
Notice of Allowance received for U.S. Appl. No. 17/239,335, mailed on May 27, 2025, 2 pages.
Notice of Allowance received for U.S. Appl. No. 18/397,826, mailed on Aug. 26, 2025, 16 pages.
Notice of Reasons for Refusal received for Japanese Patent Application No. 2025-006400, mailed on Dec. 9, 2025, 6 pages (3 pages of English Translation and 3 pages of Original Document).
CN Office Action, Including Search report received for Chinese Patent Application No. 202280030439.1, mailed on Mar. 13, 2026, 16 pages (8 pages of English Translation and 8 pages of Original Document).
Decision to Grant a Patent received for Japanese Patent Application No. 2025-006400, mailed on Mar. 24, 2026, 6 pages (2 pages of English Translation and 4 pages of Original Document).
Office Action received in related Chinese application No. 202280030392.9, mailed Jul. 14, 2026, 16 pages.
Notification for Divisional Application received in related Chinese application No. 202280030392.9, mailed Apr. 15, 2026, 2 pages.
Office Action received for Chinese Patent Application No. 202280030417.5, mailed on May 21, 2026, 6 pages (3 pages of English Translation and 3 pages of Original Document).
Non-Final Office Action received for U.S. Appl. No. 19/233,311, mailed on Jun. 16, 2026, 21 pages.

* cited by examiner 1101
1102
1103

1101
1102
1103

1101
1102
1103

1101
1102
1103

IDENTIFYING BLOOD VESSELS IN ULTRASOUND IMAGES

RELATED APPLICATIONS

This application is a Continuation of U.S. patent application Ser. No. 17/239,314 filed Apr. 23, 2021, titled “Identifying Blood Vessels in Ultrasound Images.” This application is related to U.S. patent application Ser. No. 17/239,323 filed Apr. 23, 2021, titled “Guiding Instrument Insertion”, and U.S. patent application Ser. No. 17/239,335 filed Apr. 23, 2021, titled “Displaying Blood Vessels in Ultrasound Images”, both concurrently filed and incorporated herein by reference.

FIELD

One or more exemplary embodiments relate to an ultrasound machine and a method of operating the same, and more particularly, to an ultrasound machine that identifies blood vessels in ultrasound images and displays the blood vessels in an enhanced manner by including information about the blood vessels useful to an operator of the ultrasound machine.

BACKGROUND

Ultrasound systems radiate an ultrasonic signal generated from an ultrasound probe into an object, such as a patient, and receive echo signals reflected from an internal part of the object. An image of the internal part of the object is generated using the received echo signals. More specifically, ultrasound diagnostic machines generate an ultrasound image by using ultrasonic image data acquired from an ultrasound probe and display the generated ultrasound image on a screen to provide the ultrasound image to a user. The ultrasound machine can include a control panel for controlling the ultrasound machine and setting various functions, such as a gain or frequency setting.

Procedures for which ultrasound machines are often used include ultrasound-guided insertion of an interventional instrument, such as peripheral intravenous (PIV) catheterization. In performing ultrasound-guided PIV catheterization, a clinician may initially perform a survey scan of a body using the ultrasound machine to look for appropriate veins for cannulation. Suitable veins have the following characteristics: generally greater than 0.3 mm diameter; generally not located near an artery that could be accidentally damaged during cannulation; they are sufficiently large such that the catheter-to-vein diameter ratio is greater than 0.45 (although other rules of thumb exist such as 0.33); the vein is relatively straight and not tortuous; and the vein does not contain valves that would be hit by the catheter.

To determine the diameter and depth of the vein within the subject, the clinician can either eyeball (e.g., estimate) the measurement, which is prone to error, or they can turn on the calipers and measure to get a more precise diameter and depth. In practice, clinicians rarely use the calipers because of the time it takes and the desire to not touch the ultrasound machine while they are performing this procedure (both for sterility and workflow). Hence, there’s a need that the clinician can easily see and identify a blood vessel suitable for inserting a catheter, a needle, etc.

SUMMARY

Methods, systems, and apparatuses for identifying blood vessels in ultrasound images and displaying blood vessels in ultrasound images are described.

In some embodiments, a method is implemented by a computing device for identifying blood vessels, such as an ultrasound machine or a tablet coupled to the ultrasound machine, and includes assigning, with a neural network implemented at least partially in hardware of the computing device, one of a vein classification and an artery classification to one or more blood vessels in ultrasound images, and determining a misclassification for one blood vessel of the one or more blood vessels. The misclassification denotes the neural network assigning the one of the vein classification and the artery classification to the one blood vessel in one ultrasound image of the ultrasound images and the other of the vein classification and the artery classification to the one blood vessel in additional ultrasound images of the ultrasound images. The method also includes displaying, in the one ultrasound image, an indication of the other of the vein classification and the artery classification for the one blood vessel.

In some embodiments, an ultrasound system for identifying blood vessels includes an image module to generate ultrasound images based on ultrasound echo signals, a neural network module to identify the blood vessels in a first image of the ultrasound images, and a map module to generate a map image that indicates locations of the blood vessels in the first image identified by the neural network module. The neural network module identifies the blood vessels in a second image of the ultrasound images based on the map image and the second image.

In some embodiments, a method is implemented by a computing device for identifying blood vessels, such as an ultrasound machine or a tablet coupled to the ultrasound machine, and includes determining, with a neural network implemented at least partially in hardware of the computing device, bounding containers of blood vessels in ultrasound images, and determining compression amounts of the blood vessels based on the bounding containers. The method also includes assigning, with the neural network, classifications of a vein classification or an artery classification to the blood vessels in the ultrasound images, and determining labels for the blood vessels based on the compression amounts and the classifications, the labels indicating the blood vessels as a vein or an artery.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding.

DETAILED DESCRIPTION

Figure 1B:
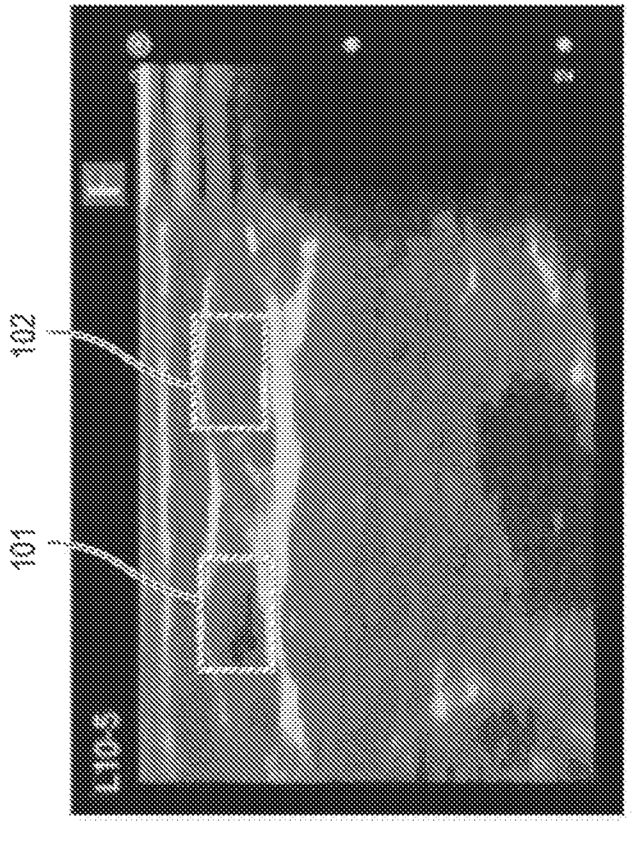
FIGS. 1A and 1B illustrate an example of detecting two blood vessels and identifying them with boxes.

In the following description, numerous details are set forth to provide a more thorough explanation of the present invention. It will be apparent, however, to one skilled in the art, that the present invention may be practiced without these specific details. In some instances, well-known structures and devices are shown in block diagram form, rather than in detail, to avoid obscuring the present invention.

Overview

Techniques for identifying blood vessels in ultrasound images and displaying blood vessels in ultrasound images are disclosed. In some embodiments, these techniques are performed by an ultrasound machine. Examples of such ultrasound machines are described in greater detail below. For purposes herein the term "ultrasound machine", "ultrasound system", and "ultrasound imaging system" may be used interchangeably.

In some embodiments, the ultrasound machine executes detection software to perform blood vessel detection on areas of an ultrasound image, and the results of that detection are displayed on a monitor or display of the ultrasound machine, such as, for example, a clinical display or a tablet coupled to the ultrasound machine. The execution can be performed by one or more processors or execution engines. In some embodiments, the ultrasound machine performs blood vessel detection using template matching, artificial intelligence (AI) or machine-learning (e.g., adaptive boosting (adaboost), deep-learning, supervised learning models, support vector machine (SVM), sequence models including recurrent neural networks (RNN), Gated Recurrent Unit (GRU), convolutional GRU (ConvGRU), long short-term memory (LSTM), etc., to process frame information in sequence, etc.), and/or another suitable detection method. Additionally or alternatively, the ultrasound machine can execute an AI algorithm and/or use a neural network to identify veins and arteries and locate them in an ultrasound image.

In some embodiments, after the detection software detects blood vessels, the ultrasound machine displays the blood vessels on a monitor or display of the ultrasound system. In some embodiments, the ultrasound machine displays the detected blood vessels in an enhanced manner to provide information to the operator, e.g., a user of the ultrasound machine. For example, the ultrasound machine can draw outlines or other forms of blood vessel indicia (e.g., identifiers) around or in the proximity of the blood vessels.

By displaying blood vessels in an enhanced form, additional information is provided to the operator. For example, an outline of a vein can be changed to match the color coding of the largest catheter that could fit within that vein to the extent of catheter-to-vein diameter ratio (e.g., 0.45, or 0.33). Thus, an operator may select a catheter size based on the blood vessels and their indicia being displayed. Additionally or alternatively, the ultrasound machine can identify all veins in an ultrasound image that are appropriate for a particular catheter size. For instance, an operator may select a catheter size on a user interface of the ultrasound machine, and in response, the ultrasound machine can designate the veins in the ultrasound image suitable for the catheter size (e.g., based on ratios of the catheter size to diameters of the veins), such as by changing a color of an indicator of the veins suitable for the catheter size, removing indicators of veins that are not suitable for the catheter size, combinations thereof, and the like. In one example, an operator is able to touch a vein in the ultrasound image and have the ultrasound machine display the diameter and depth for that blood vessel. Additionally or alternatively, the ultrasound machine can automatically identify the most central and shallowest vein, and automatically provide the diameter and depth for that vein on a display of the ultrasound machine.

In some embodiments, particular organizations of arteries and veins can be detected as a unified structure. For example, a triad is a vein-artery-vein collection where a central artery is closely bounded on either side by a vein. In one example, the AI can distinctly detect and classify the veins and arteries in the triad as individual components. However, because of the unique configuration of the triad structure, this grouping can be detected as an additional unique classification alongside veins and arteries. By doing so, the overall accuracy of the detection can increase as the triad always occurs in vein-artery-vein configuration. A group of three closely detected vessels, for example, vein, vein, artery, where the central vein is bounded by a vein and an artery, is likely a misclassification or misdetection. By detecting this group as a triad, the exact classification of each of the vessels can be improved.

In some embodiments, the ultrasound machine calculates a likelihood value for each detected blood vessel as an indication of a confidence level associated with the detection results. For instance, the likelihood value can include a value between zero and one that indicates a confidence level of a classification of a blood vessel as an artery or vein. In some embodiments, the ultrasound machine generates indicators (e.g., outlines, circles, ellipse, boxes, etc.) of blood vessels, and adjusts an opacity of the indicators based on the likelihood value that represents a confidence of the prediction for that blood vessel. This adjustment of opacity results in improvements over conventional ultrasound systems that do not adjust opacity of an indicator based on a confidence level for the indicator. In one example, the clinician or operator of the ultrasound machine is exposed to additional information that is useful for selecting a blood vessel for a medical procedure, such as catheterization. Additionally or alternatively, the opacity adjustment makes the display more visually appealing and less confusing, since based on the changing opacity, blood vessels fade in and out gradually over time, rather than suddenly appearing and disappearing.

In one example, the ultrasound machine tracks blood vessels over multiple frames (e.g., a frame can represent one ultrasound image in a series of ultrasound images). For instance, the ultrasound system can determine blood vessels in one ultrasound image, and track the blood vessels in subsequent ultrasound images in a series of ultrasound images. The tracking can be based on properties of the blood vessels, such as locations of the blood vessels, diameters of the blood vessels, classifications as veins or arteries, combinations thereof, and the like. For example, the ultrasound machine can determine that a blood vessel in a first ultrasound image is the same blood vessel in a second ultrasound image based on one or more of the properties of the blood vessel in the first and second ultrasound images.

In some embodiments, the ultrasound machine determines when blood vessel detection fails and produces hypothetical detection results to display a blood vessel on an ultrasound image. For example, the ultrasound machine can detect a blood vessel in multiple ultrasound images, and then fail to detect the blood vessel in a subsequent ultrasound image (e.g., an ultrasound image that follows the multiple ultrasound images in a video sequence). The ultrasound machine can compare the detection results for the ultrasound images in the video sequence, and declare a detection failure in the subsequent ultrasound image based on the comparison. Based on the detection failure, the ultrasound system can generate a hypothetical detection result, such as, for example, a bounding box, and display the hypothetical detection result in the subsequent ultrasound image to designate the location of the blood vessel, despite that the blood vessel was not detected in the subsequent ultrasound image.

In one example, the ultrasound machine determines a desired entry point for an interventional instrument. The ultrasound machine can then calculate the distance from a transducer face (e.g., an edge of a probe) to the desired entry point, and display an indicator of the distance on a display of the ultrasound machine. For instance, the ultrasound machine can display a message with text that includes the distance, and/or an arrow that indicates a direction to move the probe in accordance with the distance.

Thus, the techniques disclosed herein provide for identifying blood vessels in ultrasound images and displaying the blood vessels in a number of ways to convey useful information to an operator. Accordingly, the ultrasound systems disclosed herein can be suitable for medical procedures in which conventional ultrasound systems are not suitable, since the conventional ultrasound systems can result in undesired consequences for a patient, including discomfort, loss of blood from multiple punctures, risk of infection, and the like.

Note that while the discussion herein focuses on blood vessels, the techniques and systems disclosed herein are not limited to blood vessels and can be used with other body structures, such as nerves, muscles, skeletal parts, and the like. Moreover, while the discussion herein focuses on peripheral intravenous catheterization, the techniques and systems disclosed herein are not limited to catheters, and can be used with any suitable interventional instrument, such as a needle, stint, clamp, guide, etc.

Display Enhancements

The techniques and systems disclosed herein can detect blood vessels in ultrasound images and generate useful information regarding the blood vessels in a variety of ways. In some embodiments, an ultrasound system determines a diameter of a blood vessel based on one or more previous ultrasound images. For instance, the ultrasound system can determine the diameter of a blood vessel in each of multiple previous frames (e.g., previous 2, 3, 4 or more frames), and generate a diameter for the blood vessel in a current frame based on the diameters of the blood vessel from the multiple previous frames. Hence, the ultrasound system can prevent the undesirable fast changing of an indicator of the blood vessel (e.g., a color of a bounding box of the blood vessel that can correspond to a catheter size), which can allow an operator to understand the true size of the blood vessel and take a suitable action, such as selecting the appropriate size of a catheter.

In some embodiments, the ultrasound system generates ultrasound images that include one or more blood vessels, and determines diameters of the blood vessels in the ultrasound images. The diameters can include a respective diameter for each blood vessel in each ultrasound image of the ultrasound images (e.g., an ultrasound video stream). The ultrasound system can include a neural network that determines the sizes and locations of the blood vessels. The neural network can be implemented at least partially in hardware of a computing device (e.g., the ultrasound machine, a computing device coupled to the ultrasound machine, such as a tablet, combinations thereof, and the like). The ultrasound system can calculate a blood vessel diameter based on diameters of a blood vessel. Based on the blood vessel diameters of a same blood vessel in multiple images, the ultrasound system can generate a blood vessel diameter for use in displaying the blood vessel. The ultrasound machine can select a color based on the blood vessel diameter, and then generate an indicator based on the blood vessel diameter and the selected color to provide an indication in at least one ultrasound image, such that the blood vessel is displayed with the indicator having the color. FIGS. 1A-6 illustrate examples of this process.

In an example, the process starts with the processor of the ultrasound machine executing an image analysis algorithm to perform image analysis on ultrasound images, resulting in the detection of a blood vessel in the ultrasound images. The processor can execute two algorithms, one to detect the blood vessel and another to determine the type of the detected blood vessel (e.g., whether the blood vessel is a vein or an artery). The algorithms can include one or more neural networks, such as a first neural network trained to detect a location of a blood vessel, and a second neural network trained to classify the blood vessel as a vein or artery based on the detection results of the first neural network. Alternatively, these two neural networks can be integrated into a single algorithm. In an example, a single neural network comprising a first head of the detection and a second head of the classification is included in a single algorithm, such that the processor includes and can execute the single algorithm.

Figure 1A:
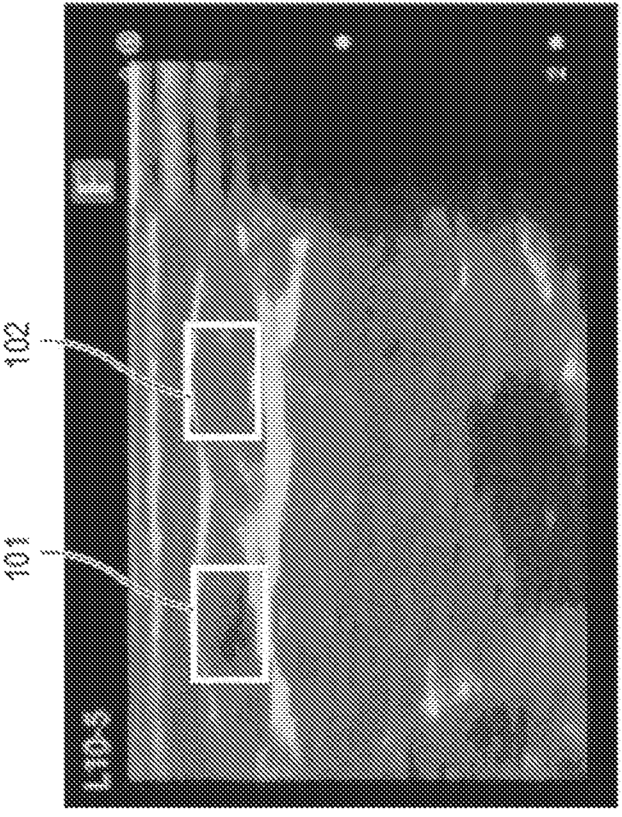

FIG. 1A illustrates an example of detecting two blood vessels and identifying them with boxes 101 and 102, respectively, that have a property, such as a color, line width, line shape (e.g., solid or dashed), etc. The boxes 101 and 102 are examples of bounding containers for the blood vessels in FIG. 1A, and can be generated with a processor in the ultrasound system using information from the neural network. The ultrasound system can then classify the blood vessels as veins or arteries, such as with an additional neural network. After classifying the blood vessels as veins or arteries, the ultrasound system can change a property of one or both of the boxes 101 and 102 to act as an indicator of the classification. In the example in FIG. 1B, after the ultrasound system classifies both blood vessels as veins, the ultrasound machine changes the color of the boxes 101 and 102 in FIG. 1B (represented with hashing) compared to the color of the boxes 101 and 102 in FIG. 1A.

In an example, the ultrasound system determines an outline of a detected blood vessel, and approximates the determined outline as an oval. For instance, the ultrasound system can match an oval to one or both of the boxes 101 and 102. Additionally or alternatively, the ultrasound system can include an implementation of binarizing technology, contour detection technology, or segmentation technology to determine an outline for a blood vessel.

Figure 2B:
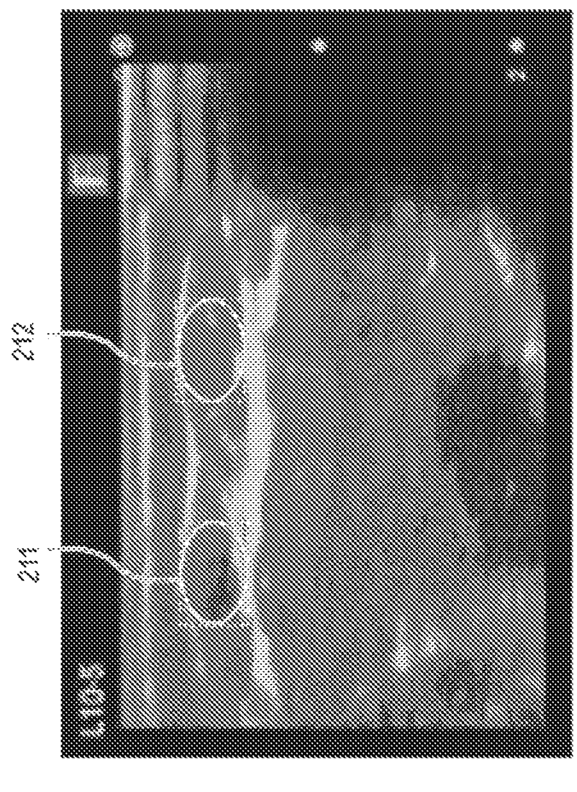
FIGS. 2A and 2B illustrate detecting an outline of a vein.
Figure 2A:
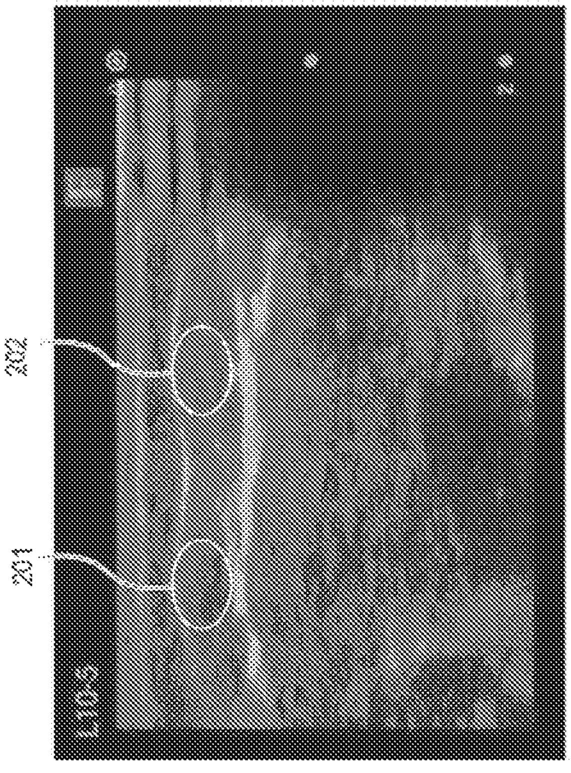

FIGS. 2A and 2B illustrate detecting an outline of a blood vessel (e.g., a vein). Referring to FIG. 2A, two blood vessels 201 and 202 are shown. Contouring by binarization/edge-detection can be performed inside a box-shaped area (not shown) selected in the image of FIG. 2A. Additionally or alternatively, the ultrasound system can match inner ovals 211 and 212 to boxes, as shown in FIG. 2B. In these examples, the ultrasound system produces ovals as bounding containers for the blood vessels (e.g., veins).

Figure 3:
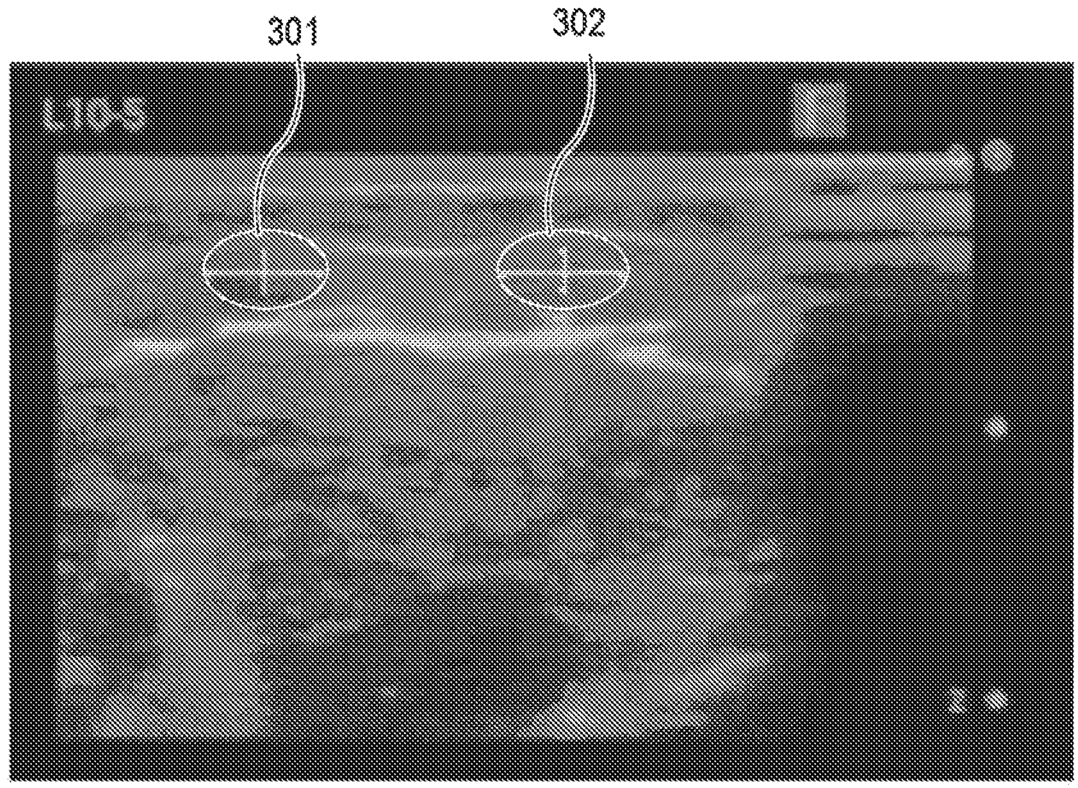
FIG. 3 illustrates an example of an oval with intercrossing diameters.

The ultrasound system can determine diameters of blood vessels using the ovals produced as bounding containers. FIG. 3 depicts a major axis and a minor axis (together major/minor axes 301 and 302 for two blood vessels, respectively). The ultrasound system can determine a diameter of one of the blood vessels from the major/minor axes 301, and a diameter of the other of the blood vessels from the major/minor axes 302. For instance, the ultrasound system can average the major and minor axes of major/minor axes 301 to determine, as a blood vessel diameter, a diameter of the blood vessel on the left side of FIG. 3, and average the major and minor axes of major/minor axes 302 to determine a blood vessel diameter, a diameter of the blood vessel on the right side of FIG. 3. Additionally or alternatively, the ultrasound system can generate a blood vessel diameter, a diameter of a blood vessel from the weighted average of major and minor axes of an oval (e.g., an ellipse) that represents a bounding container for the blood vessel. For instance, the ultrasound system can weigh one of the axes more heavily than the other of the axes when forming an average.

In one example, the ultrasound system determines, as a blood vessel diameter, a diameter of a blood vessel from the major and minor axes of an ellipse by matching a property of the ellipse to a property of a circle. For instance, the ultrasound system can determine the diameter of the blood vessel as a diameter of a circle that has the same area as the ellipse that represents the bounding container of the blood vessel. Let the major and minor axes of the ellipse be $d_1$ and $d_2$, respectively. The ultrasound system can determine the diameter of the blood vessel, d, as the diameter of a circle with a same area as the ellipse, or $$\pi \cdot \left(\frac{d}{2}\right)^2 = \pi \cdot \frac{d_1}{2} \cdot \frac{d_2}{2}.$$

The diameter of the blood vessel can therefore be set according to $$d = \sqrt{d_1 \cdot d_2}.$$

Additionally or alternatively, the ultrasound system can determine, as a blood vessel diameter, the diameter of a blood vessel from a diameter of a circle that has the same circumference as the ellipse that represents the bounding container of the blood vessel. In this example, the ultrasound system can determine the diameter of the blood vessel from $$\pi \cdot d = \pi \cdot \sqrt{2 \cdot \left[\left(\frac{d_1}{2}\right)^2 + \left(\frac{d_2}{2}\right)^2\right]}.$$

Thus, the ultrasound system can set the diameter of the blood vessel according to $$d = \frac{\sqrt{2}}{2} \cdot \sqrt{(d_1)^2 + (d_2)^2}.$$

In some embodiments, the ultrasound system detects an artery, and displays the artery in an enhanced way with an indicator that is different from an indicator used to identify a vein. For example, the indicator used for an artery can be a red circle with a red line across the circle to notify the operator not to select the artery for a procedure in which a vein is desired. In some embodiments, after detection of an artery, the operator of the ultrasound machine may turn off a calculation of the artery diameter, and hence may turn off a calculation of blood vessel diameter of the artery. Additionally or alternatively, the operator may individually (e.g., one after another in succession) enable or disable enhancements of a vein or artery, such as by first disabling a designator of a vein or artery classification, followed by disabling a displayed diameter of the vein or artery.

In some embodiments, the ultrasound system applies tracking technology for a detected blood vessel to determine if the same blood vessel appears in a plurality of ultrasound images. For instance, the tracking technology can use the diameters and the locations of the detected blood vessels. In such a case, the blood vessel diameters are calculated in advance to the tracking. However, in other embodiments, the tracking of detected blood vessels comes before calculating the blood vessel diameters. Note that the blood vessel diameter can be calculated before or after tracking because the blood vessel diameter is calculated based on two inter-crossing diameters, and the tracking only requires at least calculating these two diameters and does not necessarily require blood vessel diameter.

Figures 4A, 4B, 5A, 5B:
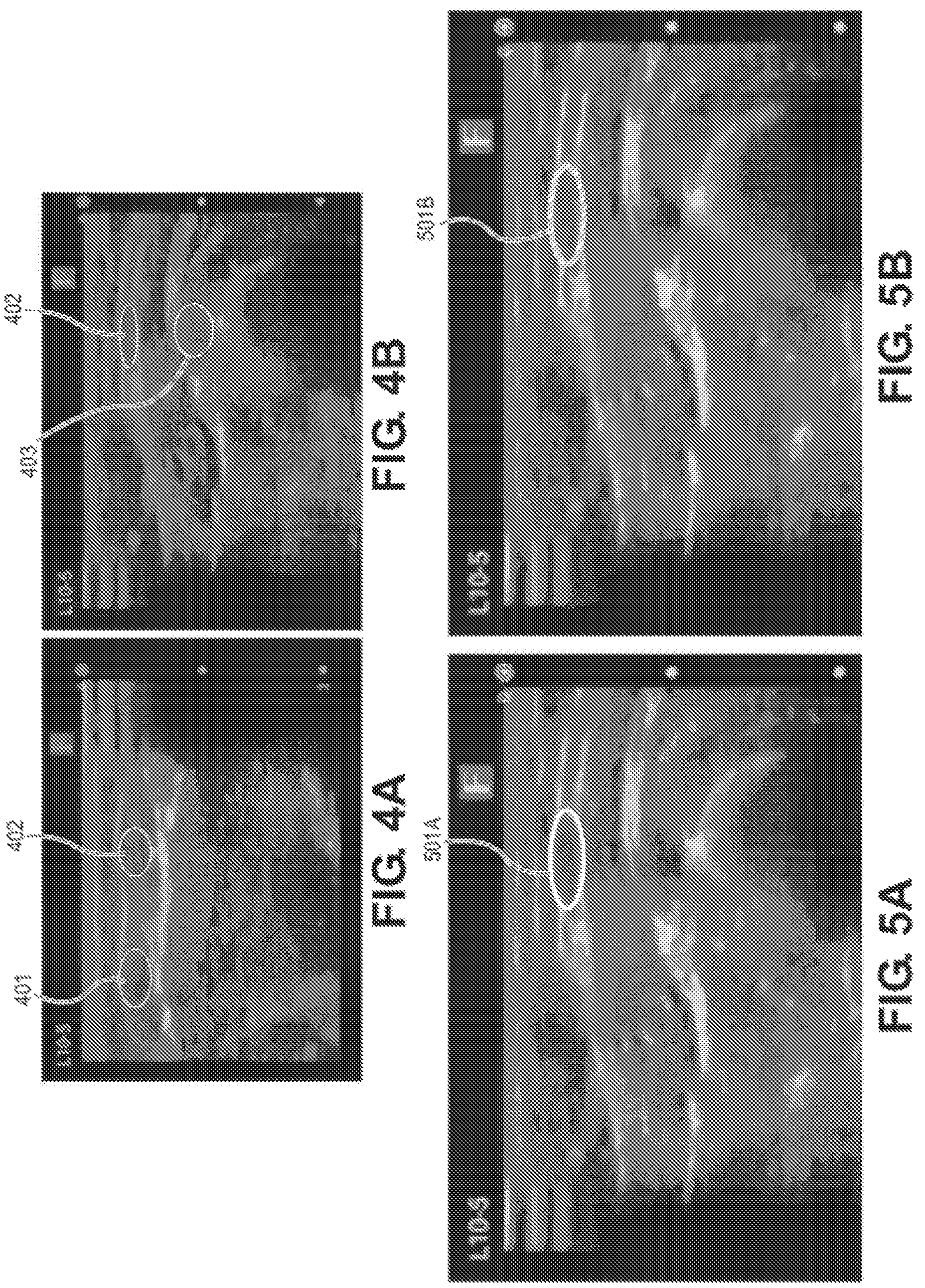
FIGS. 4A and 4B represent one image without probe pressure (compression) applied and one with probe pressure (compression) applied.
FIGS. 5A and 5B illustrate enhancement on a detected vein.

The use of tracking technology also enables calculating a current diameter value of a blood vessel from previously-determined diameters for the blood vessel. For example, the ultrasound system can set the current blood vessel diameter of a blood vessel to a maximum value of previously-determined blood vessel diameters for the blood vessel as it appeared in multiple previous ultrasound images, such as from the previous three to five images. As the tracking technology enables determination of the same blood vessels that persist through a series of ultrasound images (frames) (e.g., an ultrasound), in some embodiments, the maximum value is calculated for the same blood vessel. FIGS. 4A and 4B represent two images during the pressure of a probe in a time series. There are two veins in FIG. 4A, vein 401 and vein 402. Due to the pressure by the probe, vein 401 disappears in FIG. 4B, so that the ultrasound system identifies only the vein 402 as the same vein between FIG. 4A and FIG. 4B. Hence, the ultrasound system can determine a current value of the blood vessel diameter of vein 402 in FIG. 4B from one or more values of the blood vessel diameter of the identified vein 402 in a predetermined number of previous images including FIG. 4A. For instance, if the blood vessel diameter of the vein 402 in FIG. 4B is 1.5 mm and the maximum blood vessel diameter of the vein 402 in a previous image (e.g., FIG. 4A) is 2.0 mm, then the ultrasound system can set the current diameter of the vein 402 in FIG. 4B as 2.0 mm. A new vein 403 is also shown in FIG. 4B and does not appear in FIG. 4A. Hence, the ultrasound system can determine a blood vessel diameter of the vein 403 from FIG. 4B, without using blood vessel diameters of the vein 403 in previous images.

In some embodiments, the tracking uses at least one or more types of information related to: a point, a line, or an area of a blood vessel region. For example, in some embodiments, a point of a blood vessel is tracked between frames, and the ultrasound system measures movement of the point. In the case of a point, the information related to the point may include a center, a top, a bottom, a left, a right, or a centroid point of a blood vessel region, and the difference in location of the same point between two ultrasound images is evaluated. Information other than point information may be used in tracking. Examples of other information that may be used for tracking include information related to a line (e.g., diameter, or a length of an outline of a blood vessel region, etc.) and information related to an area (e.g., a shape, an area, or illumination information (texture information) of a blood vessel region, etc.). If the movement is within a threshold distance (e.g., less than 2 mm), then the ultrasound system regards the blood vessels of the frames as the same blood vessel. In some embodiments, the threshold distance is equal to a percentage (e.g., one-half) of the diameter of the blood vessel in the immediately preceding frame (or another previously-generated frame), or a blood vessel diameter (e.g., an average of the diameters) of the blood vessel in a set of two or more previously-generated and consecutive frames.

In some embodiments, the ultrasound system displays a detected blood vessel superimposed with an enhancement, such as a color-enhancement. The ultrasound system can determine the color for the color enhancement according to the diameter value determined by the ultrasound system for the blood vessel. FIGS. 5A and 5B illustrate the same ultrasound image with different color enhancement on a detected vein on a display of the ultrasound system. The image was obtained under the pressure by a probe, for one example. Specifically, FIG. 5A illustrates a display of the detected vein when taking into consideration only the blood vessel diameter of the current image, while FIG. 5B illustrates the detected vein with color enhancement according to calculated blood vessel diameter according to some embodiments. Suppose that (i) the calculated blood vessel diameter of the veins 501A and 501B are 1.5 mm, and that (ii) the configuration of the enhancement rule in the ultrasound system is such that, if a current value of a blood vessel diameter is equal to or above 2.0 mm, a vein is circled with a color (e.g., pink), and if that value is below 2.0 mm, the vein is circled with another color (e.g., orange). In FIG. 5A, the vein 501A is enhanced with the color orange (represented by a solid white ellipse), whereas in FIG. 5B, the vein 501B is enhanced with color pink (represented by hatching). The reason why the vein 501B is circled with the color pink is that, in one embodiment the ultrasound system is configured to calculate a blood vessel diameter from the previous images that include the maximum value of the blood vessel diameter, 2.0 mm. In such an image that includes the maximum blood vessel diameter, the shape of the same vein as of 501A and 501B would be more circular, for example. Therefore, the enhancement display of FIG. 5B corresponds to a change of the shape of the blood vessel better than that of FIG. 5A. In other words, such an embodiment as FIG. 5B is effective, for example, in a case where the probe releases and/or compresses the object under ultrasonic scan such that the shape of the vessel changes gradually or abruptly.

In some embodiments, the ultrasound system uses past images (e.g., previously generated and displayed ultrasound images) to determine a property of a blood vessel, such as a vein size. By using past images, the ultrasound system can determine when a blood vessel is in a normal state (e.g., not compressed by a probe). For instance, the ultrasound system can determine an image that contains a blood vessel having its maximum diameter from multiple ultrasound images, and use the maximum diameter to determine the blood vessel diameter, thus enabling selection of the blood vessel at its correct size when determining its blood vessel diameter. Additionally or alternatively, at least three past frames or at least one second worth of frames can be used to determine when the blood vessel is at its correct size. Note that more or less than these numbers of frames can be used. Thus, the ultrasound system can determine the real (or true) value of a blood vessel diameter in its normal state, and hence select the correct color (e.g., pink, according to the diameter) to designate the blood vessel. In this manner, it is possible to mitigate the effect of pressure by the probe.

Figure 6:
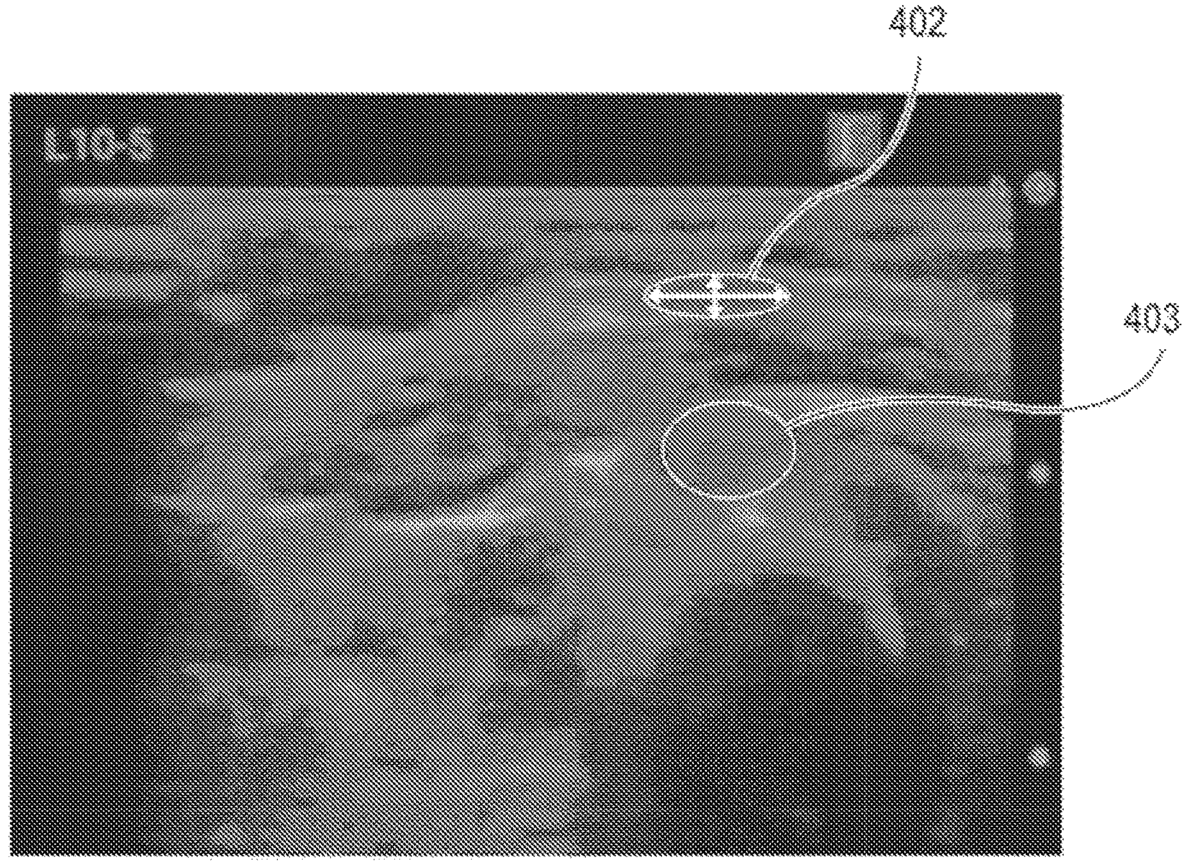
FIG. 6 illustrates an example of vein diameters used for calculation.

In some embodiments, the blood vessel diameters are calculated for the subsequent images (frames). In one example, the ultrasound system can detect veins and perform the calculation of the blood vessel diameters only of the veins for the subsequent images (frames), and then display enhancements only for the veins, thus encouraging the understanding the properties of the blood vessels in ultrasound images. FIG. 6 illustrates an example of blood vessel diameters used for calculation. Referring to FIG. 6, the ultrasound system identifies veins and calculates diameters for vein 402 for one frame (image) using the axes that are shown. Artery 403 has a diameter, and the blood vessel diameters of vein 402 and artery 403 are not calculated for subsequent frames.

Figure 7:
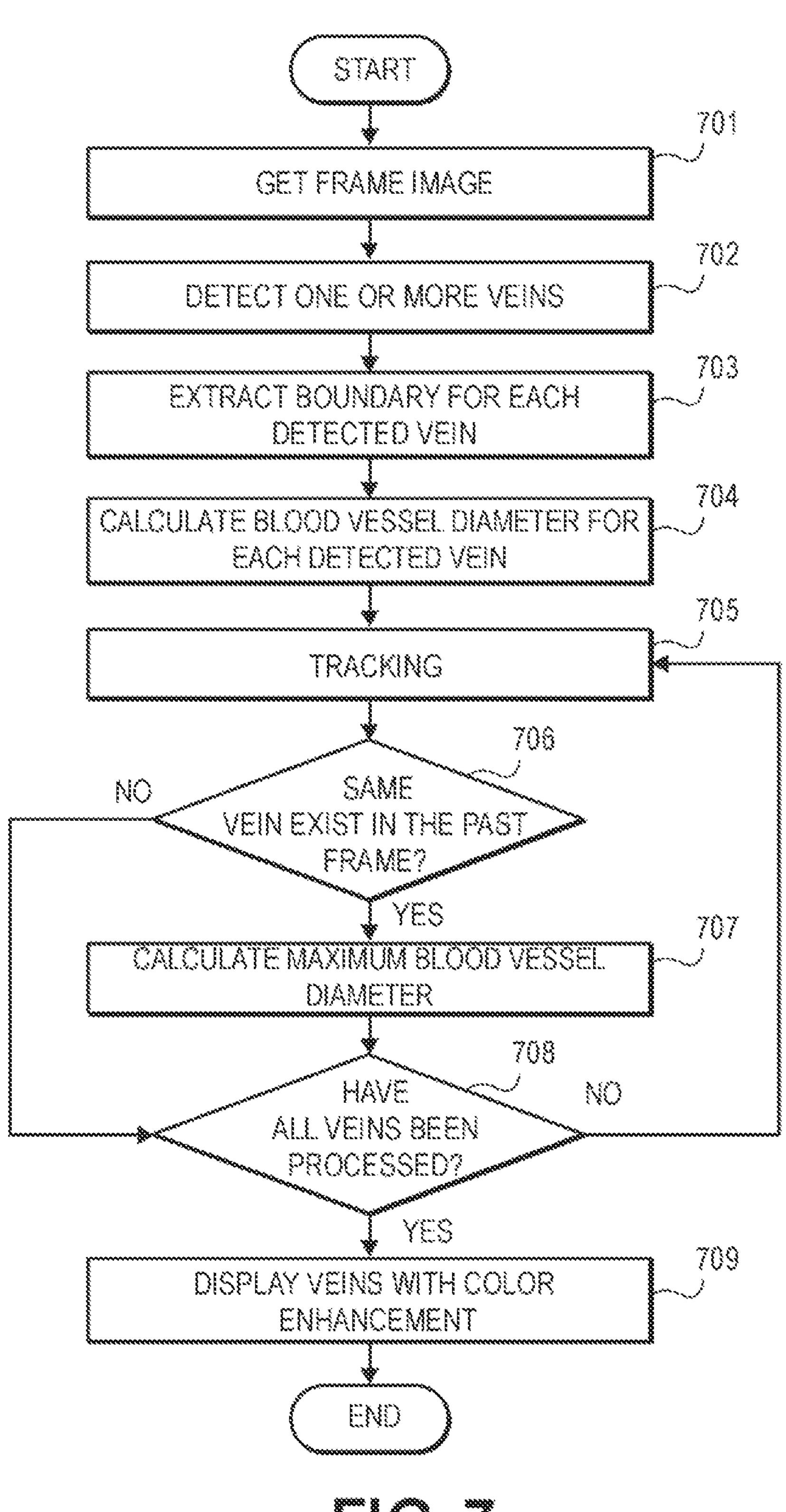
FIG. 7 illustrates a flow diagram of one embodiment of a process for displaying veins on an ultrasound image.

FIG. 7 illustrates a flow diagram of one embodiment of a process for displaying veins on an ultrasound image. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by a processor of an ultrasound machine. Although FIG. 7 illustrates displaying veins on an ultrasound image, the process can additionally or alternatively be used for displaying arteries.

Referring to FIG. 7, the process begins by processing logic obtaining an image frame, such as an ultrasound image, (processing block 701) and performing vein (or blood vessel) detection on the image frame (processing block 702). Using the results of vein detection, the processing logic extracts the boundaries of veins (processing block 703) and calculates the blood vessel diameters of detected veins (processing block 704).

After calculating blood vessel diameters, processing logic performs tracking (processing block 705). During tracking, processing logic determines whether each individual detected vein exists in a past frame (processing block 706). If not, the process transitions to processing block 708. If so, processing logic calculates the maximum blood vessel diameter of that vein based on its blood vessel diameters in previous frames (processing block 707) as a current value of the blood vessel diameter and transitions to processing block 708.

At processing block 708, processing logic determines whether all the veins have been tracked and whether the maximum blood vessel diameters have been calculated for those veins being tracked. If not, the process transitions back to processing block 705 where the process continues. If so, the process transitions to processing block 709 where processing logic displays each of the veins in an ultrasound image with a color or other indicator selected based on its maximum diameter.

In some embodiments, the current value of the blood vessel diameter is calculated in one of a number of different ways. For example, the current value of the blood vessel diameter of a detected blood vessel can be determined from the maximum, minimum, average, median, mode, standard deviation, or a max-min value from the blood vessel diameters of the same vein in the past several frames. In some embodiments, the ultrasound machine determines the calculation algorithm in advance of an examination, or before imaging the blood vessel or using any enhancement of the blood vessel in the image (e.g., indicator, color, etc.). This determination can be part of a configuration or boot-up process of the ultrasound machine. In some embodiments, the calculation algorithm (e.g., maximum, minimum, average, etc.) is selected by the operator of the ultrasound machine.

One benefit of choosing standard deviation or a max-min value is that a normal vein can compress and recover easily during the pressure by the probe, and if a vein is not in a healthy condition, it is not so elastic. One benefit of choosing the average, median, or mode value is that it results in the exclusion of an extraordinary value that unintentionally or erroneously appears during one or more frames. Another benefit of choosing the average, median, or mode value is a compromise between the two points: (i) a smaller gauge catheter would cause less damage to the blood vessel, but (ii) a smaller gauge catheter would also transport less liquid. Moreover, since average, median, and mode values are always less than the maximum value of the blood vessel, a medical instrument/tool, such as, for example, but not limited to, needle or catheter, is smaller than the diameter of the blood vessel.

In an example, the processor is configured to determine the calculation algorithm automatically (e.g., without explicit user selection of the calculation algorithm). In some embodiments, the selection is based on whether the probe is pressing into a subject being examined (as determined, for example, by a pressure sensor in the probe), thereby reducing the size of the blood vessel. In one such embodiment, (i) if the probe is pressing on the same part of the object, the processor chooses the maximum calculation algorithm, and (ii) if the probe is moving along the blood vessel (e.g., the longitudinal direction), the processor chooses the average calculation algorithm. In some embodiments, to distinguish between (i) and (ii), the ultrasound machine performs image analysis to determine whether the periphery of the detected blood vessels has changed or not. Additionally or alternatively, a location sensor (e.g., magnetic sensor, an accelerometer, a gyro sensor, etc.) inside the probe can be used to distinguish between (i) and (ii).

In some embodiments, the ultrasound machine marks the displayed blood vessels with a colored indicator (e.g., a circle, an ellipse, etc.). In such a case, in some embodiments, the color can be based on whether the detected blood vessel is an artery or a vein. For instance, the ultrasound machine can mark an artery with a red indicator (e.g., a red circle, or a crossed-out circle icon). Additionally or alternatively, the ultrasound system can mark a blood vessel with an indicator having a color based on which size (e.g., gauge) of needle or catheter could be inserted into the blood vessel. The color can be in accordance with a standard color chart that assigns unique colors to instrument gauges. Thus, in some embodiments, blood vessels having different ranges of diameters (e.g., blood vessel diameters) are enhanced by using different colors. Furthermore, in one example, only veins having different ranges of diameters (e.g. blood vessel diameters) are enhanced by using colors that are different from the color of enhancement used for arteries, since in one configuration of the ultrasound system blood vessel diameters are calculated only for veins.

As discussed above, in some embodiments, the ultrasound machine detects and displays some enhancement on blood vessels irrespective of which blood vessels are of interest to an operator of the ultrasound machine. For instance, the display of enhancements on blood vessels can include one or more enhanced blood vessels that an operator has a desire to see along with one or more other enhanced blood vessels in which the operator has expressed no interest in viewing. The operator can input a desire to view or not view a particular blood vessel via a user interface of the ultrasound machine.

In some embodiments, the operator is able to remove enhancements on unwanted blood vessels from the display. For example, the operator may select a detected blood vessel to cause the enhancements on the detected blood vessel to switch between an ON-state in which the blood vessel is displayed with enhancements (e.g., a bounding container, a color, a color based on type (e.g., vein or artery), a color based on the size of a needle that is insertable into the blood vessel, text indicating a diameter, an icon, such as a stop sign, thumbs up, or thumbs down, combinations thereof, etc.) and an OFF-state in which the detected blood vessel is displayed without any enhancements.

Figures 8A, 8B, 8C, 8D:
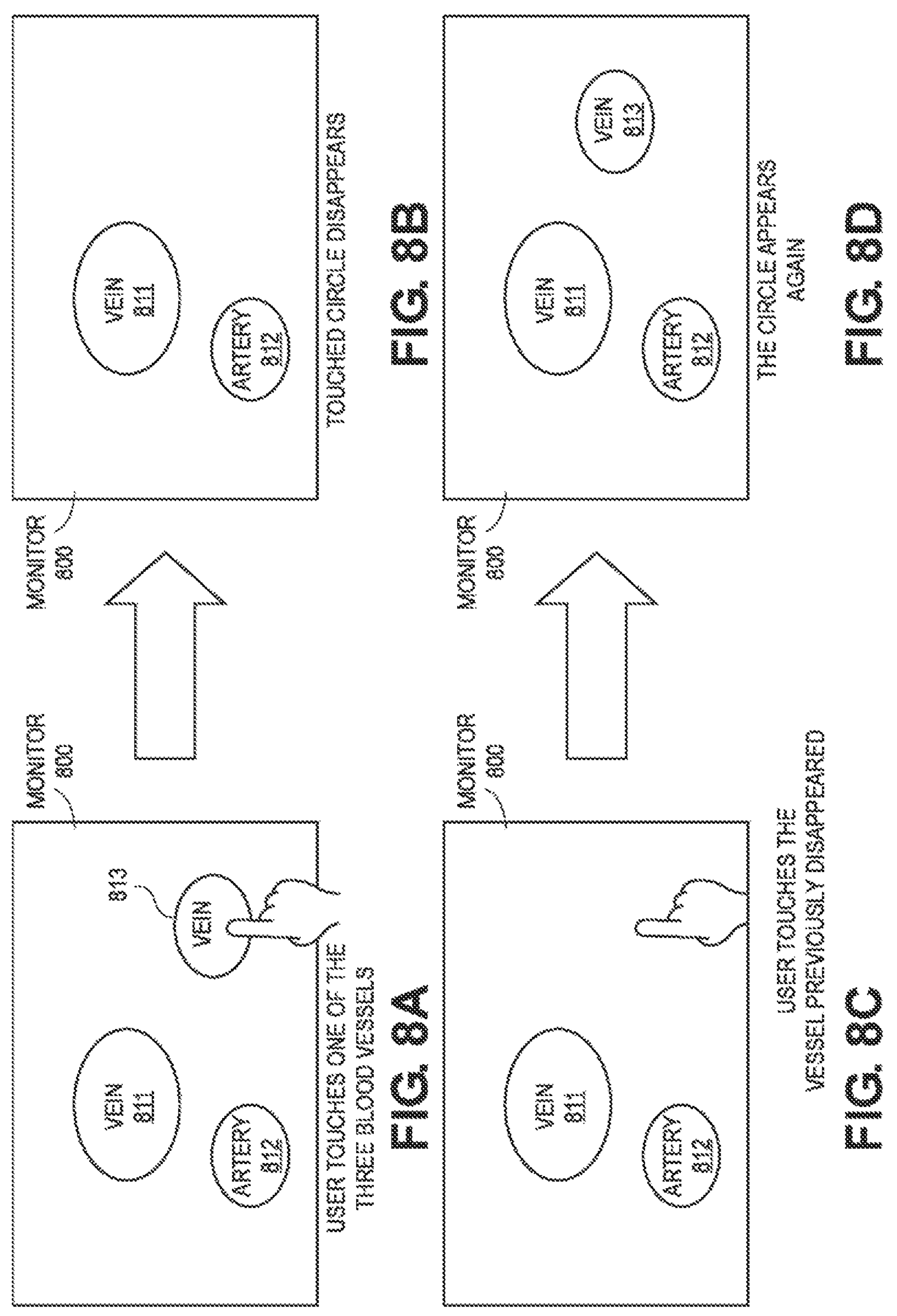
FIGS. 8A-8D illustrate an example of a process for displaying blood vessels.

FIGS. 8A-8D illustrate an example of a process for displaying enhancements on blood vessels. Referring to FIG. 8A, blood vessels that include vein 811, artery 812, and vein 813 are shown and enhanced on monitor 800. In some embodiments, monitor 800 includes a touch-sensitive screen type display or touch surface display device. In an example, the three blood vessels 811-813 are detected by artificial intelligence (AI). Additionally or alternatively, the detected blood vessels can be marked with a colored indicator (e.g., circle or ellipse) by AI. If the operator touches monitor 800 at the location of one of the three blood vessels, such as vein 813, in FIG. 8A, the colored circle disappears as shown in FIG. 8B. Moreover, as shown in FIG. 8C, if the operator touches monitor 800 at the location of the one blood vessel that was previously touched to make the circle disappear, the circle appears on the blood vessel again as shown in FIG. 8D.

Figure 9:
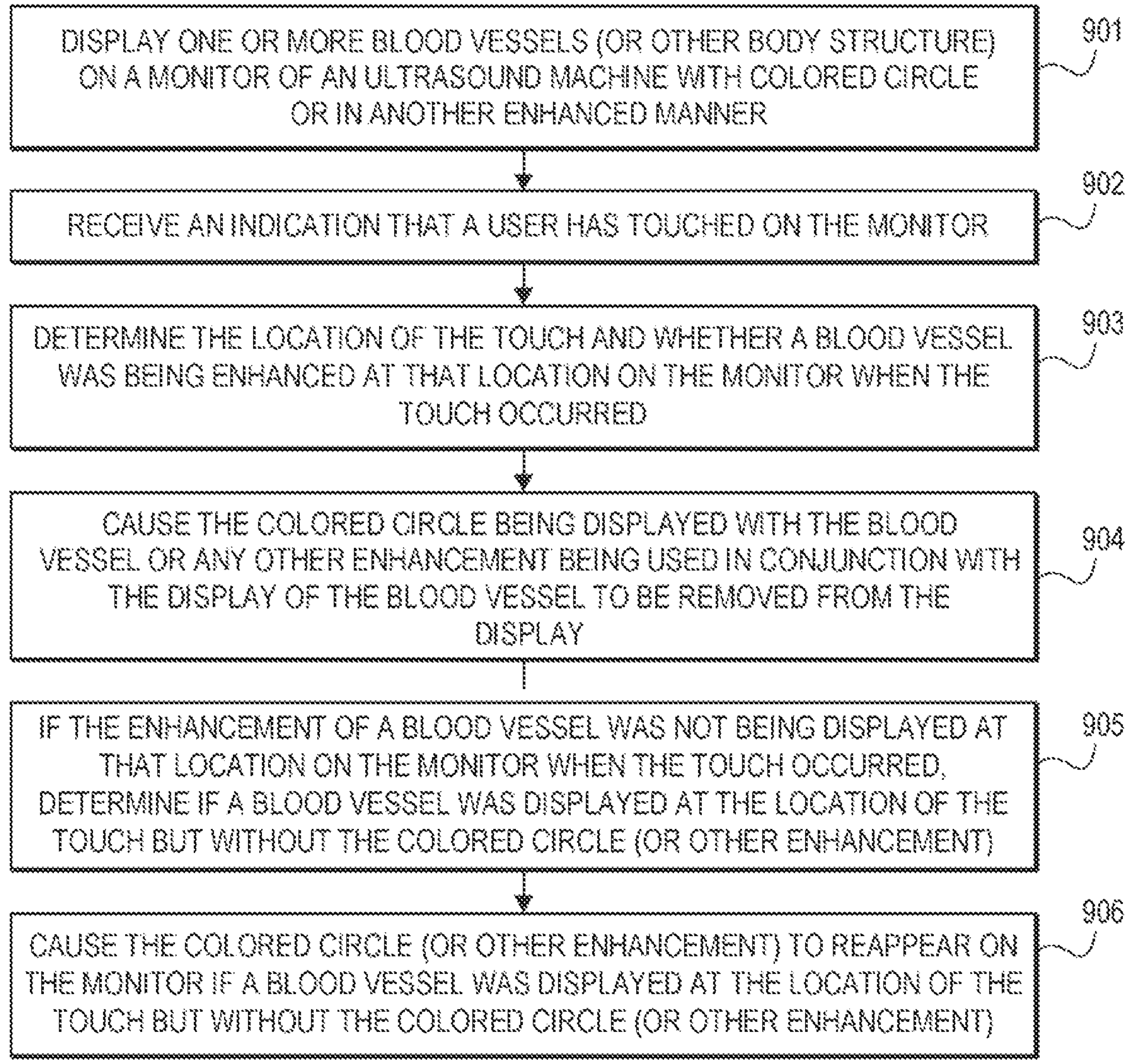
FIG. 9 illustrates a flow diagram of one embodiment of a process for manipulating a display of blood vessels (or other body structure) on a monitor.

FIG. 9 illustrates a flow diagram of one embodiment of a process for manipulating an enhanced display of blood vessels (or other body structure) on a monitor. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by a processor of an ultrasound machine.

Referring to FIG. 9, the process begins by processing logic displaying enhancements on one or more blood vessels (or other body structure) on a monitor of an ultrasound machine with colored circle (or with another indication of other enhanced manner) (processing block 901). In some embodiments, the monitor is a touch-sensitive screen type monitor or touch surface display device.

After one or more blood vessels are displayed in an enhanced manner, processing logic receives an indication that a user has touched on the monitor (processing block 902). Additionally or alternatively, the user could make a selection on the monitor by moving a cursor with a cursor control device to a location on the monitor and pressing a selection button.

In response to receiving the indication that the user has touched the monitor, processing logic determines the location of the touch and whether a blood vessel was being enhanced at that location on the monitor when the touch occurred (processing block 903). If so, processing logic causes the colored circle being displayed with the blood vessel (or any other indicator/enhancement being used in conjunction with the display of the blood vessel) to be removed from the display (processing block 904).

If a blood vessel was not being displayed at that location on the monitor when the touch occurred, processing logic determines if a blood vessel is being detected at the location of the touch but its enhancement is being suppressed from the display (processing block 905), and if so, causes the colored circle (or other indicia/enhancement) to reappear on the monitor (processing block 906).

In some embodiments, the process of FIG. 9 can repeat as blood vessels are displayed on the monitor and the operator touches the monitor. For instance, as an operator moves the ultrasound probe, new blood vessels can appear and previous blood vessels can disappear from view. The ultrasound machine can repeat the process of FIG. 9 for the newly-displayed blood vessels when the operator touches the monitor. In one exemplary implementation of an ultrasound system, the ultrasound system generates ultrasound images continuously and continues the detection process of blood vessels and the tracking technology (and additionally the calculation of the blood vessel diameter) on the generated images regardless of the ON-state or OFF-state of the enhancement, such that if an operator touches a blood vessel that was not previously enhanced on the monitor, a circle with an appropriate color is displayed at the blood vessel, wherein the color is additionally based on the calculated blood vessel diameter and/or the standard color corresponding to a catheter size.

In some embodiments, the enhancement to the ultrasound images comes in the form of indicating a blood vessel that was not detected. For example, if blood vessels are detected in an ultrasound image, some abrupt change in the examination circumstance can cause the detection results (e.g., a colored circle on a detected blood vessel of an ultrasound image) to disappear suddenly. For instance, if a probe is suddenly pressed into the subject under examination the blood vessel of an ultrasound image can suddenly collapse, which can cause no detection result to be displayed on the monitor. This lack of detection display can be troubling to a user, because the user may still see the actual location of the collapsed blood vessel in a B-mode image.

In some embodiments, if the processing logic of the ultrasound machine fails to detect a blood vessel in a current image, the detection results of one or several previous ultrasound images are searched. The processing logic can determine a hypothetical detection result based on the detection results of one or more of those previous ultrasound images, and the hypothetical detection result can be superimposed on the current image and displayed by the ultrasound machine. In one embodiment, the ultrasound machine only displays the hypothetical detection results for two to three frames to prevent flickering.

In some embodiments, the ultrasound machine determines diameters and locations of the blood vessels in a subset of the ultrasound images. As discussed above, this determination can be made using a neural network or other detection mechanism implemented at least partially in hardware of a computing device, such as the ultrasound machine itself, a computing device coupled to the ultrasound machine, or combinations thereof. Alternatively or additionally, the determination can be made using hardware (e.g., circuitry, dedicated logic, etc.), software (such as is run on a general-purpose computer system or a dedicated machine), firmware (e.g., software programmed into a read-only memory), or combinations thereof.

Based on the diameters and locations of blood vessels that are found in each of the images, the ultrasound machine is able to determine whether a detection failure for one of the blood vessels in one of the ultrasound images occurred because the blood vessel was absent from those blood vessels identified by the neural network (or other detection mechanism). In response to that determination, the ultrasound machine can attempt to track the previously detected blood vessel by alternative means and display an indicator of the diameter and the location of the one of the blood vessels in one of the ultrasound images. In some embodiments, the indicator is based on the diameters and the locations determined by the neural network for the subset of the ultrasound images.

Figures 10A, 10B, 10C:
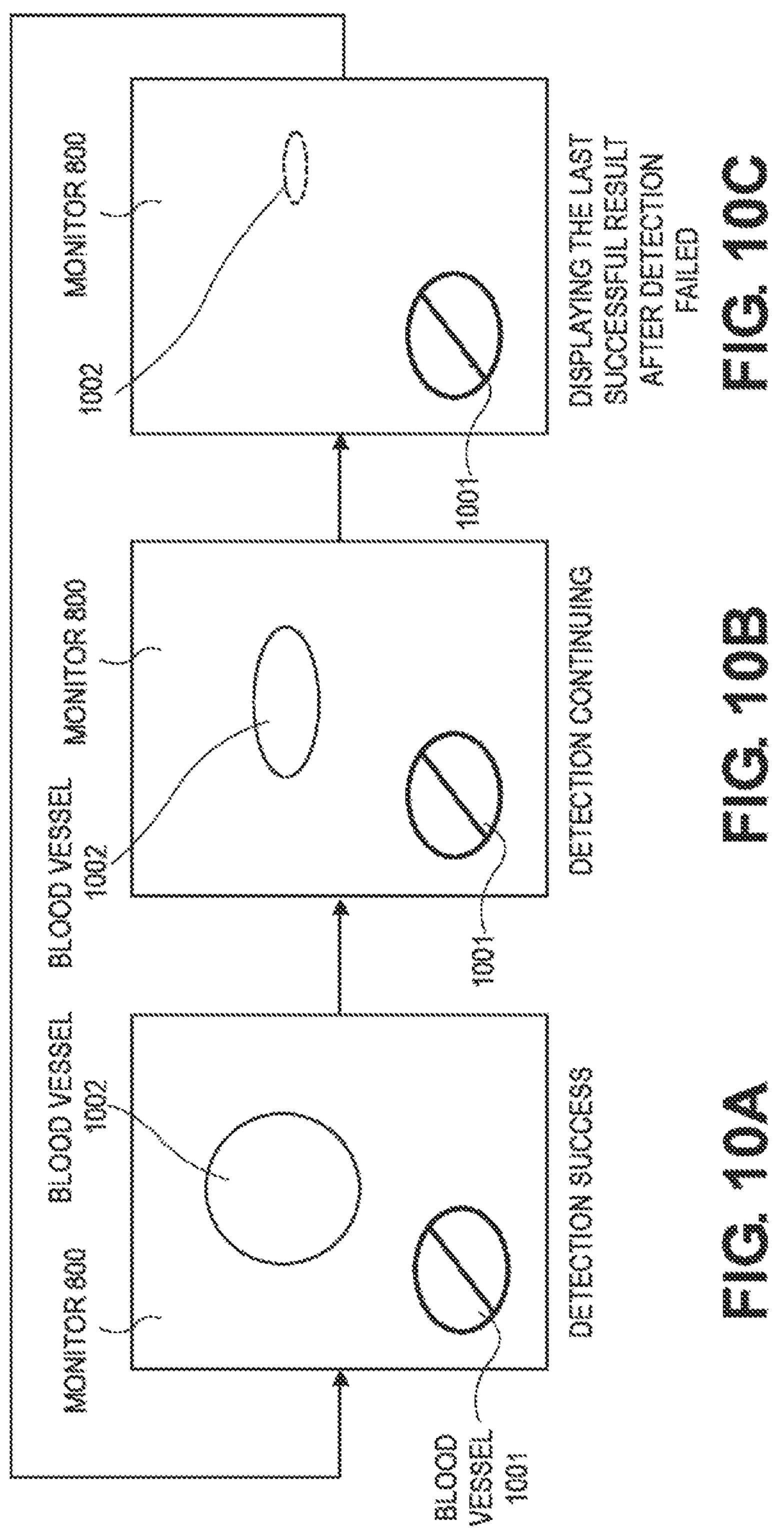
FIGS. 10A-10C illustrate one embodiment of a process of displaying an image of a previous detection result in response to the sudden disappearance of the detection result.

FIGS. 10A-10C illustrate one embodiment of the process of displaying an image of a previous detection result in response to a sudden disappearance of a detection result. This situation may occur when the probe is compressing gradually, for instance. As a blood vessel is compressed further, the shape of the blood vessel becomes collapsed. In such a case, the detection of such a collapsed blood vessel only from the current image becomes much more difficult.

Referring to FIG. 10A, blood vessels 1001 and 1002 are displayed on monitor 800 as a result of the detection process determining their presence. As shown in FIG. 10B, while detection continues, blood vessels 1001 and 1002 continue to be displayed on monitor 800, but blood vessel 1002 is shown with an elliptical shape (as opposed to the circular shape of blood vessel 1002 in FIG. 10A). FIG. 10C illustrates that detection only shows blood vessel 1001 being displayed, as blood vessel 1002 is not being displayed. In other words, FIG. 10C reflects the result of the last successful detection of the blood vessel 1002. For example, the ultrasound machine can fail to detect the blood vessel 1002 in FIG. 10C. In such a case, the system displays blood vessel 1002 as a dashed-line ellipse, which represents a hypothetical detection result, even though the detection process did not produce a result for blood vessel 1002. An advantage of displaying the hypothetical result in the same shape as, but with different types of outline from, the successful result (e.g., solid-line ellipse vs. dashed-line ellipse, or solid box vs. dashed box) is to prevent an operator from feeling uncomfortable. In some embodiments, the color of solid-line (actual) and dashed-line (hypothetical) ellipse can be selected from the calculated result of blood vessel diameters in previous images. Since a current value of the blood vessel diameter is calculated based on those of previous images, the fluctuation of color can be suppressed and only the line of the shape is changed, which makes it easier for an operator to identify the same blood vessel (vein).

More specifically, in some embodiments, the hypothetical detection result is displayed in a manner different from that of the actual detection result. As shown in FIG. 10C, for example, the hypothetical detection result is displayed in a dashed-line ellipse, while the actual detection result would be displayed in a solid-line bounding container, such as is shown for blood vessel 1002 in FIG. 10A and FIG. 10B. Additionally or alternatively, different colors, different types of filling for the bounding container, colors, labels, icons, text, or other types of distinguishing features may be used to distinguish actual detection results from hypothetical detection results. Note also that since blood vessel 1001 is an artery, its shape does not change so much as a vein's shape changes.

Figures 11A, 11B, 11C, 11D:
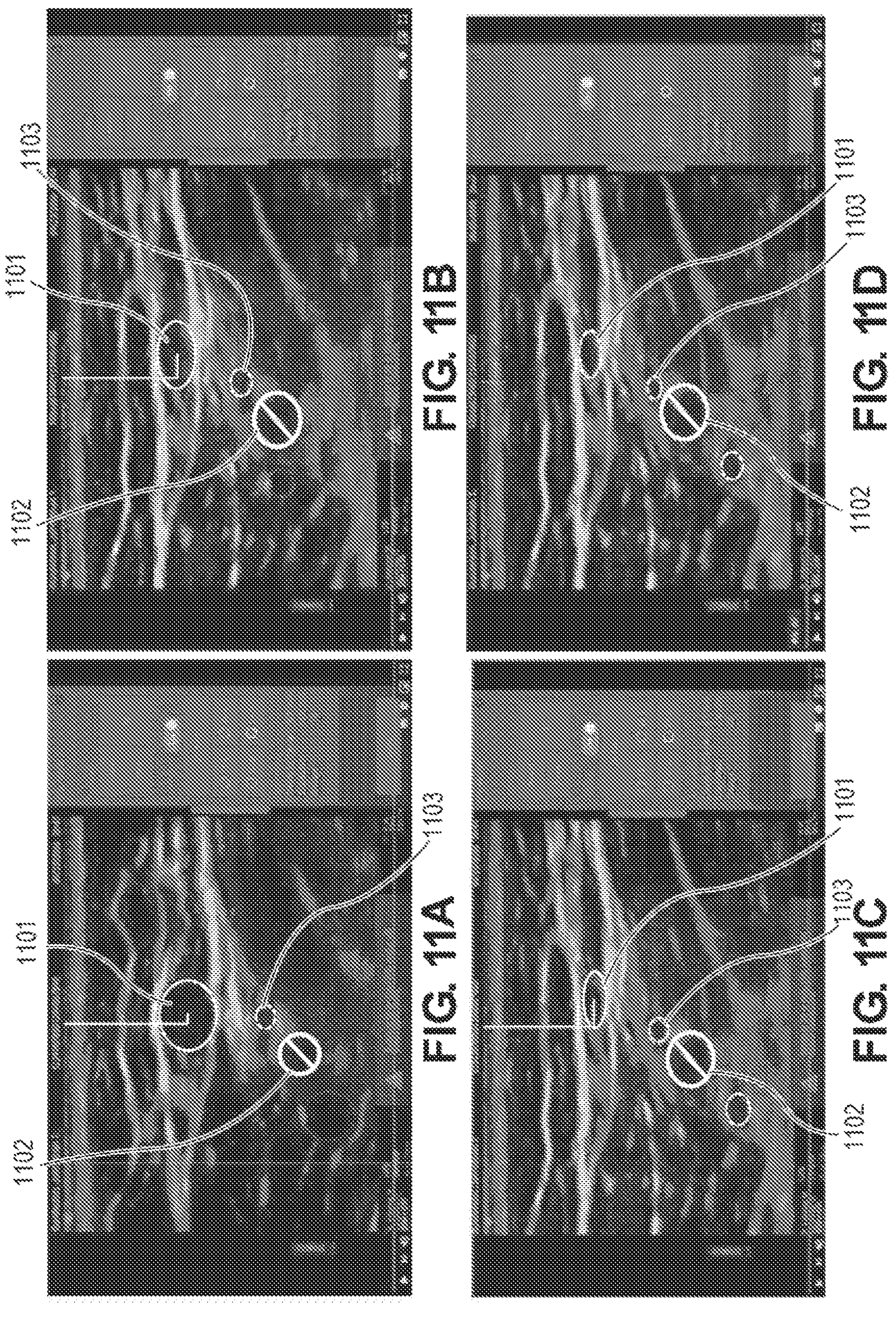
FIGS. 11A-D illustrate an example of an enhanced display of an ultrasound image produced when a probe is in motion.

FIGS. 11A-11D illustrate an example of an enhanced display of an ultrasound image produced when a probe is in motion. Referring to FIG. 11A, blood vessels 1101-1103 are shown on the ultrasound image. Blood vessel 1101 is depicted as a vein with a first colored circle, blood vessel 1102 is depicted as an artery, and blood vessel 1103 is not identified as either a vein or an artery (e.g., identified with a dotted circle). FIG. 11B shows another ultrasound image of the same location where the shape of blood vessel 1101 is represented in a more oval shape with a different enhancement (e.g., a different color) than that of FIG. 11A. The shape of blood vessel 1101 may be due to the operator pressing the probe more into the body at the location. FIG. 11C shows another ultrasound image of the same location where the shape of blood vessel 1101 is represented in a smaller oval shape with a different enhancement (e.g., a different color) than that of FIG. 11B. FIG. 11D shows another ultrasound image of the same location where the shape of blood vessel 1101 is represented in an even smaller oval shape with a different enhancement (e.g., a different color) than that of FIG. 11C and with dotted lines. Accordingly, FIGS. 11A-11D illustrate how enhancements for blood vessels can change due to the motion and/or pressure of a probe.

Figure 12:
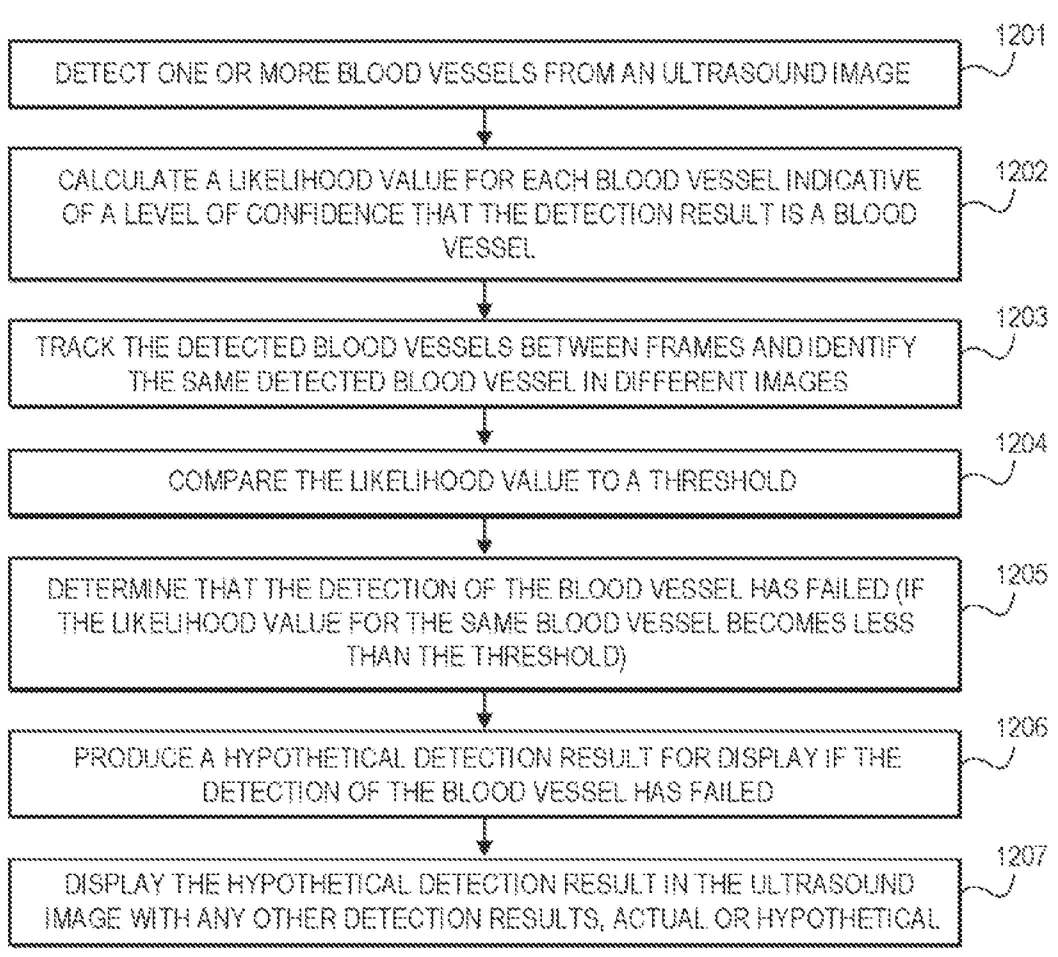
FIG. 12 illustrates a flow diagram of one embodiment of a process for displaying one or more blood vessels (or other body structure) as detection results on a monitor with at least one hypothetical detection result.
Figures 13A, 13B, 13C, 13D, 14A, 14B, 14C, 14D:
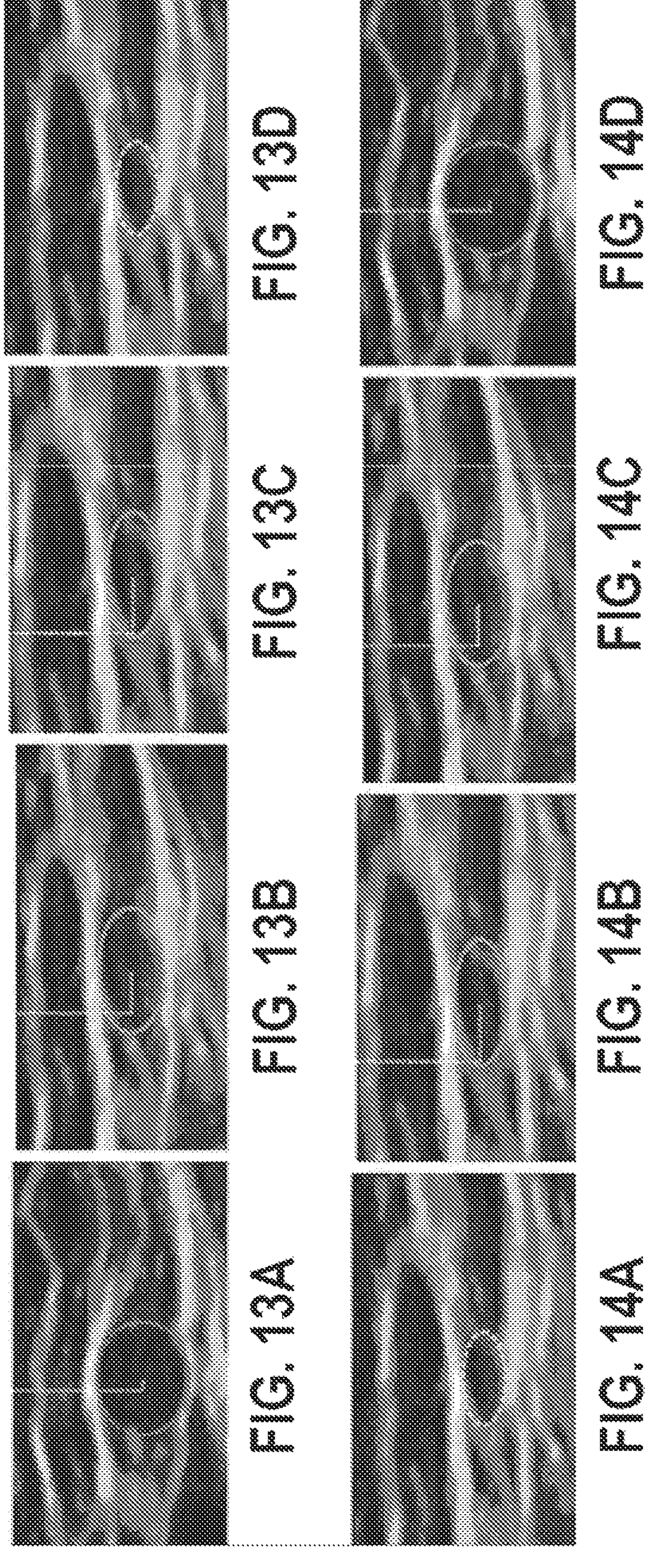
FIGS. 13A-13D illustrate a period during which the pressure by the probe decreases from the certain level to the released state and the shape of a blood vessel changes from another shape back to the normal shape.
FIGS. 14A-14D illustrate the period (ii) during which the compression by the probe decreases from the certain level to the released state and the shape of a blood vessel changes from the additional shape back to the normal shape.

FIG. 12 illustrates a flow diagram of one embodiment of a process for displaying one or more blood vessels (or other body structure) as detection results on a monitor with at least one hypothetical detection result. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by a processor of an ultrasound machine.

Referring to FIG. 12, the process begins by processing logic detecting one or more blood vessels from an ultrasound image (processing block 1201). In some embodiments, the processing logic detects blood vessels using a neural network, template matching, machine-learning (e.g., adaboost, deep-learning, SVM, sequence models including RNN, GRU, ConvGRU, LSTM, etc., to process frame information in sequence, etc.), and others. Additionally or alternatively, processing logic can calculate a likelihood value for each blood vessel indicative of a level of confidence that the detection result is a blood vessel (processing block 1202). The likelihood value can be between zero and one, with one representing high confidence in the detection result, and zero representing low confidence in the detection result.

Processing logic also tracks the detected blood vessels between frames and identifies the same detected blood vessel in different images (processing block 1203). In some embodiments, the processing logic uses location information and/or the type of blood vessel for the tracking and/or identification process.

Processing logic compares the likelihood value to a threshold, such as 0.7 (processing block 1204). If processing logic determines that the likelihood value for the same blood vessel becomes less than the threshold, the processing logic determines that the detection of the blood vessel is failed (processing block 1205) and produces a hypothetical detection result for display (processing block 1206). In some embodiments, to produce the hypothetical detection result, processing logic searches for the result of one or plural previous ultrasound images and uses that result as the basis for the display of the hypothetical detection result. The hypothetical detection result can be calculated using a calculation method (algorithm) performed in a number of ways. In some embodiments, processing logic obtains the most recent, successful detection result and uses that for the hypothetical detection result. Additionally or alternatively, the processing logic can select a detection result with the highest likelihood value from a predetermined number of previous frames as the hypothetical detection result, such as from the previous two, three, four, or more frames. The number of frames may depend at least partially on the acquisition frame rate; a higher frame rate may enable more frames to be selected. In an example, processing logic estimates the shape and/or the location of the blood vessel based on the result of one or more previous frames generated during a predetermined time length in the past, such as from the previous 500 msec of image frames. In an example, this estimation is done by employing motion-vector technology. Additionally or alternatively, this estimation can be done by employing optical-flow technology. Thereafter, processing logic displays the hypothetical detection result in the ultrasound image with any other detection results, actual or hypothetical (processing block 1207).

In some embodiments, the probe of the ultrasound machine has a sensor to detect its motion. If the movement of the probe is above a certain velocity, the processing logic does not display the hypothetical detection result on the monitor. This suppression of the display of the hypothetical detection result is because, when the probe is moving, it is harder for the processing logic to estimate the hypothetical detection result, because it cannot estimate, for example, the symmetric change of shape and/or location of the blood vessel when the probe is moving.

During the time that the region of interest is compressed and relaxed with the probe of the ultrasound system, the shape of a blood vessel can change. For example, FIGS. 13A-13D illustrate period (i) during which the pressure by the probe increases to a certain level and the shape of a blood vessel changes (e.g., collapses) from a normal shape (usually a circular oval) to an additional shape (e.g., a collapsed oval). FIGS. 14A-14D illustrate the period (ii) during which the compression by the probe decreases from the certain level to the released state and the shape of a blood vessel changes from the additional shape back to the normal shape. During the periods (i) and (ii), ultrasound images are collected and blood vessels are detected. In some embodiments, the detection of blood vessels is performed using AI (e.g., AI software which implements a neural network).

In some embodiments, the detection results of ultrasound images that are acquired during the period (i) are analyzed, and results are created and used for the detection/analysis of the ultrasound images during the period (ii). For instance, the ultrasound system can use the detection results from period (i) as conditional inputs to a neural network to generate additional detection results for period (ii). Additionally or alternatively, the ultrasound system can use the location and the size of each of the detected blood vessels during the period (i) to predict (e.g., limit) the area for searching the blood vessels during the period (ii), thereby contributing to the fast and correct detection of the same blood vessel during the time period (ii). In an example, the ultrasound system can generate a region of interest based on the location and the size of each of the detected blood vessels during the period (i), and provide this region of interest as a conditional input to a neural network, which can then generate inferences for locations and sizes of blood vessels in accordance with the region of interest for the period (ii).

Figure 15:
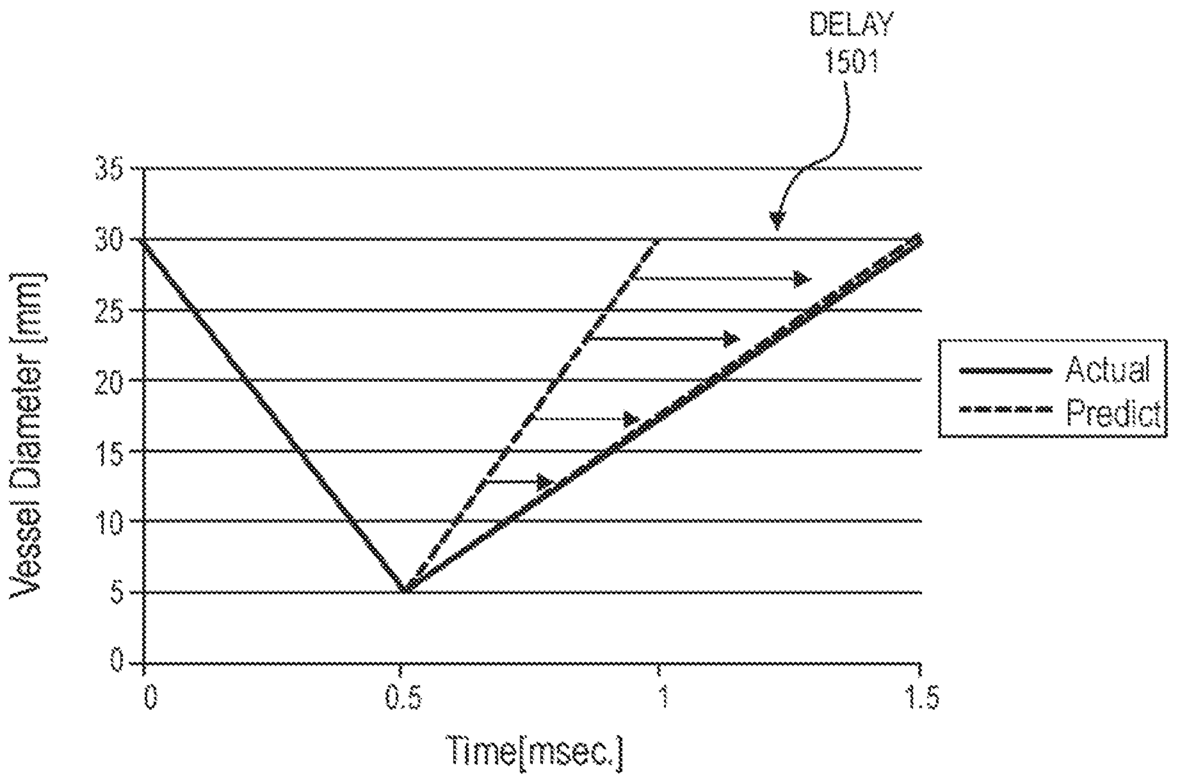
FIG. 15 illustrates a flow diagram of one embodiment of a process for using detection results of one period for creation of detection results for another period.

In one example, the ultrasound machine adjusts for a difference in the collapsing speed and the recovery speed of a blood vessel when determining the detection results of the period (ii) based on the detection results of the period (i). For instance, in an ultrasound examination using the probe, the probe gradually presses the examined part during the period (i), and the operator releases the probe during the period (ii). Therefore, the collapsing speed is generally dependent on the pressure caused by the probe, which is based on the pressing action by the operator. On the other hand, the recovery speed is mainly dependent on the property of the blood vessel itself (i.e., almost a constant speed). As has been observed by inventors, the recovery speed of the blood vessel itself is usually lower than the collapsing speed. Therefore, the processor can modify the detection results of the period (i) (e.g., by multiplying an appropriate coefficient to the detection results of the period (i) to delay the recovery feature) to match the actual recovery speed of the blood vessel. FIG. 15 includes a graph illustrating the relationship between the vessel diameter and time. Referring to FIG. 15, a delay 1501 represents the gap between the actual speed of recovery and that of the predicted speed that is assumed to be as the same as the collapsing speed, and has to be filled. In some embodiments, the ultrasound system calculates the collapsing speed by employing the detection of blood vessels, the determination of diameters, and the tracking technology, and then detects the timing of transition from the period (i) and period (ii), and then calculates the (actual) recovery speed by using first some frames of period (ii), and then a coefficient between the actual and the predicted speed is generated. Therefore, using the coefficient value, results of the detection during the period (i) is appropriately reflected in the detection process in the period (ii). Details are also explained using the flowchart of FIG. 16 below. In one example, such a coefficient can be updated by reiterently reflecting the detection results of the period (ii) as the time proceeds because the actual results (i.e. the diameters) of the same blood vessel amounts as the detection process proceeds, thereby the gap becomes more precise. In one example, the blood vessel diameter can be used instead of the diameters in FIGS. 15 and 16. Furthermore, it is noted that, although the technology explained with reference to FIGS. 15 and 16 can be based on a case where the period (i) refers to the collapsing speed and the period (ii) refers to the recovery speed, the technology can be also applied to a case where the period (i) refers to the recovery speed and the period (ii) refers to the collapsing speed.

Figure 16:
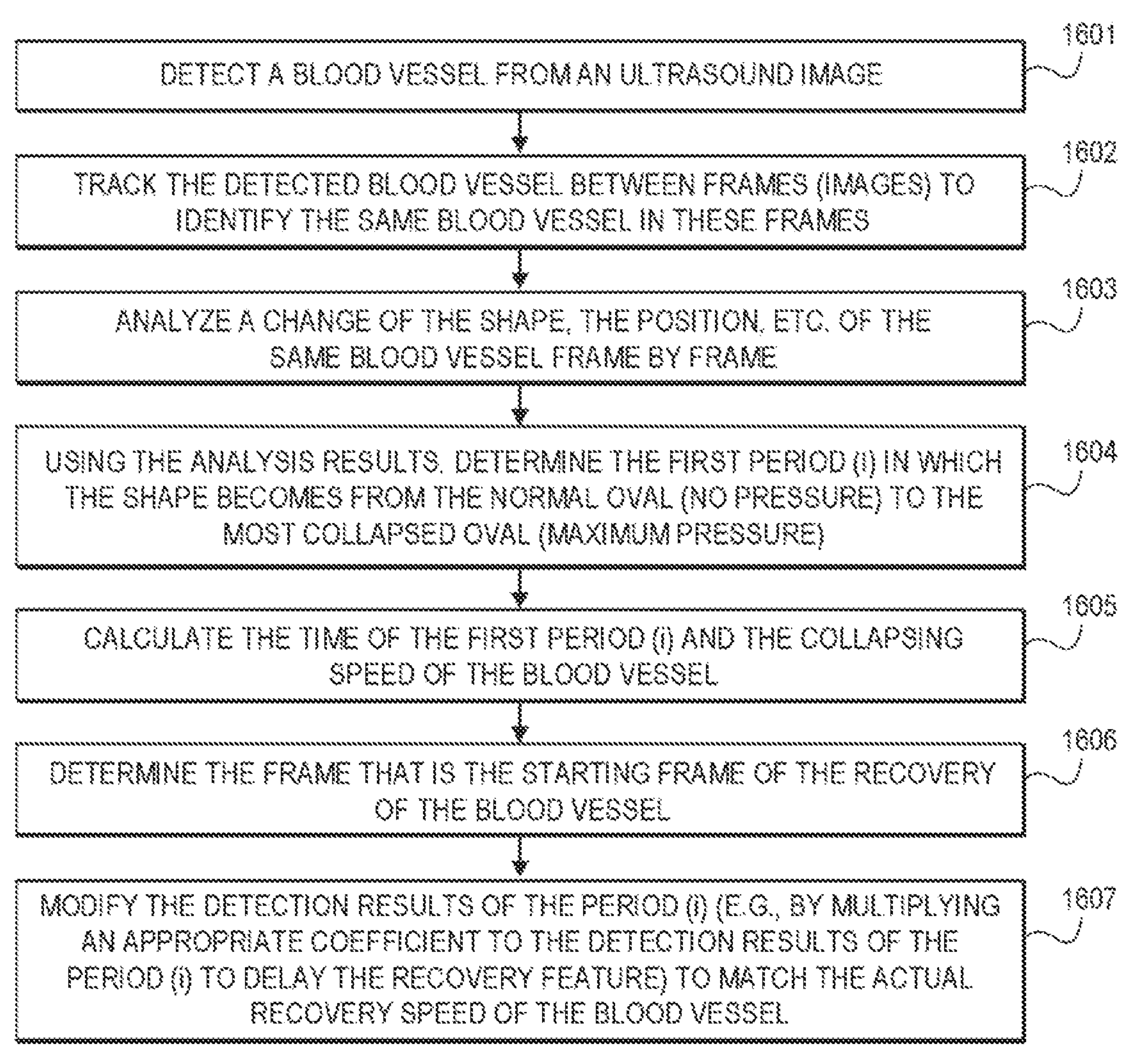
FIG. 16 illustrates a flow diagram of one embodiment of a process for using detection results of one period for creation of detection results for another period.

FIG. 16 illustrates a flow diagram of one embodiment of a process for using detection results of one period for creation of detection results for another period, for example, as previously described with respect to FIGS. 13A-15. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by a processor of an ultrasound machine.

Referring to FIG. 16, the process starts by processing logic detecting a blood vessel from an ultrasound image (processing block 1601). As discussed above, many different algorithms can be used to detect blood vessels, including, but not limited to, template-matching, machine-learning (e.g., adaboost, deep-learning, SVM, sequence models including RNN, GRU, ConvGRU, LSTM, etc., to process frame information in sequence, etc.), and the like.

Processing logic also tracks the detected blood vessel between frames (images) to identify the same blood vessel in these frames (processing block 1602). During the pressure by the probe, the shape of the detected blood vessel changes and processing logic analyzes the change of the shape, the position, the size, combinations thereof, etc. of the same blood vessel frame by frame (processing block 1603). In response to the analysis, processing logic determines the first period (i) in which the shape transitions from the normal oval (no pressure) to the most collapsed oval (maximum pressure) (processing block 1604). As the frame rate is predetermined by the ultrasound machine (e.g., 30 frames/sec), processing logic calculates the time of the first period and the collapsing speed of the blood vessel (processing block 1605). Thus, from processing blocks 1601 through 1605, processing logic obtains information of the blood vessel during period (i).

The processor determines the frame which is the starting frame of the recovery of the blood vessel (processing block 1606). For instance, the processing logic can equate the recovery speed of the blood vessel with the collapsing speed of the blood vessel. Then, the processor can determine the frame which is the starting frame of the recovery of the blood vessel, e.g., from this starting frame, it enters into the period (ii). The processor can then estimate the position, diameter, or other information of the blood vessel in the current frame, based on the detection results during the period (i) and the time interval between the current time and the time of the starting frame. In other words, at processing block 1606, some frames of period (ii) are also acquired, such that the time of change from period (i) to period (ii) is determined. Also, at processing block 1606, the processor can calculate the recovery speed by using the same frames of the period (ii) since these frames are already obtained, thereby a coefficient (corresponding to the delay 1501 of FIG. 15) to be applied to detection results during the period (i) is calculated based on the some frames of period (ii).

At processing block 1607, a new, current image (belonging to period (ii)) is obtained. Since the time interval between the current time and the time of change from period (i) to period (ii) and the coefficient are known, the information about the blood vessel at the appropriate time of period (i) is obtained for use in creating the new image. More specifically, the processor can account for differences between the recovery speed and the collapsing speed of the blood vessel. For example, in some embodiments, the processor modifies the detection results of the period (i), such as by multiplying an appropriate coefficient to the detection results of the period (i) to delay the recovery feature, to match the actual recovery speed of the blood vessel (processing block 1607). Therefore, the detection results at an appropriate time in the period (i) are input to the processor (e.g., AI algorithm) to enhance the detection of the blood vessels in the new, current image. In one example, the locations and/or the diameters of the blood vessels at an appropriate time in the period (i) are input to the processor (e.g., AI algorithm), thereby the region specified for search can be limited, and/or the size of blood vessel for search can be limited, thereby reducing the burden for the processor.

In some embodiments, after identifying blood vessels in an ultrasound image, a user may want to search for the best location of a blood vessel into which a needle or other interventional instrument can be inserted. For example, a blood vessel can extend from an elbow to a wrist, from an upper arm to an elbow, etc., and an operator may want to be able to search for a particular location, or position, of the blood vessel for needle insertion. However, when searching for the best position of a blood vessel, an operator moves a probe from one position to another, thereby obtaining a number of ultrasound images continuously that may be checked. In such a case, the operator may miss the best position for the testing and/or intervention as the probe is moving.

In some embodiments, while an ultrasound probe is in motion, ultrasound images that include a blood vessel are obtained. For instance, the ultrasound machine can generate the ultrasound images based on ultrasound echo signals received by the ultrasound probe. The ultrasound machine determines at least one ultrasound image of the ultrasound images based on a location of the ultrasound probe with respect to the blood vessel when the ultrasound image is received, and determines one or more features of the blood vessel in the ultrasound image. The ultrasound machine displays an indicator of each feature of the blood vessel in an additional ultrasound image (e.g. in a current ultrasound image).

In some embodiments, to show the best, or more desirable, location for insertion that the user has gone past, several past ultrasound images are obtained and image analysis, including the detection of blood vessels, is performed for each of the images. In some embodiments, the ultrasound machine selects one image from the past images, based on the analysis (hereafter the selected one image is also referred as 'best image'). In some embodiments, the image selected is the ultrasound image obtained when the probe was located at a desired part of the blood vessel for insertion. The determination of which location is best or desired can be based on predefined criteria. Such predefined criteria i can include the size of the diameter of the blood vessels, location of the predetermined blood vessels are shallower than a predetermined depth, etc. Examples of such predefined criteria are explained in greater detail below.

Figure 17:
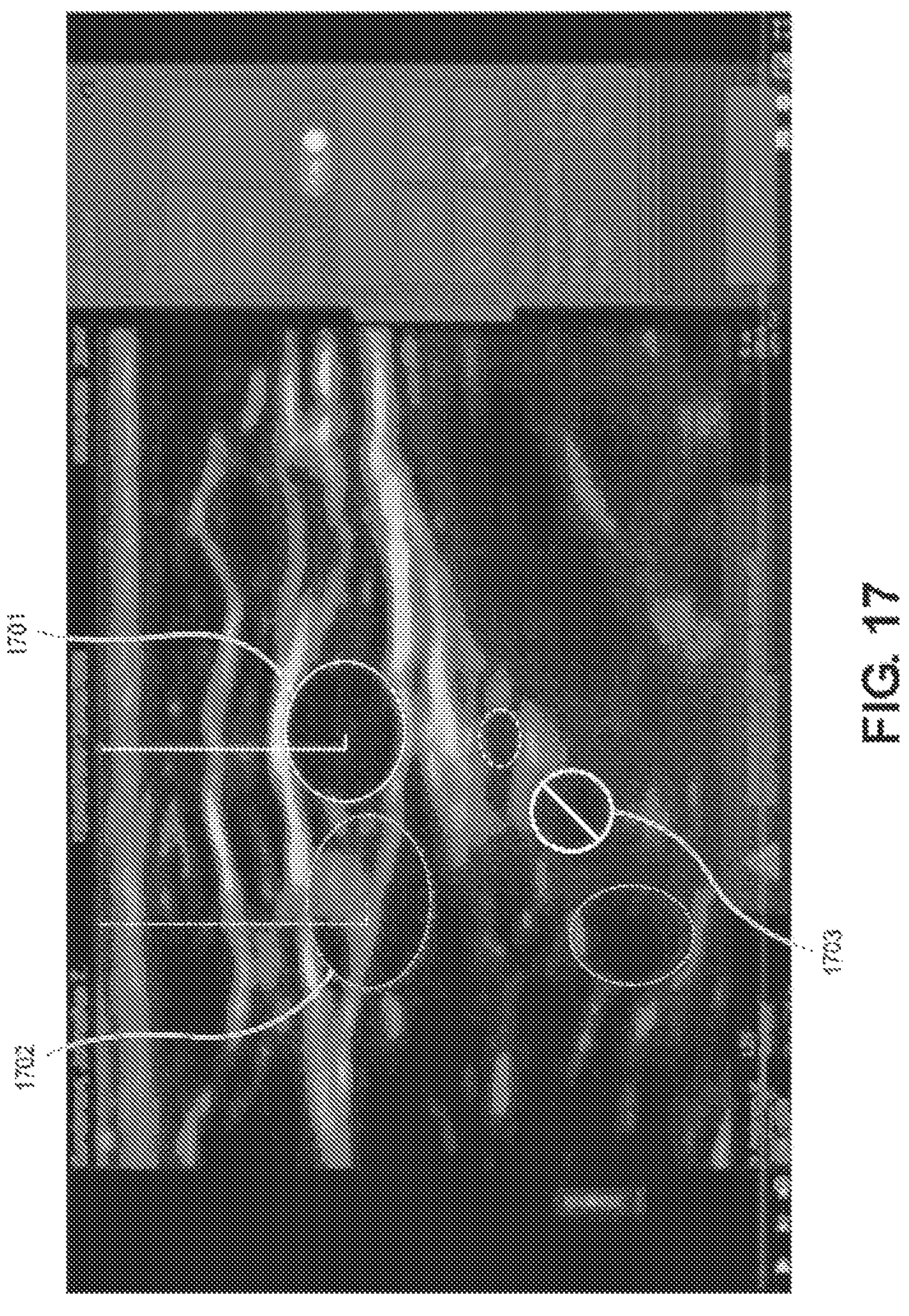
FIG. 17 illustrates an example of an image with a best image of a detected blood vessel superimposed on the image.

The information regarding the detected blood vessel of the best image can be superimposed on a current (live) image. This superimposition can be done much like a graphic being superimposed on an image. FIG. 17 illustrates an example of a current (live) image with such a superposition. Referring to FIG. 17, a vein 1701 is enhanced with an ellipse together with the addition of an L-shaped depth indicator. In one example, the L-shaped depth indicator can be additionally displayed if the location of a detected blood vessel is shallower than a predetermined depth. However, another blood vessel 1702 is shown superimposed on the current image as the information regarding the blood vessel of the best image of a blood vessel. Blood vessel 1703 is shown on the image as well and represents an artery. Hence, blood vessel 1703 is indicated with a strike-through, as opposed to a circle or ellipse lacking a strike-through, to emphasize blood vessel 1703 as an artery rather than a vein.

To identify and superimpose the information related to the best image, the best image of the blood vessel, the ultrasound machine can include a probe having a location sensor to provide location information that the processor analyzes. In some embodiment, the location sensor includes a gyro sensor or an accelerometer. In some embodiments, the images are stored with the location information of the probe in a memory.

The ultrasound machine also includes a processor(s) that can detect the blood vessel from an ultrasound image and select an image among a plurality of images as the best image, based on at least one of the following:

1) the diameter of the blood vessel is large (e.g., larger than a threshold or the largest among the plurality of images);
2) the detected blood vessel is located shallower than a predetermined depth;
3) the detected blood vessel is not located too close (e.g., within 2 mm laterally or 3-4 mm in depth) to an anatomical structure (such as, for example, but not limited to, a nerve or an artery) that would be injured or disturbed when inserting a needle or catheter;
4) the likelihood value as to detection of the blood vessel is high;
5) the internal structure of the blood vessel is determined to be clear. In other words, a blood vessel wall or a vascular intima is clearly seen in an ultrasound image;
6) there's no abnormal structure (e.g., blood clot, edema, etc.) observed in the blood vessel of an ultrasound image; and
7) the diameter of the blood vessel is stable around the periphery of the position of the blood vessel. In some embodiments, the ultrasound machine makes a selection that takes into account the position of the blood vessel being stable around the periphery of the position. In some embodiments, the word 'stable' means that the deviation of the diameter is less than a threshold diameter (e.g., 10-20% of the maximum diameter of the blood vessel). The word 'stable' may also mean that the deviation of the change in position is less than a threshold. As an instrument (e.g., a catheter) is inserted along the longitudinal direction of the blood vessel, such a deviation would be preferably small to prevent phlebitis due to the rub between the instrument and the blood vessel. In other words, it is not a good position for insertion where the blood vessel is constricted, such that the diameter is locally large but the position is significantly changing.

After determining the best image, the information related to the best image can be superimposed on the monitor that is currently displaying live B-mode images. In some embodiments, the information includes one or more of the following:

1) information regarding the detected blood vessel of the best image (e.g., the location of the blood vessel and/or the size of the blood vessel). An example of displaying such information would be a dashed circle that shows the diameter of the blood vessel in the past best image. Another example would be to display an arrow that points to the location of the blood vessel in the past best image. Still another example would be, if the detected blood vessel of the current image is the same as the blood vessel in the best image, the color for enhancing the same blood vessel is the same (e.g., a dashed-line green circle can be displayed as the blood vessel of the best image and a solid green circle can be displayed as the same blood vessel of the current image. As discussed above, in one example, the color of the circle can be selected based at least on the blood vessel diameter and/or the standard color corresponding to a catheter size). Additionally or alternatively, instead of the same color, the identification information of the blood vessel could be used;
2) time information (e.g., the time when the best image was obtained, the relative time from now, etc.);
3) guide information (e.g., by using the location of the probe). As the location information regarding the position where the best image was scanned is stored in the memory, the guide information is determined by comparing the position where the best image was scanned and the current position (e.g., showing the direction on the monitor to promote moving the probe to the position, or displaying the relative distance). In some embodiments, guide information is shown onto the schema (an illustration of the entire human body or a part of the body). For example, if the arm is displayed on the screen, the probe movement direction indicator (e.g., an arrow) can be overlaid on the arm illustration.

Figures 18A, 18B:
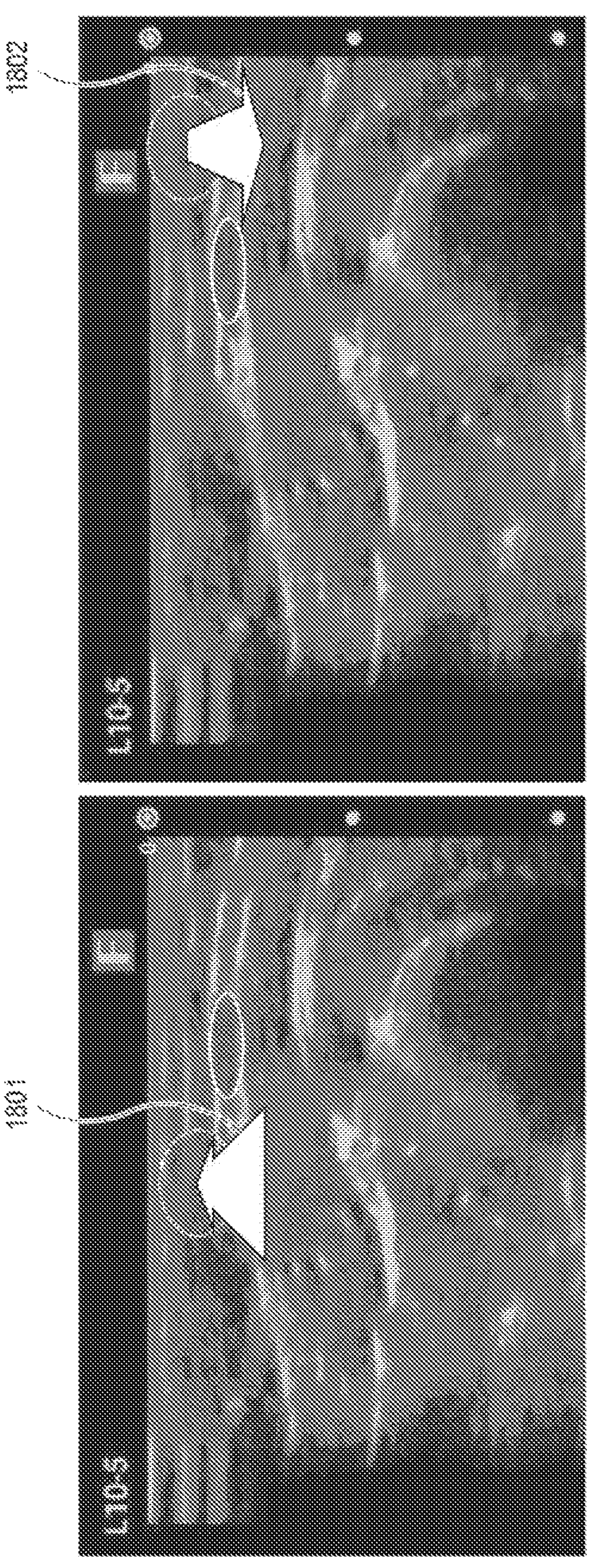
FIGS. 18A and 18B show an example of guide information, together with information regarding a best probe position.

FIGS. 18A and 18B show an example of the guide information, together with the information regarding the best position. Referring to FIGS. 18A and 18B, the solid-line oval represents the detected vein in the current image, and the dashed-line oval represents the detected (same) vein in the past best image. The arrows 1801 and 1802 represent the guide information.

In FIG. 18A, arrow 1801 goes into the dashed-line oval, with its distal portion becoming narrower. This arrow configuration indicates that the probe should move to the back side with respect to the monitor. In FIG. 18B, arrow 1802 goes out from the dashed-line oval, with its distal portion becoming wider. This arrow configuration indicates that the probe should move to the front side with respect to the monitor.

In some embodiments, the guide information is displayed together with the information regarding the detected blood vessel of the best image. For example, the ultrasound machine can display the guide information together with a diameter of the detected blood vessel and/or an indication of the classification of the blood vessel as a vein or artery as an annotation. As another example, the ultrasound machine can display the guide information together with a dashed circle of a color that can be selected based at least on the blood vessel diameter and/or the standard color corresponding to a catheter size.

Additionally or alternatively to displaying the above information, the ultrasound machine can provide audible information and/or tactile information to the operator of the ultrasound machine. For example, in some embodiments, as audible information, the frequency and/or the volume is changed according to the relative distance between the position of the best image and the current position. Thus, as the operator is moving the probe closer or farther away from the position of the best image, the audible information changes in one or more ways (e.g., becomes louder) to alert the user they are getting closer, or one or more other ways (e.g., becomes quieter) to alert the user they are getting farther away. In an example, as tactile information, the power of vibration and/or the pattern of vibration by the main unit (e.g., smartphone or tablet) of the probe is changed to indicate a proximity of the probe to the position of the best image.

In the case that the guide information is displayed on the monitor, the movement of the probe can be tracked to determine whether the probe is moved in accordance with the guide information or not. For example, in the case that the audible information is provided to the operator, the ultrasound machine can track the movement of the probe to determine whether the probe is moved in accordance with the audible information or not. As another example, when the operator moves the probe in a wrong direction relative to the guide information and/or audible information, the ultrasound system can provide an indicator of the wrong direction, such as by displaying a stop-sign icon, caution icon, wrong-direction icon, and the like, and/or playing an audio signal that is not pleasing to the operator, such as the words "stop", "wrong direction", etc., or a tone with an unpleasant beep. Additionally or alternatively, when the operator moves the probe in a correct direction relative to the guide information and/or audible information, the ultrasound system can provide an indicator of the correct direction, such as by displaying a proceed icon, traffic light icon with green light illuminated, and the like, and/or playing an audio signal that is pleasing to the operator, such as the words "proceed", "correct direction", etc., applause, cheers, or a series of tones with a pleasant harmony.

Exemplary Flow Diagrams

In some embodiments, the ultrasound system identifies blood vessels and guides instrument insertion. In some embodiments, the ultrasound system includes an image module that generates one or more ultrasound images based on ultrasound echo signals, a neural network module and a processor(s) that operate together to perform blood vessel identification and/or generate and display guidance information for instrument insertion, and a map module that generates a map image indicating locations of blood vessels. These modules can be implemented as any type of module or component in software (e.g., as software instructions that are executable with a processing system), hardware, or combinations thereof, as a standalone application or as a module or component of another device application, and in any type of computing device. As discussed above, the instrument can be a catheter, needle or another medical tool.

In some embodiments, as discussed above, the neural network module identifies blood vessels in one or more ultrasound images and assigns to each blood vessel a classification as a vein or an artery. In one embodiment, the neural network module implements one or more artificial intelligence (AI) algorithms (e.g., neural networks) to identify blood vessels in an image and classify them as veins or arteries.

In some embodiments, the neural network module operates with a map module of the ultrasound system to identify the blood vessels in the ultrasound images. The map module can be executed by a processor of the ultrasound system and generates a map image that indicates locations of blood vessels in an image identified by the neural network module. That is, the neural network module identifies the blood vessels in an image and then the map module generates a map image that indicates their location.

In some embodiments, the neural network module is configured to generate a feature map from an image that represents the content of the image in a feature space. The neural network module can then concatenate the feature map and a map image from the map module to identify the blood vessels in the image. The map image can correspond to a previous image in a sequence of ultrasound images in which the neural network module has identified the blood vessels. For example, the neural network module can use the map image from one ultrasound image to identify blood vessels in another ultrasound image.

In some embodiments, the map module is configured to generate the map image to indicate the locations of blood vessels using bounding containers that can include outlines of the blood vessels. For instance, the map image can include just the bounding containers to designate the locations of blood vessels and no ultrasound image data. Additionally or alternatively, the map module can be configured to generate the map image as a mask that indicates the locations of the blood vessels with a first color, or pixel value, (e.g., white), and additional locations in the map image that do not correspond to the blood vessels with another color, or second pixel value, (e.g., black).

In some embodiments, the neural network module adapts over time. For example, the AI algorithm(s) performed by the neural network module can be modified such as by changing one or more neural network coefficients. These coefficients can be adjusted based on a function (e.g., a loss function, L2 norm, etc.), and the coefficient adjustments can be based on results of identifying and/or determining the locations of the blood vessels in one image or multiple images (e.g., images in the same video, same examination, same procedure, etc.).

FIGS. 19A-21 are examples of processes for blood vessel identification and/or generating and displaying guidance information.

Figure 19A:
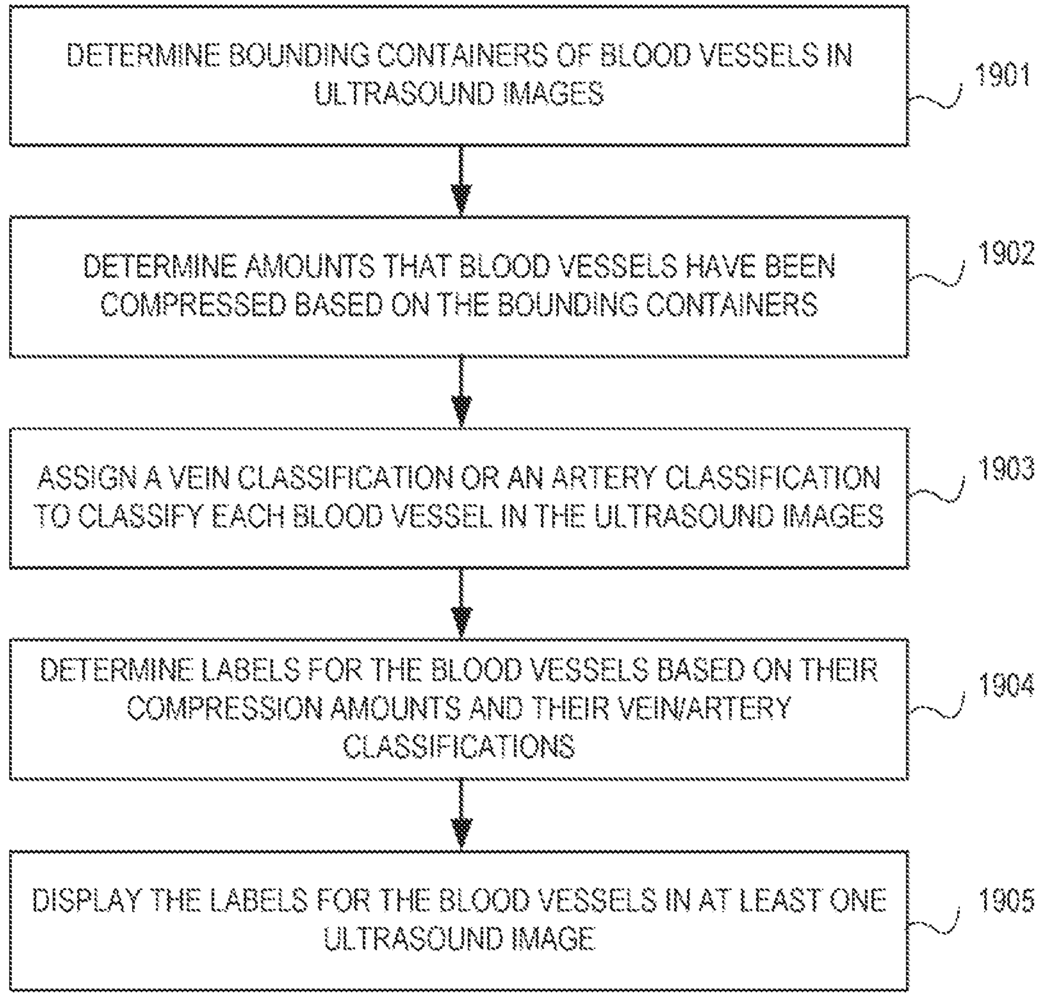
FIG. 19A is a flow diagram of another embodiment of a process for identifying blood vessels.

FIG. 19A is a flow diagram of another embodiment of a process for identifying blood vessels. The process may be related to the technique described in conjunction with FIGS. 1A and 1B. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by a neural network and/or processor of an ultrasound machine.

Referring to FIG. 19A, the process begins by processing logic determining bounding containers of blood vessels in ultrasound images (processing block 1901). Boxes 101 and 102 in FIG. 1A are examples of bounding containers determined by the processing logic in processing block 1901. In one embodiment, the processing logic determines the bounding containers of blood vessels in the ultrasound images using a neural network of the neural network module. In one embodiment, the neural network is implemented in at least partially hardware of a computing device. However, the neural network can be implemented at least partially in software, hardware, and/or firmware.

After determining the bounding containers of blood vessels in the ultrasound images, processing logic determines amounts that blood vessels have been compressed based on the bounding containers (processing block 1902). In one embodiment, the processing logic determines the compression amounts of the blood vessels by determining first lengths of the bounding containers (e.g., a horizontal length across the bounding containers), second lengths of the bounding containers (e.g., a vertical length across the bounding containers), and then ratios of the first lengths to the second lengths. As an example, the processing logic can determine the compression amount of a blood vessel as a ratio of a major axis to a minor axis of an ellipse (e.g., a bounding container) that denotes the blood vessel.

After determining amounts that blood vessels have become compressed based on the bounding containers, processing logic assigns a vein classification or an artery classification to classify each blood vessel in the ultrasound images (processing block 1903). In one embodiment, processing logic assigns the vein or artery classification using a neural network. In one embodiment, processing logic determines the amount that blood vessels have become compressed and assigns the vein/artery classifications for blood vessels in one ultrasound image. The determination and assignment can be based on the compression amounts and assigned vein/artery classifications for blood vessels in one or more additional ultrasound images (e.g., images in the same sequence or video of ultrasound images in the one ultrasound image).

After assigning vein/artery classifications, processing logic determines labels for the blood vessels based on their compression amounts and their vein/artery classifications (processing block 1904). In one embodiment, the labels indicate, for each of the blood vessels, whether they are classified as a vein or an artery. In one embodiment, processing logic determines labels for the blood vessels by comparing the compression amounts to a compression threshold. If the compression amount is greater than or equal to the compression threshold, the processing logic can assign a vein classification to the blood vessel. Otherwise, if the compression amount for the blood vessel is less than the compression threshold, the processing logic can assign an artery classification to the blood vessel.

After determining labels for the blood vessels based on compression amounts and the classifications of the blood vessels as veins or arteries, processing logic displays the labels for the blood vessels in at least one ultrasound image (processing block 1905). The processing logic can display the labels as part of another designator, such as by color-coding a bounding container, with the color based on the vein/artery classification. Additionally or alternatively, the processing logic can display the labels separate from bounding containers, such as with an 'A' for artery and 'V' for vein.

In some embodiments, the ultrasound machine uses template matching, centroid tracking, or other object tracking methods to monitor a detection (e.g., blood vessel detection) that is made throughout a video sequence of ultrasound images. In some embodiments, given that consecutive frames should be highly correlated in ultrasound videos due to the gradual movement made during scanning, the ultrasound machine can track a detection from frame to frame. In one example, such a tracking technology can be performed between the block 1901 and the block 1902, or can be embedded in the block 1901 or 1902 by the processing logic. By tracking a detection over many frames, it is possible to avoid misclassification of a detection over the range of a few frames. For example, if the ultrasound machine determines a detection for a blood vessel was a vein for 10 frames and then the blood vessel is suddenly classified as an artery, it is likely that the artery classification is a misclassification which should be overturned in favor of a classification as a vein. Applying this method over a few frames prevents flickering between classes for a continuous vessel.

In some embodiments, after the neural network assigns a classification to a blood vessel as being a vein or artery, the neural network can make another determination that classifies a blood vessel, previously classified as a vein, as an artery (or vice versa), which is a misclassification. To address this situation, the ultrasound system is able to correct the misclassification for purposes of displaying the vein/artery classification in the ultrasound image in the display.

Figure 19B:
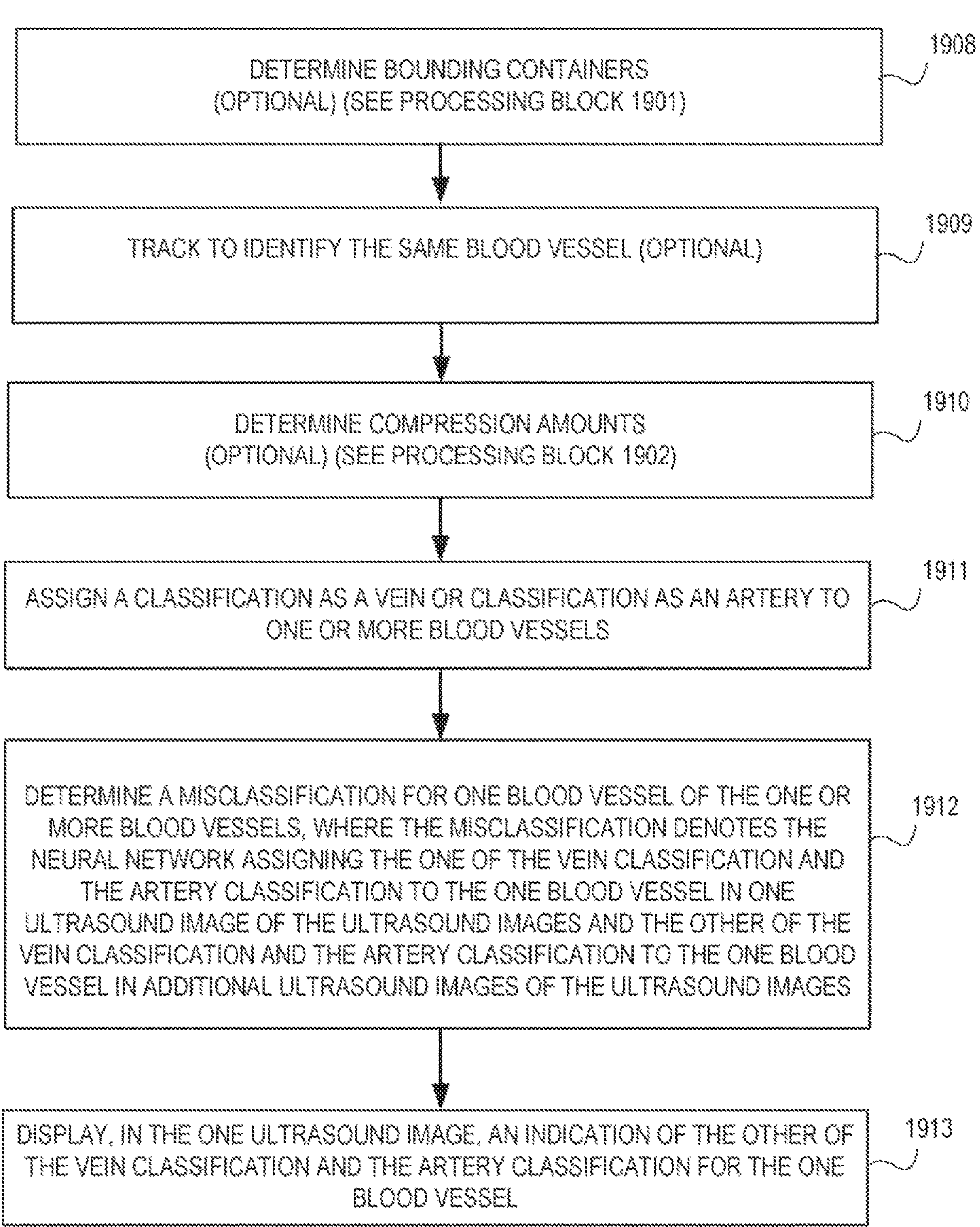
FIG. 19B is a flow diagram of one embodiment of a process for identifying blood vessels in which a misclassification of a blood vessel occurs.

FIG. 19B is a flow diagram of one embodiment of process for identifying blood vessels in which a misclassification of a blood vessel occurs. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by a neural network and/or processor of an ultrasound machine.

Referring to FIG. 19B, in some embodiments, the process begins with processing logic determining bounding containers (processing block 1908), performing tracking to identify the same blood (processing block 1909), and determining compression amounts (processing block 1910). Note that these operations are not performed in all embodiments and thus may not performed prior to the remaining operations in FIG. 19B.

Thereafter, processing logic assigning a classification as a vein or classification as an artery to one or more blood vessels (processing block 1911). In one embodiment, assigning a classification of a vein or an artery to one blood vessel in an ultrasound image is based on assigning the classification as a vein or an artery in at least one additional ultrasound image. In some embodiments, assigning the blood vessel a classification as a vein or an artery in one ultrasound image is based on the ultrasound image itself and at least one set of additional ultrasound images. In some embodiments, these additional ultrasound images are gray scale images and assigning a vein/artery classification to one blood vessel in the one ultrasound image includes receiving gray scale images on separate color channels by the neural network and having the neural network use those images to make vein/artery classifications.

After assigning a vein/artery classification, processing logic determines a misclassification for one blood vessel of the one or more blood vessels (processing block 1912). In some embodiments, the misclassification denotes the neural network assigning the one of the vein classification and the artery classification to the one blood vessel in one ultrasound image of the ultrasound images and the other of the vein classification and the artery classification to the one blood vessel in additional ones of the ultrasound images. In one embodiment, the misclassification denotes that the neural network has assigned a blood vessel classification as a vein or an artery in one ultrasound image and the classification should have been the opposite based on the classification that occurred in one or more additional images. In one embodiment, the determination that a misclassification occurred may be the result of processing logic detecting a blood vessel in multiple ultrasound images and then failing to detect the blood vessel in a subsequent ultrasound image (e.g., an ultrasound image that follows the multiple ultrasound images in a video sequence). The failure to detect the blood vessel in a subsequent image can be determined based on the likelihood value associated with the classification of the blood vessel falling below a threshold that needed to be achieved in order to be classified as it was in the previous images. In some embodiments, processing logic can use a hysteresis method by which a vessel is very confidently detected at some point and then its probability threshold falls to a point that must be reached to no longer be considered a valid detection. In another embodiment, the determination of the misclassification can be based on the condition that the likelihood value for the one of an artery or a vein has been higher than that for the other (and optionally higher than the threshold) in multiple images and suddenly becomes lower (and optionally lower than the threshold) in a subsequent ultrasound image. The one ultrasound image and the additional ultrasound image can represent frames in an ultrasound video. In one example, the one ultrasound image represents a later frame in the ultrasound video than the additional ultrasound images that represent previous frames in the ultrasound video. In one embodiment, the previous frames represented by the additional ultrasound images are consecutive frames in the ultrasound video.

In some embodiments, the process includes receiving a user selection that indicates a time interval over which the blood vessel determination should be made. In such cases, the neural network can use the one ultrasound image and the additional ultrasound images representing frames in an ultrasound video in determining the misclassification based on the number of frames corresponding to or covered by the time interval.

After determining the misclassification for a blood vessel, processing logic displays, in the one ultrasound image, an indication of the other of the vein classification and the artery classification for the one blood vessel (processing block 1913). In other words, processing logic displays the correct classification for the misclassified blood vessel as a vein or artery in the displayed image. In an example, the processing logic designates the correct classification for a misclassified blood vessel in a manner to indicate that the classification has been corrected for the misclassified blood vessel, such as with shaded, hashed, dotted, etc. indicators of the classification. In one example, such an indication of the corrected classification can be in a different from than that of the confident classification.

Additionally or alternatively, traditional tracking could help compensate for frames in which there was a missed detection, as the tracking can identify the same blood vessel in consecutive frames. For example, if a vessel is centered on the screen and appears to not be compressed for 10 frames, and then in the next frame it is no longer detected, then it is possible to estimate its position using template matching, information from other detected vessels, or traditional tracking, and persist the detection over several frames, giving time for the detector to start detecting the vessel again. To prevent persistence of vessels that shouldn't be persisted, certain rules such as not persisting frames with compressed aspect ratios or those very near the edges could be implemented. As another example, the tracking can help search for likelihood values of the same blood vessel.

Given the nature of veins and arteries, it can be expected that vessels that compress more are likely to be veins. Hence, if the processor can track a blood vessel over a duration of a video based on detections of the blood vessel, the processor can ensure that a blood vessel that was previously compressed will continue to be classified as a vein, adding an element of information from previous frames about the nature of the blood vessel to the detection in subsequent frames.

Figure 19C:
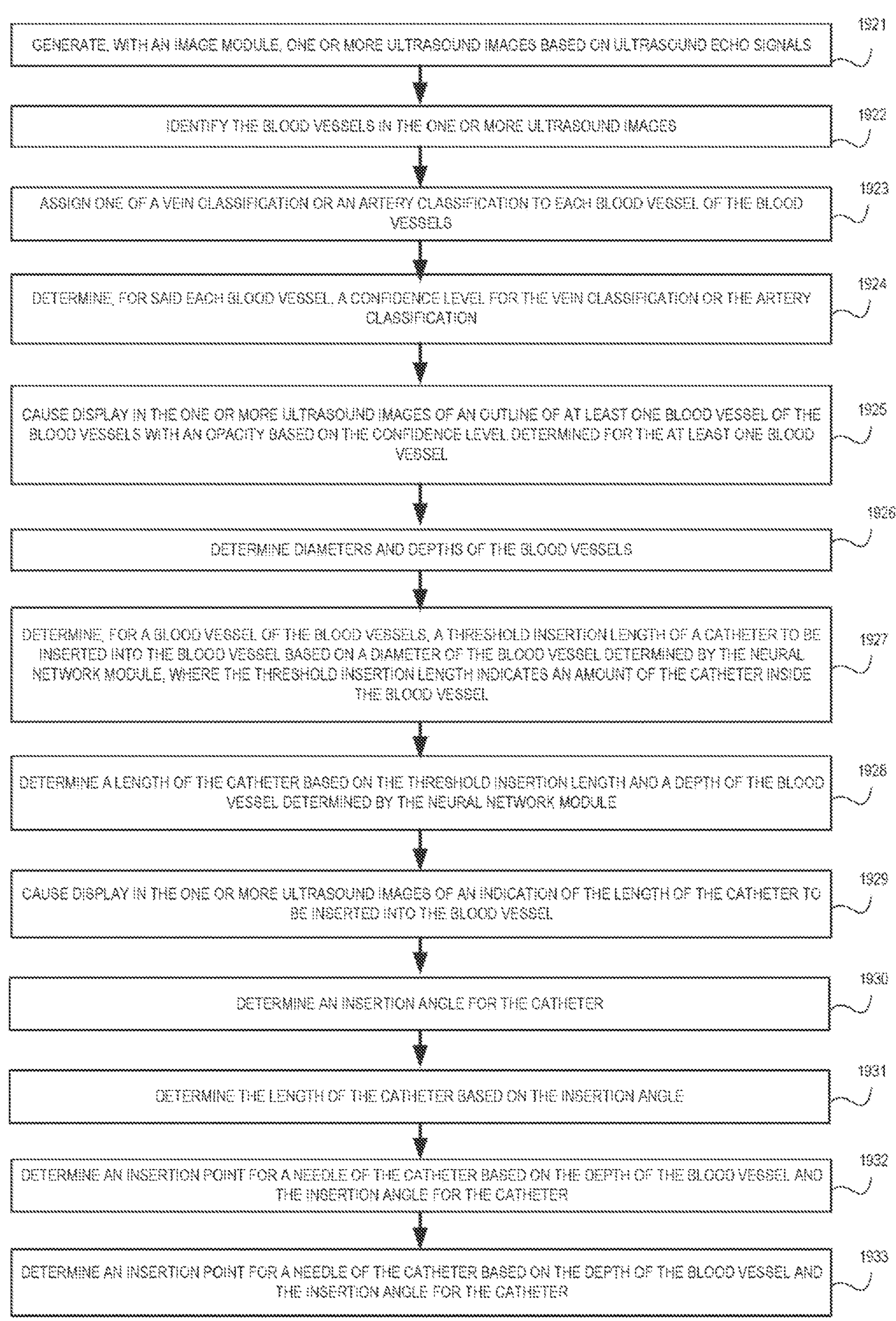
FIG. 19C is a flow diagram of another embodiment of a process for identifying blood vessels.

FIG. 19C is a flow diagram of another embodiment of a process for identifying blood vessels. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process or portions thereof are performed by a neural network and/or processor of an ultrasound machine.

Referring to FIG. 19C, the process begins by processing logic generating one or more ultrasound images based on ultrasound echo signals (processing block 1921). In one embodiment, generating ultrasound images based on ultrasound echo signals is performed by an image module.

Processing logic identifies the blood vessels in the one or more ultrasound images (processing block 1922) and assigns one of a vein classification or an artery classification to each blood vessel of the blood vessels (processing block 1923). In some embodiments, these operations are performed with a neural network module.

In some embodiments, processing logic determines, for each blood vessel, a confidence level for the vein classification or the artery classification (processing block 1924). In some embodiments, determining the confidence level for the vein classification or the artery classification is performed with a processor. Additionally or alternatively, a neural network can determine a confidence level for the classification, such as by generating a probability of correct classification, and determining the confidence level based on the probability of correct classification.

Processing logic causes the display in the one or more ultrasound images of an outline of at least one blood vessel of the blood vessels with an opacity based on the confidence level determined for the at least one blood vessel (processing block 1925). In some embodiments, causing the display in the one or more ultrasound images of an outline of at least one blood vessel of the blood vessels with an opacity based on the confidence level is performed with a processor.

In some embodiments, the process includes processing logic determining diameters and depths of the blood vessels (processing block 1926) and determining, for a blood vessel of the blood vessels, a threshold insertion length of a catheter to be inserted into the blood vessel based on a diameter of the blood vessel (processing block 1927). The threshold insertion length indicates an amount of the catheter inside the blood vessel. In some embodiments, determining diameters and depths of the blood vessels is performed with a neural network module, while a processor determines the threshold insertion length of the catheter.

The process also includes processing logic determining a length of the catheter based on the threshold insertion length and a depth of the blood vessel (processing block 1928) and causing display in the one or more ultrasound images of an indication of the length of the catheter to be inserted into the blood vessel (processing block 1929). In some embodiments, these operations are performed with a processor.

The process also includes processing logic determining an insertion angle for the catheter (processing block 1930), and determining the length of the catheter based on the insertion angle (processing block 1931). For instance, the processor can determine the sum of the threshold insertion length and the depth of the blood vessel, and weight this sum by a coefficient that accounts for the insertion angle, such as by multiplying the sum by the inverse of the cosine of the insertion angle. The processor can then determine the length of the catheter to be at least as long as the weighted result.

The process also includes determining an insertion point for a needle of the catheter based on the depth of the blood vessel and the insertion angle for the catheter (processing block 1932), and indicating the insertion point as a distance from the transducer (optional) (processing block 1933). In one embodiment, these operations are performed with a processor. In some embodiments, the processor determines the insertion angle for the catheter using information other than the diameter or the depth of the blood vessel. For example, the processor can read the insertion angle from a default setting, such as 45 degrees set in a default register. In some embodiments, the process further includes determining the distance from a face of the transducer.

Figure 19D:
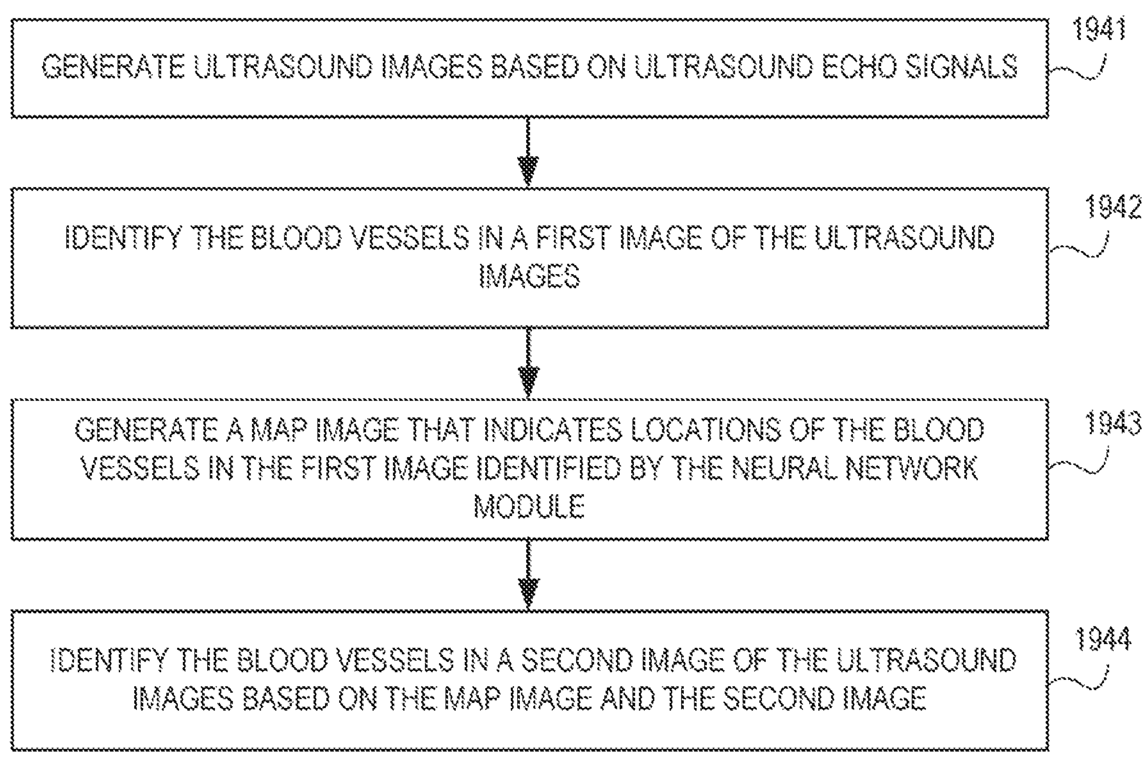
FIG. 19D is a flow diagram of yet another embodiment of a process for identifying blood vessels.

FIG. 19D is a flow diagram of yet another embodiment of a process for identifying blood vessels. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process or portions thereof are performed by a neural network and/or processor of an ultrasound machine.

Referring to FIG. 19D, the process begins by processing logic generating ultrasound images based on ultrasound echo signals (processing block 1941). In some embodiments, generating ultrasound images based on ultrasound echo signals is performed by an image module.

After generating the ultrasound images, processing logic identifies the blood vessels in a first image of the ultrasound images (processing block 1942). In some embodiments, identifying the blood vessels in a first image of the ultrasound images is performed with a neural network module.

Processing logic also generates a map image that indicates locations of the blood vessels in the first image identified by the neural network module (processing block 1943). In some embodiments, generating a map image is performed with a map module. The map module can be configured to generate the map image to indicate the locations of the blood vessels in the first image with bounding containers. The bounding containers can include outlines of the blood vessels. In some embodiments, the map module is configured to generate the map image as a mask that indicates the locations of the blood vessels with a first pixel value and additional locations in the map image that do not correspond to the blood vessels with a second pixel value.

Thereafter, processing logic identifies the blood vessels in a second image of the ultrasound images based on the map image and the second image (processing block 1944). In some embodiments, identifying the blood vessels in a second image of the ultrasound images based on the map image and the second image is performed with the neural network module. In some embodiments, the neural network module is configured to adjust at least one neural network coefficient based on a loss function of the locations of the blood vessels in the first image and additional locations of the blood vessels in the second image.

In some embodiments, the process further comprises generating a feature map from the second image that represents content of the second image in a feature space, concatenating the feature map and the map image, and identifying the blood vessels in the second image based on results of concatenation. In some embodiments, these operations are performed by a neural network module.

In some embodiments, a neural network of the neural network module identifies blood vessels and their locations for use in a medical procedure. The neural network performs the identification of blood vessels in conjunction with other determinations such as the determination of blood vessel depth and size (e.g., diameter, radius, area, etc.), appropriate or suitable implements for use in the medical procedure, as well as guidance information to help a user during the medical procedure.

Figure 20A:
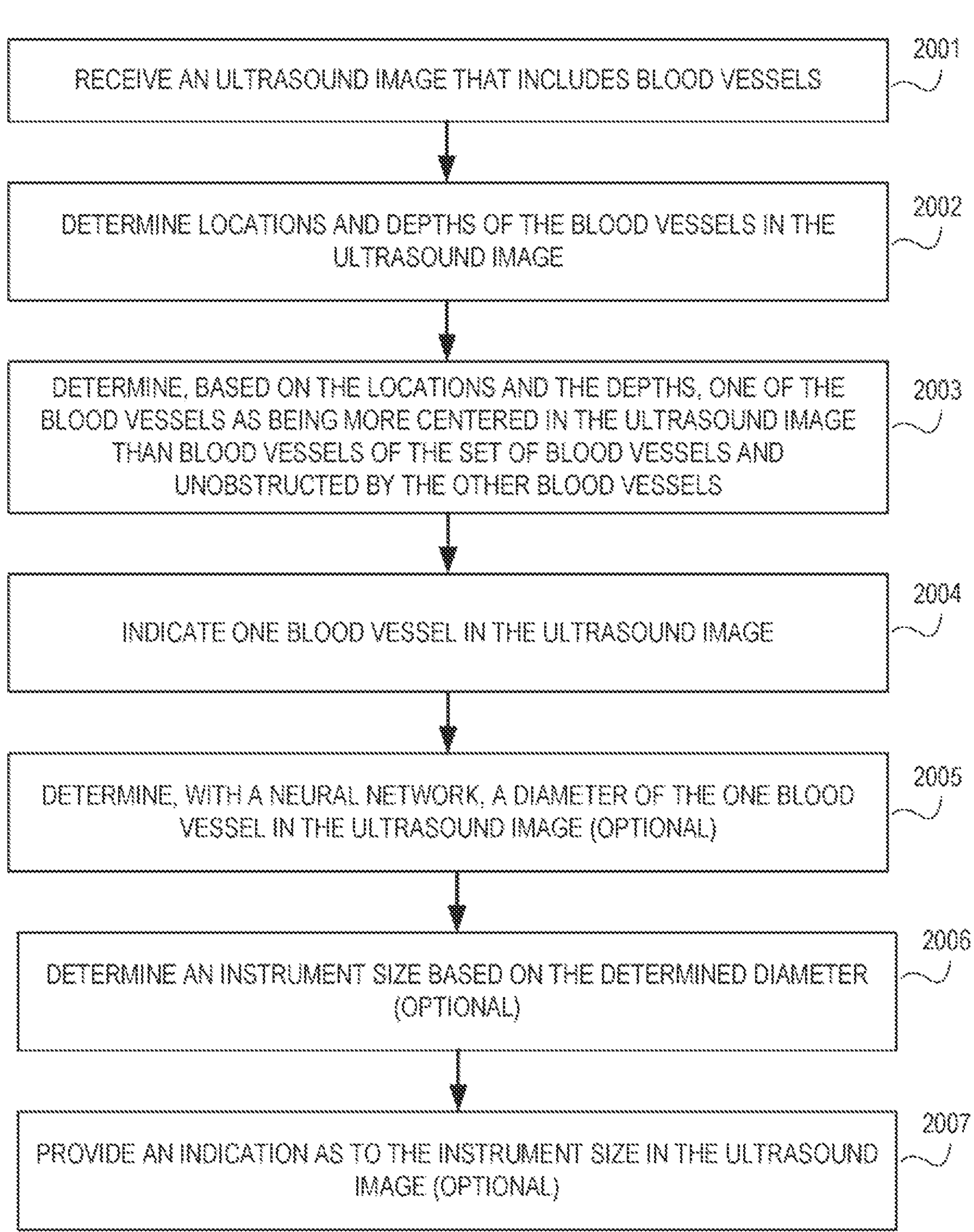
FIG. 20A is a flow diagram of yet another embodiment of a process for identifying blood vessels for uses such as a medical procedure.

FIG. 20A is a flow diagram of yet another embodiment of a process for identifying blood vessels for uses such as a medical procedure. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by a neural network and/or processor of an ultrasound machine.

Referring to FIG. 20A, the process begins with the processing logic receiving an ultrasound image that includes blood vessels (processing block 2001). After receiving the ultrasound image, processing logic determines the locations and depths of the blood vessels in the ultrasound image (processing block 2002). In one embodiment, the ultrasound system determines the locations and depths of the blood vessels in the ultrasound image using a neural network. The neural network can be implemented at least partially in hardware. Additionally or alternatively, the neural network can be implemented at least partially in software and/or firmware. In one embodiment, determining the locations and the depths of the blood vessels is based on additional ultrasound images. For example, the ultrasound images in these additional ultrasound images can represent frames of an ultrasound video. In some embodiments, determining the locations and depths of the blood vessels is based on additional ultrasound images where at least one of the additional ultrasound images indicates a previously determined location and depth of one of the blood vessels determined by the neural network.

Based on the locations and depths of blood vessels in the ultrasound image, processing logic determines one of the blood vessels as being more centered in the ultrasound image than other blood vessels of the blood vessels that have been determined (processing block 2003). In some embodiments, determining one of the blood vessels is more centered in the ultrasound image is made by determining that the blood vessel is centrally located between both left and right sides of the ultrasound image. Additionally or alternatively, the ultrasound system can determine that one of the blood vessels is more centered than the other blood vessels in the image by determining that the one of the blood vessels is aligned, based on an alignment threshold, with a center line of the ultrasound image. In some embodiments, the ultrasound system draws a center line between the left and right sides of an image down from the top and determines if the one blood vessel crosses that line. The determination of whether the blood vessel crosses the line can be based on whether a bounding box used to indicate the location of the blood vessel in the ultrasound image crosses the line, which can be done by the ultrasound system based on a comparison of coordinates of a bounding container (e.g., x,y endpoints of abounding box) and the points of the line. For more information, see FIGS. 11A-111D and FIG. 17, and their accompanying descriptions above.

Additionally or alternatively, the process can determine whether the one blood vessel is unobstructed by the other blood vessels that are located at the same horizontal position as the one blood vessel in an ultrasound image. In one embodiment, determining if one of the blood vessels is unobstructed by the other blood vessels is performed by the processor by determining that the one blood vessel has a shallower depth than the depths of the other blood vessels.

After determining one of the blood vessels is more centered in the ultrasound image than other blood vessels, processing logic indicates the blood vessel in the ultrasound image (processing block 2004). In some embodiments, processing logic indicates the one blood vessel by providing an indication of the blood vessel in the ultrasound image, as discussed with reference to FIGS. 11A-11D and FIG. 17.

The process of FIG. 20A optionally includes processing logic determining, with a neural network, a diameter of the one blood vessel in the ultrasound image (processing block 2005), determining an instrument size based on the determined diameter (processing block 2006), and providing an indication as to the instrument size in the ultrasound image (processing block 2007). In some embodiments, processing logic determines the instrument size based on determining the largest appropriate instrument for a blood vessel having that sized diameter. For example, processing logic can determine an appropriately sized instrument based on the results of comparing the ratios of the instrument size to the diameters of the blood vessels to a threshold ratio size. These ratios can be determined by a processor of the ultrasound machine. Hence, the processor can determine that an appropriately sized instrument for a particular blood vessel is limited in gauge to a percentage of a diameter for the blood vessel, such as no greater than 50% of the diameter of the blood vessel. The process may optionally include processing logic for calculating a blood vessel diameter, such that the determination of an instrument size is based on the blood vessel diameter. In some embodiments, this calculation can be performed between processing blocks 2005 and 2006.

In some embodiments, indicating the instrument size includes displaying the bounding container of a blood vessel in a color corresponding to the instrument size. In one embodiment, the bounding container includes a circle, an ellipse, a highlight, etc., as an outline of the blood vessel. In some embodiments, a processor in the ultrasound system selects a color based on the instrument size and indicates one or more of the blood vessels with the color in one or more ultrasound images. For example, the processor selects the color based on instrument size and then displays the blood vessels with that color in one or more ultrasound images.

In one example, the neural network determines depths of the blood vessels in ultrasound images, and the processor system determines one of the blood vessels having the shallowest depth. The processor system can then cause display of a depth and diameter of the one blood vessel, as determined by the neural network, in the ultrasound images automatically and without user intervention.

In some embodiments, the process also includes receiving a user selection of at least one of the blood vessels. For example, a user may touch a touchscreen display at the location of the blood vessel to indicate the blood vessel, enable a selection of a pull-down tab, and the like. In response to the user selection, the processor can cause the display in one or more ultrasound images of a diameter of that selected blood vessel.

Figure 20B:
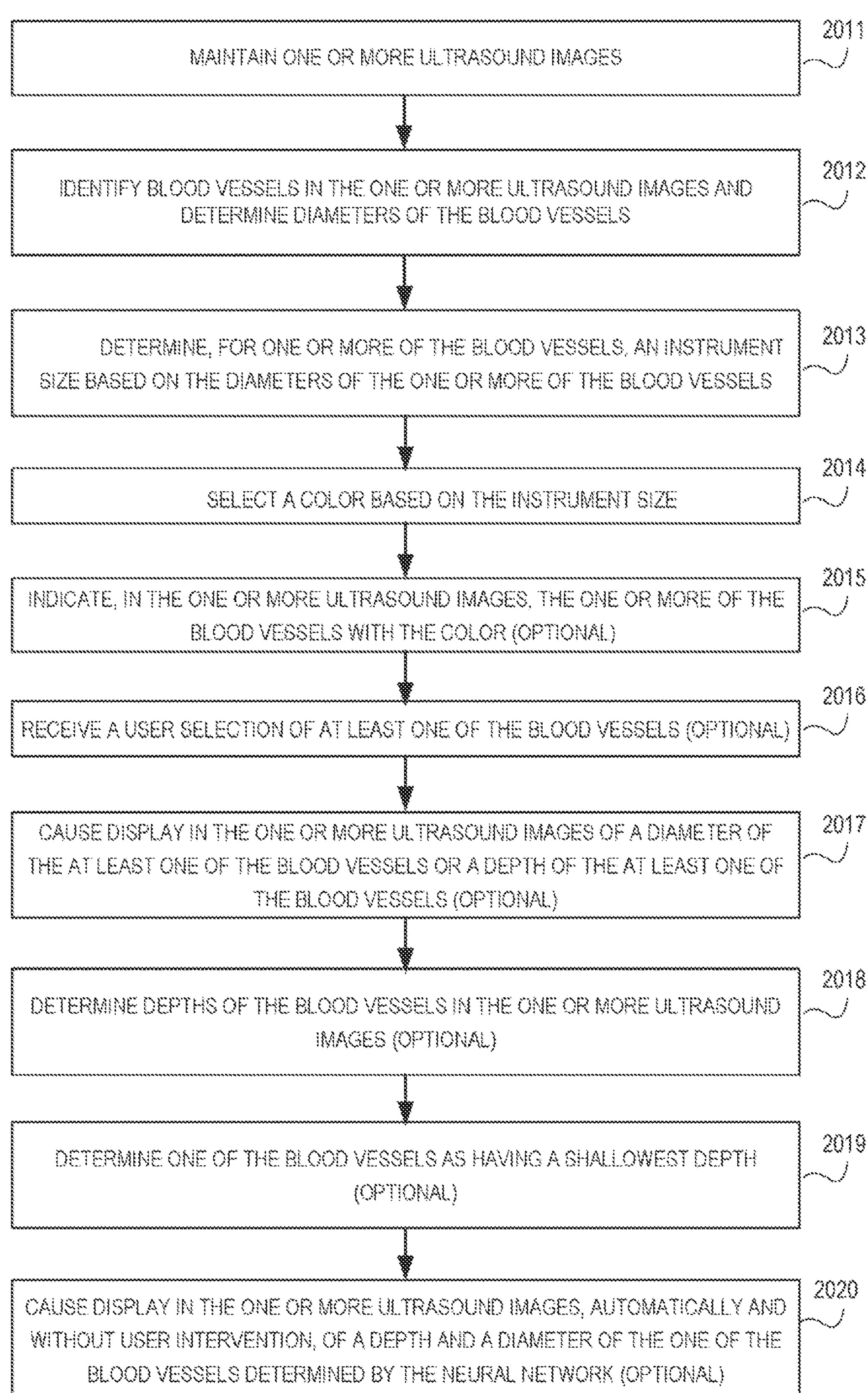
FIG. 20B is a flow diagram of another embodiment of a process for guiding instrument insertion with an ultrasound machine.

FIG. 20B is a flow diagram of another embodiment of a process for guiding instrument insertion with an ultrasound machine. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process or portions thereof are performed by a neural network and/or processor of the ultrasound machine.

Referring to FIG. 20B, the process begins by processing logic maintaining one or more ultrasound images (processing block 2011). Using these ultrasound images, processing logic identifies blood vessels in the one or more ultrasound images and determines diameters of the blood vessels (processing block 2012). In some embodiments, identifying the blood vessels in a first image of the ultrasound images is performed with a neural network module.

Next, processing logic determines, for one or more of the blood vessels, an instrument size based on the diameters of the one or more of the blood vessels (processing block 2013) and selects a color based on the instrument size (processing block 2014). In some embodiments, these operations are performed by the processor system.

The process also optionally includes processing logic indicating, in the one or more ultrasound images, the one or more of the blood vessels with the color (processing block 2015). The process can also include receiving a user selection of at least one of the blood vessels (processing block 2016), and causing display in the one or more ultrasound images of a diameter of the at least one of the blood vessels or a depth of the at least one of the blood vessels (processing block 2017). In some embodiments, these operations are performed by the processor system. In one embodiment, a parameter associated with a blood vessel diameter can be used instead of diameter in FIG. 20B. In such a case, for example, the processing logic can determine a blood vessel diameter in the block 2012 and can determine, for one or more of the blood vessels, an instrument size based on the blood vessel diameters of the one or more of the blood vessels in the block 2013.

The process also optionally includes processing logic determining depths of the blood vessels in the one or more ultrasound images (processing block 2018), determining one of the blood vessels as having a shallowest depth (processing block 2019), and causing display in the one or more ultrasound images, automatically and without user intervention, of a depth and a diameter of the one of the blood vessels (processing block 2020). In some embodiments, determining depths of the blood vessels in the one or more ultrasound images is performed by a neural network, while the other operations are performed by the processor system.

Figure 21:
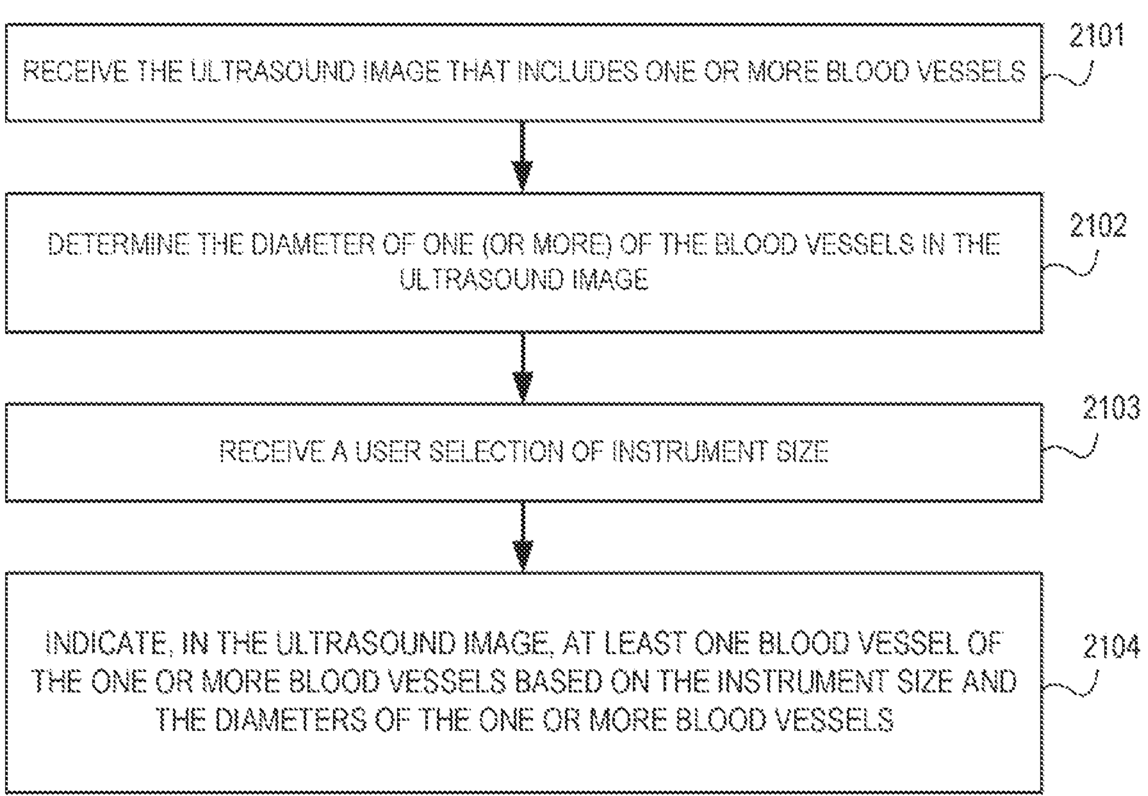
FIG. 21 is a flow diagram of one embodiment of a process for guiding instrument insertion.

FIG. 21 is a flow diagram of one embodiment of a process for guiding instrument insertion. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by a neural network and/or processor of an ultrasound machine.

Referring to FIG. 21, the process begins by processing logic receiving the ultrasound image that includes one or more blood vessels (processing block 2101). In some embodiments, processing logic also determines the locations of the blood vessels in the ultrasound image and classifies blood vessels as veins or arteries. In an example, a neural network determines these locations and performs the classification. In some embodiments, the neural network also determines a confidence level associated with the assigned vein/artery classification. The ultrasound machine can display an outline of each blood vessel (e.g., a bounding container) with an opacity based on the confidence level associated with the vein/artery classification determined for the blood vessel. In one embodiment, processing logic determines the distance of at least one blood vessel to an edge of the ultrasound image, and then displays the outline for the at least one blood vessel by displaying the outline with an opacity based on that distance.

In response to receiving the ultrasound image, processing logic determines the diameter of one (or more) of the blood vessels in the ultrasound image (processing block 2102). The techniques disclosed herein are not limited to determining a size of a blood vessel as the diameter of the blood vessel. For example, in some embodiments, processing logic determines and uses other size measurements such as a radius, an area, a circumference, combinations thereof, such as ratios, etc. In other embodiments, processing logic determines a blood vessel diameter discussed above as the diameter of the blood vessel. In one embodiment, a neural network determines a size measurement of the blood vessels based on the ultrasound image and one or more additional ultrasound images that include the same blood vessels. The additional images may be part of the same ultrasound video or part of the same ultrasound examination/procedure. These images used to determine the size of the blood vessels may be consecutive images or non-consecutive images. The ultrasound system can generate the additional ultrasound images based on an imaging parameter that is set to a different value than a value of the imaging parameter used to generate the ultrasound image being processed. For example, the ultrasound system can generate one or more additional ultrasound images based on a beamform angle that is different than an additional beamform angle used to generate the ultrasound signal used for generating the ultrasound image being processed. The ultrasound system can generate these additional images with information indicating locations corresponding to one or more blood vessels using, for example, one or more boundary containers.

After determining the diameters of the blood vessels in the ultrasound image, processing logic receives a user selection of instrument size (processing block 2103). The instrument size corresponds to an instrument that is going to be inserted into the blood vessel, such as, for example, a catheter, a needle, etc.

After receiving the user selection of instrument size, processing logic indicates, in the ultrasound image, at least one blood vessel of the one or more blood vessels based on the instrument size and the diameters of the one or more blood vessels (processing block 2104). In some embodiments, processing logic indicates the one blood vessel by providing an indication with at least one blood vessel in the ultrasound image indicating the appropriate instrument size for each of the one or more blood vessels (e.g., for blood vessels of that diameter, blood vessels of that radius, blood vessels of that area). The processing logic can determine the appropriate instrument size based on instruments that are used for a medical procedure to be performed by the ultrasound machine operator. In some embodiments, processing logic provides an indication of the blood vessel(s) by displaying an outline of the identified blood vessels in an ultrasound image. The processing logic can display the outline of at least one of the blood vessels by displaying an outline in a particular color that is associated with the instrument size. In some embodiments, processing logic can provide an indication regarding at least one blood vessel and the appropriately sized instrument to use based on the results of a comparison between ratios to a threshold ratio size, where the ratios correspond to ratios of the instrument size to the diameters of the blood vessels. In such a case, processing logic can determine the ratios of the instrument size to the diameters of the blood vessels and compare those ratios to the threshold ratio size. Note that the comparisons may be performed using measurements (e.g., radius, area, etc.) other than diameters.

While the discussions above focus on making single image frame inferences, in some embodiments, a neural network is configured to make inferences based on multiple frames. Such multi-frame interferences can be used to help improve overall interframe model consistency of the neural network models and monitor a vein through compressions. In some embodiments, the multi-frame inferences are performed by feeding inferences from previous frames into the model as additional inputs (e.g., conditional inputs) to provide hints to the model where blood vessels might be found as well as the size of the blood vessels. One example of the additional inputs includes a map image generated by the map module, as discussed above. The map image generated by the map image module for a previous image frame can be provided as a conditional input to the neural network for generating inferences for a current, or subsequent, image frame.

The procedures described herein constitute improvements over procedures that do not display blood vessels in ultrasound images with enhancements. Rather, the procedures described herein generate enhancements that include useful, and sometimes critical, information, and display the information to an operator of an ultrasound system so that the operator can apply the information to the ultrasound procedure in real-time. Hence, the procedures described herein can result in significant improvements to a patient's experience, including reducing, or even minimizing, the number of times an interventional instrument is inserted into a patient, resulting in pain and infection risk for the patient, and as well as preventing an undesired insertion of the instrument, e.g., into an artery rather than a vein. Accordingly, the patient does not perceive unnecessary pain and discomfort, and the risk of one or more of infection, thrombus due to insertion of too large of a catheter, extravasation, and damage to a vessel wall is reduced compared to conventional ultrasound procedures that do not display blood vessels with enhancements. Therefore, the procedures described herein can be suitable to medical procedures and examinations for which conventional ultrasound procedures are not suitable.

Example Ultrasound Machines

Figure 22:
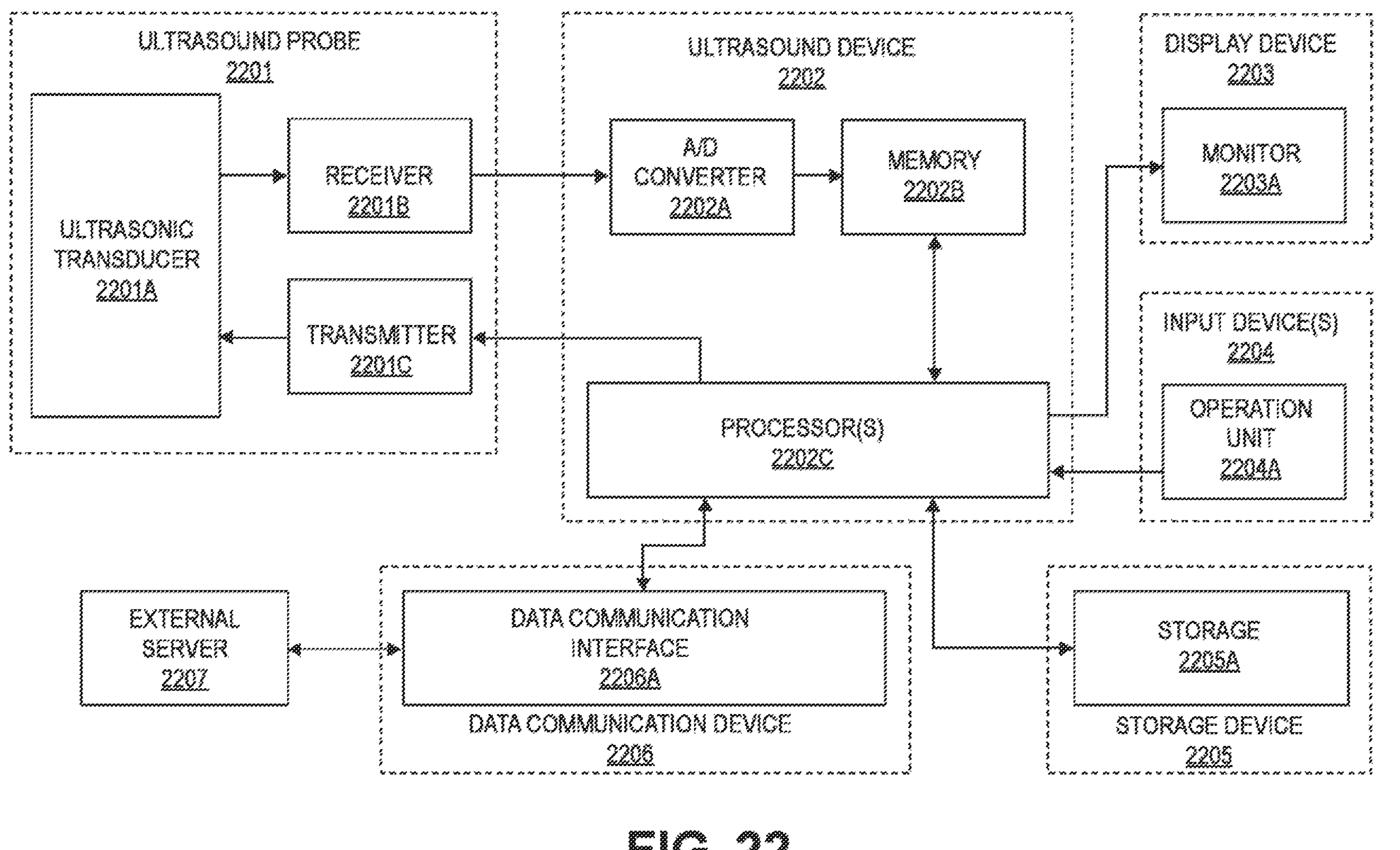
FIG. 22 illustrates a block diagram of one embodiment of an ultrasound machine.

FIG. 22 is a block diagram of one embodiment of an ultrasound machine. Note that any type of ultrasound machine can be used to perform the blood vessel identification and enhanced display techniques described herein, including a stationary-type, a portable-type, a handheld type, and combinations thereof. The block diagram is one example of an ultrasound machine that can be constructed using the blocks in FIG. 22. For instance, signals can be redefined, and blocks can be modified, combined, divided, added, or removed to form a modified system, without altering the functionality of the block diagram. Accordingly, such modified systems are considered to be within the scope of the disclosure. Moreover, the blocks, modules and units of an ultrasound machine, such as the ultrasound machine illustrated in FIG. 22, can be implemented as any type of module or component in software (e.g., as software instructions that are executable with a processing system), hardware, or combinations thereof, as a standalone application or as a module or component of another device application, and in any type of computing device.

Referring to FIG. 22, the ultrasound machine includes an ultrasound transducer probe 2201 coupled to an ultrasound device 2202. Ultrasound transducer probe 2201 includes an ultrasonic transducer 2201A electrically coupled to a receiver 2201B and a transmitter 2201C. Ultrasonic transducer 2201A has one or more transducer elements and in operation, transmits ultrasound energy from the one or more transducer elements toward a subject in response to transmitter signals from transmitter 2201C and receives ultrasound echoes from the subject using receiver 2201B. Receiver 2210B and transmitter 2210C can include any type of circuit, or any types of other form such as a processor, as described below. Receiver 2210B and transmitter 2210C can be formed separately or integrated into a single form. Receiver 2210B and transmitter 2210C can be integrated into a processor that has other functions, such as processor 2202C described below. The ultrasound echoes are converted into electrical signals by receiver 2201B and electrically coupled to electronics (e.g., analog/digital (A/D) converter 2202A, one or more processor(s) 2202C, memory modules 2202B, beamformers, FPGAs, etc.) in ultrasound device 2202 configured to process the electrical signals and form one or more ultrasound images.

In one example, ultrasound probe 2201 includes an A/D converter (not shown in FIG. 22) that can be configured to digitize the electrical signals generated by receiver 2201B that are based on the ultrasound echoes. Furthermore, ultrasound probe 2201 can also include a partial or full beamformer (not shown in FIG. 22) configured to sum the electrical signals in a phase-corrected manner. Hence, the ultrasound probe 2201 can be implemented to couple digital signals to ultrasound device 2202, such as over a wired or wireless communication link. For instance, ultrasound probe 2201 and ultrasound device 2202 can each include transceivers (not shown in FIG. 22) that communicate using communication signals that have been digitally modulated based on the digital signals.

Processor 2202C can include any type or any number of an application-specific integrated circuit (ASIC), a field-programmable gate array (FPGA), an integrated circuit (IC), logic, etc., partially or wholly. In some embodiments, processor 2202C includes a beamformer, and includes processing to form an ultrasound image. Note also that the processing described herein can be performed at least partially in the cloud, on an attached or networked processing device, on a discrete or external GPU, or custom specific attached hardware such as a USB attached device.

Capturing ultrasound data from a subject using an ultrasound probe 2201 generally includes generating ultrasound, transmitting ultrasound into the subject, and receiving ultrasound reflected by the subject. A wide range of frequencies of ultrasound may be used to capture ultrasound data, such as, for example, low frequency ultrasound (e.g., less than 15 MHz) and/or high frequency ultrasound (e.g., greater than or equal to 15 MHz) can be used. Those of ordinary skill in the art can readily determine which frequency range to use based on factors such as, for example, but not limited to, depth of imaging and/or desired resolution.

In some embodiments, ultrasound device 2202 includes one or more processor(s) 2202C that cause electrical currents to be sent to the ultrasound probe 2201 to emit sound waves and also receives the electrical pulses from probe 2201 that were created from the returning echoes. The A/D converter 2202A receives analog signals from receiver 2201B and converts them into digital data that is stored in memory 2202B. Memory 2202B also stores software and other data (e.g., templates, user preferences for enhancements, etc.) related to detecting blood vessels (e.g., veins, arteries, and capillaries.), and analytical results along with ultrasound images and other data associated therewith.

Processor 2202C processes the raw data associated with the received electrical pulses and forms an image that is sent to display device 2203, which displays the image on monitor 2203A. Thus, monitor 2203A can display ultrasound images from the ultrasound data processed by processor 2202C of ultrasound device 2202. Monitor 2203A can also display blood vessel detection results, as well as guide information of the probe as discussed herein. In one example, monitor 2203A includes a clinical display device. Additionally or alternatively, monitor 2203A can include a display of a computing device coupled to the ultrasound machine, such as a tablet.

In some embodiments, processor 2202C performs blood vessel detection using template matching, artificial intelligence or machine-learning (e.g., adaptive boosting (adaboost), deep-learning, support vector machine (SVM), sequence models including RNN, GRU, ConvGRU, LSTM, etc., to process frame information in sequence, etc.), and/or another detection method. In some embodiments, the processor 2202C executes an AI algorithm and/or uses a neural network to identify veins and arteries and locate them in an ultrasound image.

In some embodiments, after processor 2202C detects blood vessels, processor 2202C displays the blood vessels on a monitor or display of the ultrasound system. In an example, the detected blood vessels are displayed by processor 2202C in an enhanced manner to provide information to the operator, or user of the ultrasound machine. In some embodiments, processor 2202C draws outlines or other forms of blood vessel indicia (e.g., identifiers) around or in the proximity of the blood vessels.

By displaying blood vessels in an enhanced form, additional information can be made available to the operator. For example, in some embodiments, an outline of the vein is changed to match the color coding of the largest catheter that could fit within that vein. The color coding may be an industry standard color coding for catheters. In this way, an operator is able to quickly know the catheter that may be used with a particular blood vessel. In this way, an operator selects a catheter size based on the blood vessels being displayed. Alternatively, by being able to color code blood vessels according to the largest catheter, an operator could select a catheter size and have the ultrasound system identify all blood vessels (e.g., veins) in the image that are appropriate for that catheter size.

Additionally or alternatively, processor 2202C could identify all veins in the image that are appropriate for a particular catheter size. In some embodiments, an operator is able to touch a vein in the image and have processor 2202C display the diameter and depth for that blood vessel. In some embodiments, processor 2202C automatically identifies the most central and shallowest vein and automatically provides its diameter and depth for that vein on the display of the ultrasound machine.

In some embodiments, processor 2202C calculates a likelihood value for each detected blood vessel as an indication of a confidence level associated with the detection results. In one example, processor 2202C generates outlines of vein/artery that are made more or less opaque to indicate the confidence of the prediction for that vessel. In some embodiments, processor 2202C adjusts the opacity with fading that can be done by alpha blending the outline (e.g., an ellipse outline) with the b-mode image. In some embodiments, the amount of fading used may not be linear to the confidence, but rather an empirically derived curve based on what is determined to be pleasing to the user. The use of fading achieves a dual purpose of giving the user more information to use in making a final determination and also makes the display more visually appealing because vessels fade in and out rather than suddenly appearing and disappearing. In some embodiments, processor 2202C performs fading based on vessel size. In some embodiments in which only vessels down to a certain size are detected and where vessels near the minimum size are of less clinical importance than larger vessels, the ultrasound machine can fade out vessels as their detected size gets close to the minimum size. In some embodiments, due to the methods of annotating the training data and training the model, the accuracy of the model decreases for vessels detected towards the bottom and the sides. This is partially due to the ambiguity of determining when a vessel is too far out of the image to annotate or detect. In such a case, processor 2202C can perform fading based on proximity to the sides and bottom of the image.

In some embodiments, processor 2202C tracks the detected blood vessels across frames and identifies the same detected blood vessel in multiple images. The processor 2202C can use blood vessel location information or the type of blood vessel for the tracking and/or identification.

In some embodiments, processor 2202C uses the blood vessel identification and vein/artery classification information output from the neural network to generate and display information for PIV or other medical procedures. The information can include suggested catheter gauges, needle entry point information, guidance information (e.g., calculated distances from the transducer face or edge to a desired entry point of a PIV needle, etc.), a threshold insertion length of a catheter to be inserted into the blood vessel, catheter or other medical instrument length, combinations thereof, and the like. In some embodiments, this information is determined by processor 2202C based on diameters and depths of the blood vessels, threshold exertion length, insertion angle for the catheter determined by the neural network or processor 2202C. Note that processor 2202C can determine the insertion angle for the catheter based on something other than the diameter or the depth of the blood vessel. For instance, processor 2202C can determine the insertion angle as a default insertion angle, such as 45 degrees, that processor 2202C reads from memory 2202*b* and does not depend on the diameter or depth of a blood vessel determined by the ultrasound machine. After generating this information, the processor can display any portion or all of the information to the user in an ultrasound image or in another portion of the user interface of the ultrasound machine.

In some embodiments, the ultrasound system has one or more user input devices 2204 (e.g., a keyboard, a cursor control device, etc.) that input data from at least one operation unit 2204A. Along with memory 2202B, the ultrasound system also has a storage device 2205 that includes storage 2205A (e.g., hard, floppy, compact disks (CD), digital video discs (DVDs)) for storing the acquired images (e.g., past images, current images, etc.), which may be used for calculating a blood vessel diameter, selecting the best image for the insertion, other another operation described herein. The ultrasound system further includes a data communication device 2206 with a data communication interface 2206A for providing communication between ultrasound device 2202 and an external server 2207. In some embodiments, the probe of the ultrasound machine includes an additional sensor, such as an accelerometer or six degrees-of-freedom (6DOF) inertial measurement unit (IMU). The additional sensor can be used by the operator to perform functions such as, for example, estimating probe pose and providing user guidance (e.g., for directing the user back to a best vein for cannulation) and for providing a better understanding of the artery and vein structures along a limb. For example, when a vein with appropriate depth and diameter is found, the ultrasound system can track the probe location to ensure that the vein is not tortuous and does not have valves over a length that is appropriate for the length of the catheter.

Figure 23:
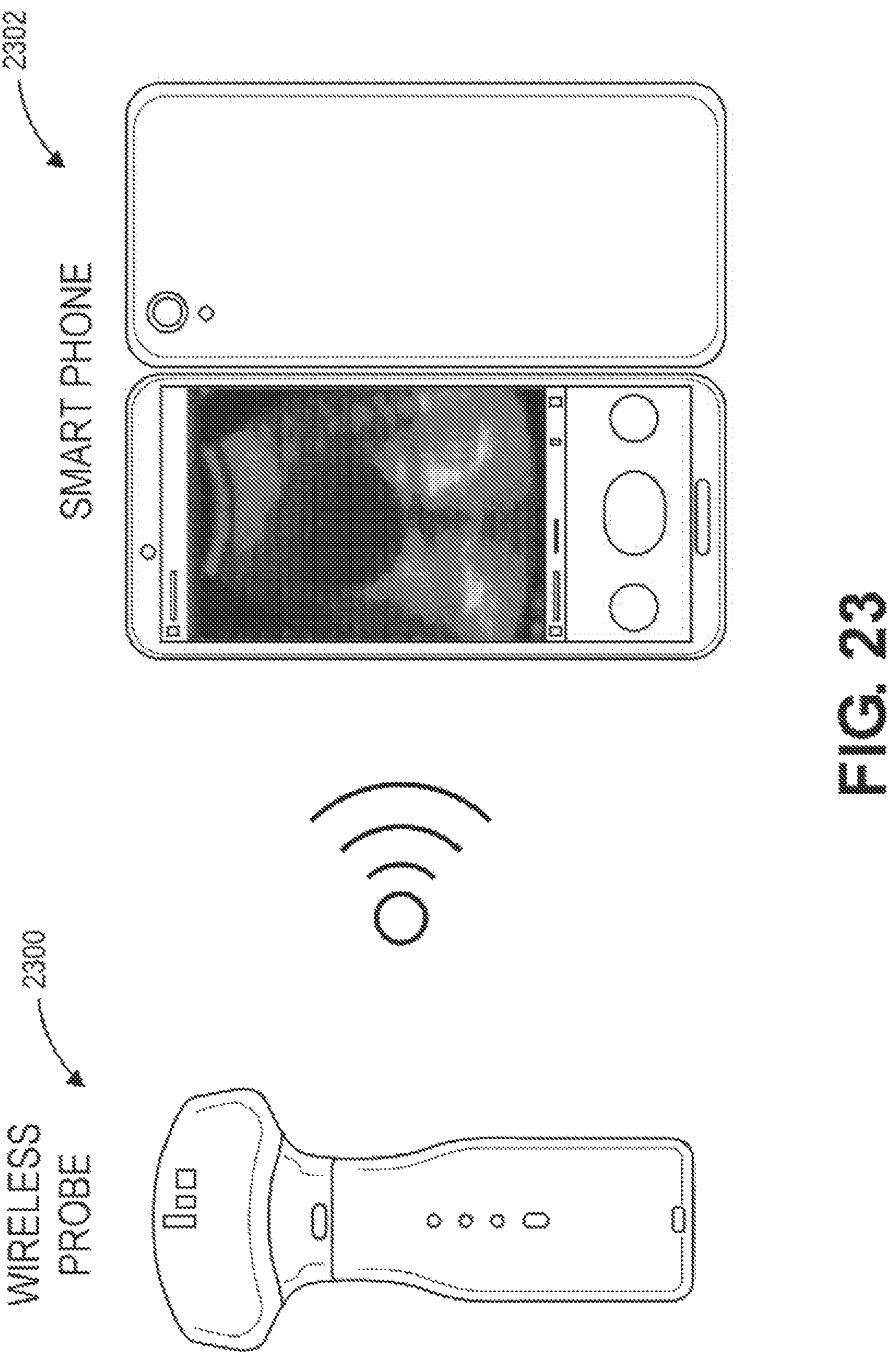
FIG. 23 illustrates an example of a hand-held ultrasound machine.

In some embodiments, the ultrasound machine includes a hand-held ultrasound apparatus having a probe and a tablet or smartphone connected to each other. The connection may be wireless or wired. FIG. 23 illustrates an example of such an ultrasound machine. Referring to FIG. 23, a wireless ultrasound probe 2300 wirelessly communicates with smart phone 2302. In some embodiments, probe 2300 includes hardware and software that function to perform transmission/reception by an array of transducers, A/D conversion; beamforming; quadrature detection; and wireless transmission. In some embodiments, smart phone 2302 includes hardware and software that function to produce an ultrasound image (e.g., a B-mode image) and display the image on its display. The hardware and software of the smart phone 2302 can detect a vein and calculate a blood vessel diameter; calculate a value (e.g., maximum value) using a plurality of blood vessel diameters; and generate and apply color-enhancement of the detected vein on the monitor.

Figure 24:
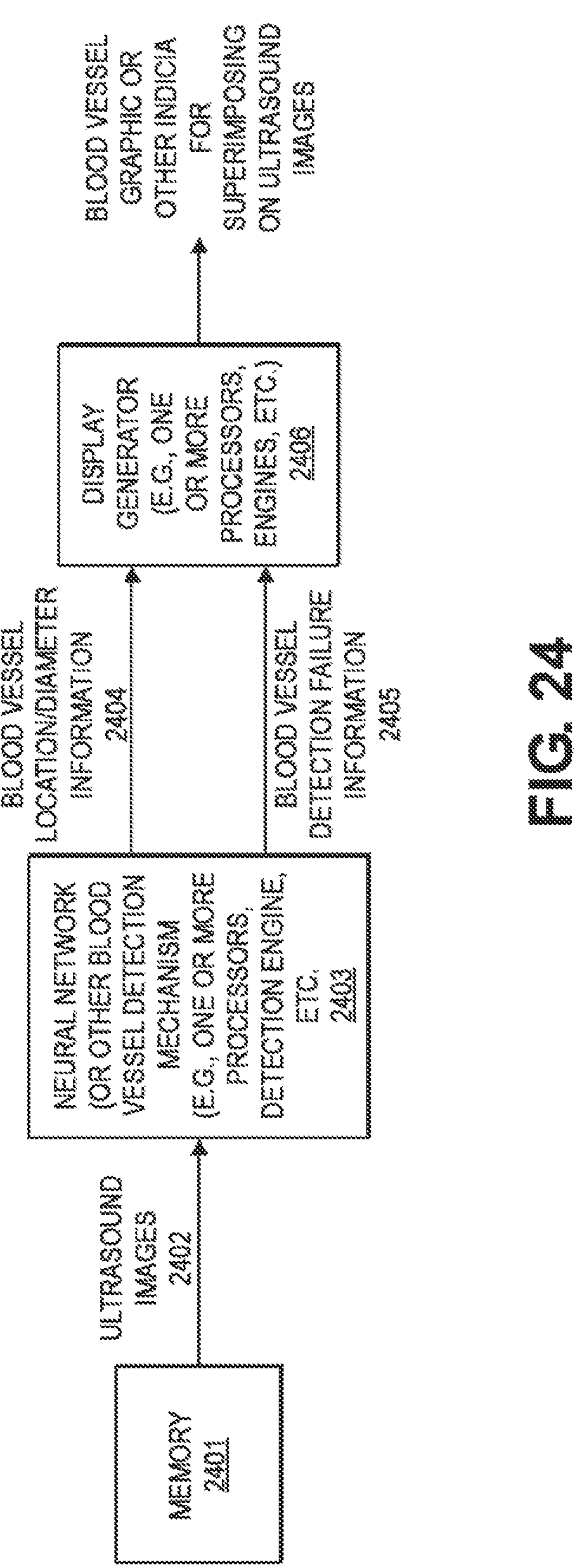
FIG. 24 illustrates a data flow diagram of a blood vessel identification and display subsystem.

FIG. 24 illustrates a data flow diagram of a blood vessel identification and display subsystem. In some embodiments, the subsystem is part of an ultrasound machine, such as that described previously in FIG. 22. Additionally or alternatively, the subsystem can operate in conjunction with an ultrasound machine by providing information to the ultrasound machine for use and/or display, and receiving information from the ultrasound machine.

Referring to FIG. 24, memory 2401 stores ultrasound images 2402. Neural network (or other blood vessel detection mechanism) 2403 receives or otherwise obtains the ultrasound images 2402. In some embodiments, neural network 2403 determines blood vessel locations and diameters in ultrasound images 2402 using AI or other machine learning algorithms and outputs this information as blood vessel location/diameter information 2404 to display generator 2406.

In some embodiments, neural network 2403 also determines when there has been a blood vessel detection failure using AI or other machine learning algorithms and outputs this information as blood vessel detection failure information 2405 to display generator 2406. In some embodiments, neural network 2403 includes one or more processors.

In response to blood vessel location/diameter information 2404 and/or blood vessel detection failure information 2405, display generator 2406 generates blood vessel graphics or other indicia for superimposition onto one or more ultrasound images.

One example of a neural network of neural network 2403 is a convolutional neural network (CNN), such as, for example, but not limited to, RetinaNet. The neural network can also contain memory units which pass state information from one instance of the network to another thus allowing the network to learn from past, and future inputs.

In some embodiments, the neural network uses “intersection over min area” (IOMA) instead of “intersection over union” (IOU), which is used in Non-Maximal Suppression (NMS). Traditionally, the deep learning approach to object detection in images uses Non-Maximal Suppression (NMS) to filter out extra boxes around images during detection. As discussed above, for object detection, in some embodiments, the ultrasound system uses rectangular boxes around what are best approximated as ellipses that represent blood vessels. As vessels themselves cannot overlap of physically enclose other vessels, an algorithm that better suppresses detections that are fully or mostly surrounded by other detections, some traditional neural networks use NMS to compute an “intersection over union” (IOU) to determine an amount of overlap between rectangular boxes. One problem with this is that if two vessels are at a 45-degree angle from each other and they are touching, then their boxes will be overlapping, even though the vessels themselves are not. Therefore, when using NMS, a neural network allows a certain amount of overlap to not throw out these vessels that are diagonal. At the same time, the neural network wants to exclude vessels that are truly overlapping. The problem can be exacerbated when one of those vessels is large and the other is small. When computing intersection over union, there are cases where there is a fairly high IOU, even when the vessels are not overlapping.

The use of IOMA would be an improvement from IOU in the cases where the sizes of the boxes are fairly different. This method would remove all cases of having a small vessel inside or mostly inside of a large vessel. In some embodiments, the neural network computes the areas of the ellipses contained within the boxes, instead of computing the area of the boxes. Using the computed ellipse area in the IOMA, the neural network can use a very small threshold for allowing overlap of the vessels and therefore removes those false positives. To reduce the computation load of computing the actual ellipse area, the neural network can use an approximation of the ellipse area.

In some embodiments, the neural network computes the radius of the two ellipses (on the line that intersects their centers) and compares the sum of the radii to the length of the segment connecting the two centers. If the sum is less than the segment length, then the neural network determines that the vessels are overlapping. Using this method, the neural network does not need to compute the area of either ellipse/box, and this lack of area computations could speed up the processing.

Alternative Embodiments

In some embodiments, the ultrasound machine acquires additional echo frames that are acquired with different look angles. In one embodiment, the additional look angles are done at a fairly steep angle to provide the AI model with more information about the sides of the blood vessel walls. In some embodiments, the ultrasound machine uses this additional information about the sides of the blood vessel walls to help the model (e.g., neural network) better determine locations of the blood vessels and aiding in the discrimination between arteries and veins. In some embodiments, these additional frames are of lower quality and resolution compared to ultrasound image frames displayed to the user, but instead the additional frames can be fed into the model along with the image frames corresponding to the echo data and that are displayed to a user. The lower resolution allows for less impact on the frame rate.

In some embodiments, the ultrasound machine obtains color frames along with the echo frames and provides them to the model of the neural network to inform the model of vessel blood flow. In some embodiments, the color frames are low resolution, low quality images that may not be shown to the user, but instead can be fed into the model along with image frames corresponding to the echo data and that are displayed to a user. Adding the additional color flow information to the frame artery/vein detection model provides the model another dimension to the data from which to learn. The lower resolution would allow for less impact on the frame rate. In some embodiments, the color information is coupled with the post inference detection information to reinforce or modify the detection.

The systems described herein constitute improvements over systems that do not display blood vessels in ultrasound images with enhancements. Rather, the systems described herein generate enhancements that include useful, and sometimes critical, information, and display the information to an operator of an ultrasound system so that the operator can apply the information to the ultrasound procedure in real real-time. Hence, the systems described herein can result in significant improvements to a patient's experience, including reducing, or even minimizing, the number of times an interventional instrument is inserted into a patient, resulting in pain and infection risk for the patient, and as well as preventing an undesired insertion of the instrument, e.g., into an artery rather than a vein. Accordingly, the patient does not perceive unnecessary pain and discomfort, and the risk of one or more of infection, thrombus due to insertion of too large of a catheter, extravasation, and damage to a vessel wall is reduced compared to conventional ultrasound systems that do not display blood vessels with enhancements. Therefore, the systems described herein can be suitable to medical procedures and examinations for which conventional ultrasound systems are not suitable.

There are a number of example embodiments described herein.

Example 1 is a method implemented by a computing device for blood vessel identification, where the method comprises: assigning, with a neural network implemented at least partially in hardware of the computing device, one of a vein classification and an artery classification to one or more blood vessels in ultrasound images; determining a misclassification for one blood vessel of the one or more blood vessels, the misclassification denoting the neural network assigning the one of the vein classification and the artery classification to the one blood vessel in one ultrasound image of the ultrasound images and the other of the vein classification and the artery classification to the one blood vessel in additional ultrasound images of the ultrasound images; and displaying, in the one ultrasound image, an indication of the other of the vein classification and the artery classification for the one blood vessel.

Example 2 is the method of example 1 that may optionally include that the one ultrasound image and the additional ultrasound images represent frames in an ultrasound video, and the one ultrasound image represents a later frame in the ultrasound video than previous frames represented by the additional ultrasound images.

Example 3 is the method of example 2 that may optionally include that the previous frames represented by the additional ultrasound images are consecutive in the ultrasound video.

Example 4 is the method of example 2 that may optionally include that the assigning the one of the vein classification and the artery classification in the one ultrasound image is based on the assigning the one of the vein classification and the artery classification in at least one of the additional ultrasound images.

Example 5 is the method of example 2 that may optionally include that the assigning the one of the vein classification and the artery classification in the one ultrasound image is based on the one ultrasound image and at least one of the additional ultrasound images.

Example 6 is the method of example 5 that may optionally include that the one ultrasound image and the at least one of the additional ultrasound images are greyscale images, and the assigning the one of the vein classification and the artery classification in the one ultrasound image includes receiving the greyscale images on separate color channels of the neural network.

Example 7 is the method of example 1 that may optionally include receiving a user selection that indicates a time interval, wherein the one ultrasound image and the additional ultrasound images represent frames in an ultrasound video and the determining the misclassification is based on a number of the frames corresponding to the time interval.

Example 8 is the method of example 1 that may optionally include determining, with the neural network, diameters of the one or more blood vessels in the ultrasound images, wherein the displaying includes displaying the indication for the one blood vessel in a color corresponding to a catheter size for the one blood vessel based on a diameter determined with the neural network for the one blood vessel.

Example 9 is the method of example 1 that may optionally include adjusting at least one neural network coefficient based on the misclassification.

Example 10 is an ultrasound system for identifying blood vessels, where the ultrasound system comprises: an image module to generate ultrasound images based on ultrasound echo signals; a neural network module to identify the blood vessels in a first image of the ultrasound images; a map module to generate a map image that indicates locations of the blood vessels in the first image identified by the neural network module; and the neural network module to identify the blood vessels in a second image of the ultrasound images based on the map image and the second image.

Example 11 is the ultrasound system of example 10 that may optionally include that the map module is configured to generate the map image to indicate the locations of the blood vessels in the first image with bounding containers.

Example 12 is the ultrasound system of example 11 that may optionally include that the bounding containers include outlines of the blood vessels.

Example 13 is the ultrasound system of example 10 that may optionally include that the map module is configured to generate the map image as a mask that indicates the locations of the blood vessels with a first pixel value and additional locations in the map image that do not correspond to the blood vessels with a second pixel value.

Example 14 is the ultrasound system of example 10 that may optionally include that the neural network module is configured to: generate a feature map from the second image that represents content of the second image in a feature space; concatenate the feature map and the map image; and identify the blood vessels in the second image based on results of the concatenation.

Example 15 is the ultrasound system of example 10 that may optionally include that the neural network module is configured to adjust at least one neural network coefficient based on a loss function of the locations of the blood vessels in the first image and additional locations of the blood vessels in the second image.

Example 16 is a method implemented by a computing device for blood vessel identification, where the method comprises: determining, with a neural network implemented at least partially in hardware of the computing device, bounding containers of blood vessels in ultrasound images; a step for determining compression amounts of the blood vessels based on the bounding containers; assigning, with the neural network, classifications of a vein classification or an artery classification to the blood vessels in the ultrasound images; and a step for determining labels for the blood vessels based on the compression amounts and the classifications, the labels indicating the blood vessels as a vein or an artery.

Example 17 is the method of example 16 that may optionally include displaying, in at least one of the ultrasound images, the labels for the blood vessels.

Example 18 is the method of example 17 that may optionally include that the determining the compression amounts and the assigning the classifications for the at least one of the ultrasound images is based on the determining the compression amounts and the assigning the classifications for additional ultrasound images in a sequence of the ultrasound images.

Example 19 is the method of example 16 that may optionally include that the step for the determining the compression amounts of the blood vessels includes: determining first lengths of the bounding containers; determining second lengths of the bounding containers; and determining ratios of the first lengths to the second lengths.

Example 20 is the method of example 16 that may optionally include that the step for the determining the labels for the blood vessels includes comparing the compression amounts to a compression threshold and determining the labels according to the classifications based on the comparing.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may include a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

What is claimed is:

1. A processing device for blood vessel identification, comprising:

a memory; and one or more processors coupled to the memory that is configured to:

assign, with a neural network implemented at least partially in hardware of the processing device, one of a vein classification and an artery classification to one or more blood vessels in ultrasound images;

determine a misclassification for a first blood vessel of the one or more blood vessels, the misclassification denoting the neural network assigning the one of the vein classification and the artery classification to the first blood vessel in a first ultrasound image of the ultrasound images and an other of the vein classification and the artery classification to the first blood vessel in one or more additional ultrasound images of the ultrasound images; and display, in the first ultrasound image, an indication that the misclassification of the one of the vein classification and the artery classification is adjusted to the other of the vein classification and the artery classification for the first blood vessel.

2. The processing device as described in claim 1, wherein the first ultrasound image and the one or more additional ultrasound images represent frames in an ultrasound video, and the first ultrasound image represents a later frame in the ultrasound video than previous frames represented by the one or more additional ultrasound images.

3. The processing device as described in claim 2, wherein the previous frames represented by the one or more additional ultrasound images are consecutive in the ultrasound video.

4. The processing device as described in claim 2, wherein said assign the one of the vein classification and the artery classification in the first ultrasound image is based on the assigning the one of the vein classification and the artery classification in the one or more additional ultrasound images.

5. The processing device as described in claim 2, wherein said assign the one of the vein classification and the artery classification in the first ultrasound image is based on the first ultrasound image and the one or more additional ultrasound images.

6. The processing device as described in claim 5, wherein the first ultrasound image and the one or more additional ultrasound images are greyscale images, and the one or more processors is further configured to: receive the greyscale images on separate color channels of the neural network.

7. The processing device as described in claim 1, wherein the one or more processors is further configured to: receive a user selection that indicates a time interval; and wherein the first ultrasound image and the one or more additional ultrasound images represent frames in an ultrasound video and said determine the misclassification is based on a number of the frames corresponding to the time interval.

8. The processing device as described in claim 1, wherein the one or more processors is further configured to: determine, with the neural network, diameters of the one or more blood vessels in the ultrasound images;

and display the indication for the one blood vessel in a color corresponding to a catheter size for the one blood vessel based on a diameter determined with the neural network for the one blood vessel.

9. The processing device as described in claim 1, wherein the one or more processors is further configured to: adjust at least one neural network coefficient based on the misclassification.

10. A method implemented by a computing device for blood vessel identification, the method comprising:

assigning, with a neural network implemented at least partially in hardware of the computing device, one of a vein classification and an artery classification to one or more blood vessels in ultrasound images;

determining a misclassification for a first blood vessel of the one or more blood vessels, the misclassification denoting the neural network assigning the one of the vein classification and the artery classification to the first blood vessel in a first ultrasound image of the ultrasound images and an other of the vein classification and the artery classification to the first blood vessel in one or more additional ultrasound images of the ultrasound images; and displaying, in the first ultrasound image, an indication that the misclassification of the one of the vein classification and the artery classification is adjusted to the other of the vein classification and the artery classification for the first blood vessel.

11. The method as described in claim 10, wherein the first ultrasound image and the one or more additional ultrasound images represent frames in an ultrasound video, and the first ultrasound image represents a later frame in the ultrasound video than previous frames represented by the one or more additional ultrasound images.

12. The method as described in claim 11, wherein the previous frames represented by the one or more additional ultrasound images are consecutive in the ultrasound video.

13. The method as described in claim 11, wherein the assigning the one of the vein classification and the artery classification in the first ultrasound image is based on the assigning the one of the vein classification and the artery classification in the one or more additional ultrasound images.

14. The method as described in claim 11, wherein the assigning the one of the vein classification and the artery classification in the first ultrasound image is based on the first ultrasound image and the one or more additional ultrasound images.

15. The method as described in claim 14, wherein the first ultrasound image and the one or more additional ultrasound images are greyscale images, and the assigning the one of the vein classification and the artery classification in the first ultrasound image includes receiving the greyscale images on separate color channels of the neural network.

16. The method as described in claim 10, further comprising:

receiving a user selection that indicates a time interval;

wherein the first ultrasound image and the one or more additional ultrasound images represent frames in an ultrasound video and the determining the misclassification is based on a number of the frames corresponding to the time interval.

17. The method as described in claim 10, further comprising:

determining, with the neural network, diameters of the one or more blood vessels in the ultrasound images;

wherein the displaying includes displaying the indication for the one blood vessel in a color corresponding to a catheter size for the one blood vessel based on a diameter determined with the neural network for the one blood vessel.

18. The method as described in claim 10, further comprising:

adjusting at least one neural network coefficient based on the misclassification.

19. A non-transitory machine readable medium comprising instructions that cause a data processing system to perform operations comprising:

assigning, with a neural network implemented at least partially in hardware of the computing device, one of a vein classification and an artery classification to one or more blood vessels in ultrasound images;

determining a misclassification for a first blood vessel of the one or more blood vessels, the misclassification denoting the neural network assigning the one of the vein classification and the artery classification to the first blood vessel in a first ultrasound image of the ultrasound images and an other of the vein classification and the artery classification to the first blood vessel in one or more additional ultrasound images of the ultrasound images; and displaying, in the first ultrasound image, an indication that the misclassification of the one of the vein classification and the artery classification is adjusted to the other of the vein classification and the artery classification for the first blood vessel.

20. The non-transitory machine readable medium as described in claim 19, wherein the first ultrasound image and the one or more additional ultrasound images represent frames in an ultrasound video, and the first ultrasound image represents a later frame in the ultrasound video than previous frames represented by the one or more additional ultrasound images.

* * * * *